US008460371B2

(12) United States Patent
Hlavka et al.

(10) Patent No.: US 8,460,371 B2
(45) Date of Patent: Jun. 11, 2013

(54) METHOD AND APPARATUS FOR PERFORMING CATHETER-BASED ANNULOPLASTY USING LOCAL PLICATIONS

(75) Inventors: Edwin J. Hlavka, Palo Alto, CA (US); Paul A. Spence, Louisville, KY (US)

(73) Assignee: Mitralign, Inc., Tewksbury, MA (US)

( * ) Notice: Subject to any disclaimer, the term of this patent is extended or adjusted under 35 U.S.C. 154(b) by 846 days.

(21) Appl. No.: 10/689,872

(22) Filed: Oct. 21, 2003

(65) Prior Publication Data
US 2004/0172046 A1     Sep. 2, 2004

Related U.S. Application Data

(60) Provisional application No. 60/420,095, filed on Oct. 21, 2002.

(51) Int. Cl.
*A61F 2/24* (2006.01)
(52) U.S. Cl.
USPC .......................................... 623/2.36; 606/139
(58) Field of Classification Search
USPC ....... 623/2.11, 2.36–2.41; 606/139, 142–143, 606/151; 128/898
See application file for complete search history.

(56) References Cited

U.S. PATENT DOCUMENTS

| 2,143,910 | A |   | 1/1939  | Didusch |
|---|---|---|---|---|
| 3,674,014 | A |   | 7/1972  | Tillander |
| 3,794,041 | A |   | 2/1974  | Frei et al. |
| 3,841,521 | A |   | 10/1974 | Jarvik |
| 3,986,493 | A |   | 10/1976 | Hendren, III |
| 4,042,979 | A |   | 8/1977  | Angell ................................ 3/1.5 |
| 4,055,861 | A |   | 11/1977 | Carpentier et al. ................. 3/1.5 |
| 4,235,238 | A | * | 11/1980 | Ogiu et al. ...................... 606/145 |
| 4,258,705 | A |   | 3/1981  | Sorensen et al. |
| 4,369,787 | A |   | 1/1983  | Lasner et al. |
| 4,489,446 | A |   | 12/1984 | Reed ................................. 3/1.5 |

(Continued)

FOREIGN PATENT DOCUMENTS

| EP | 1016377 A2 | 7/2000 |
| JP | 10504481 A | 5/1998 |

(Continued)

OTHER PUBLICATIONS

European Patent Office, European Examination Report in EP Application No. 02764186.9, Feb. 2, 2008.

(Continued)

*Primary Examiner* — Thomas J Sweet
*Assistant Examiner* — Christopher D Prone
(74) *Attorney, Agent, or Firm* — Leason Ellis LLP

(57) ABSTRACT

The present invention relates to minimally invasive methods and apparatus for performing annuloplasty. According to one aspect of the present invention, a method for performing annuloplasty includes creating a first plication in the tissue near a mitral valve of a heart, using at least a first plication element, and creating a second plication in the tissue near the mitral valve such that the second plication is substantially coupled to the first plication. In another aspect, an apparatus for performing annuloplasty includes a distal catheter portion having a sidewall defining a lumen, anchor delivery structure disposed in the lumen, and al least one anchor supported on the anchor delivery structure. The anchor delivery structure is movable from a first position wherein the anchor is disposed within the lumen, to a second position wherein the anchor is moved through an opening.

9 Claims, 35 Drawing Sheets

U.S. PATENT DOCUMENTS

| | | | |
|---|---|---|---|
| 4,532,926 A | 8/1985 | O'Holla | |
| 4,809,713 A | 3/1989 | Grayzel | |
| 4,917,689 A | 4/1990 | Coombes | 604/338 |
| 4,917,698 A | 4/1990 | Carpentier et al. | |
| 4,945,912 A | 8/1990 | Langberg | |
| 5,016,353 A | 5/1991 | Iten | |
| 5,041,129 A | 8/1991 | Hayhurst et al. | |
| 5,041,130 A | 8/1991 | Cosgrove et al. | 623/2 |
| 5,061,277 A | 10/1991 | Carpentier et al. | 623/2 |
| 5,104,407 A | 4/1992 | Lam et al. | 623/2 |
| 5,123,914 A | 6/1992 | Cope | |
| 5,171,232 A | 12/1992 | Castillo et al. | |
| 5,201,880 A | 4/1993 | Wright et al. | 623/2 |
| 5,203,777 A | 4/1993 | Lee | |
| 5,306,234 A | 4/1994 | Johnson | 604/49 |
| 5,306,296 A | 4/1994 | Wright et al. | 623/2 |
| 5,337,736 A | 8/1994 | Reddy | |
| 5,360,444 A | 11/1994 | Kusuhara | 623/2 |
| 5,364,393 A | 11/1994 | Auth et al. | |
| 5,429,131 A | 7/1995 | Scheinman et al. | |
| 5,450,860 A | 9/1995 | O'Connor | 128/898 |
| 5,452,513 A | 9/1995 | Zinnbauer et al. | |
| 5,464,023 A | 11/1995 | Viera | |
| 5,545,178 A | 8/1996 | Kensey et al. | |
| 5,565,122 A | 10/1996 | Zinnbauer et al. | |
| 5,571,215 A | 11/1996 | Sterman et al. | 623/66 |
| 5,593,424 A | 1/1997 | Northrup, III | 606/232 |
| 5,607,471 A | 3/1997 | Seguin et al. | 623/2 |
| 5,623,943 A | 4/1997 | Hackett et al. | |
| 5,626,590 A | 5/1997 | Wilk | |
| 5,640,955 A | 6/1997 | Ockuly et al. | 128/642 |
| 5,669,919 A | 9/1997 | Sanders et al. | 606/148 |
| 5,674,279 A | 10/1997 | Wright et al. | 623/2 |
| 5,682,906 A | 11/1997 | Sterman et al. | 128/898 |
| 5,690,656 A | 11/1997 | Cope et al. | |
| 5,706,827 A | 1/1998 | Ehr et al. | |
| 5,716,367 A * | 2/1998 | Koike et al. | 606/144 |
| 5,716,397 A | 2/1998 | Myers | 623/2 |
| 5,716,399 A | 2/1998 | Love | 623/2 |
| 5,776,080 A | 7/1998 | Thome et al. | |
| 5,776,189 A | 7/1998 | Khalid | 623/2 |
| 5,797,939 A | 8/1998 | Yoon | |
| 5,813,996 A | 9/1998 | St. Germain et al. | |
| 5,824,066 A | 10/1998 | Gross | 623/2 |
| 5,827,300 A | 10/1998 | Fleega | |
| 5,829,447 A | 11/1998 | Stevens et al. | 128/898 |
| 5,830,224 A | 11/1998 | Cohn et al. | 606/167 |
| 5,851,185 A | 12/1998 | Berns | |
| 5,860,920 A | 1/1999 | McGee et al. | 600/374 |
| 5,868,733 A | 2/1999 | Ockuly et al. | 606/10 |
| 5,888,240 A | 3/1999 | Carpentier et al. | 623/2 |
| 5,906,579 A | 5/1999 | Vander Salm et al. | |
| 5,911,720 A | 6/1999 | Bourne et al. | |
| 5,928,224 A | 7/1999 | Laufer | 606/27 |
| 5,931,818 A | 8/1999 | Werp et al. | 604/270 |
| 5,944,738 A | 8/1999 | Amplatz et al. | |
| 5,967,984 A | 10/1999 | Chu et al. | |
| 5,980,515 A | 11/1999 | Tu | |
| 5,984,939 A | 11/1999 | Yoon | |
| 6,015,414 A | 1/2000 | Werp et al. | |
| 6,042,581 A | 3/2000 | Ryan et al. | |
| 6,050,472 A | 4/2000 | Shibata | |
| 6,050,936 A | 4/2000 | Schweich, Jr. et al. | |
| 6,068,637 A | 5/2000 | Popov et al. | 606/159 |
| 6,068,648 A | 5/2000 | Cole et al. | |
| 6,071,292 A * | 6/2000 | Makower et al. | 606/158 |
| 6,099,460 A | 8/2000 | Denker | |
| 6,102,945 A | 8/2000 | Campbell | 623/2.37 |
| 6,126,647 A | 10/2000 | Posey et al. | |
| RE36,974 E | 11/2000 | Bonutti | |
| 6,159,234 A | 12/2000 | Bonutti et al. | |
| 6,162,168 A | 12/2000 | Schweich, Jr. et al. | |
| 6,165,119 A | 12/2000 | Schweich, Jr. et al. | |
| 6,165,120 A | 12/2000 | Schweich, Jr. et al. | |
| 6,165,183 A | 12/2000 | Kuehn et al. | 606/139 |
| 6,173,199 B1 | 1/2001 | Gabriel | |
| 6,190,353 B1 | 2/2001 | Makower et al. | 604/95 |
| 6,197,017 B1 | 3/2001 | Brock et al. | |
| 6,206,895 B1 | 3/2001 | Levinson | |
| 6,210,432 B1 | 4/2001 | Solem et al. | 623/1.15 |
| 6,231,587 B1 | 5/2001 | Makower | 606/198 |
| 6,267,781 B1 | 7/2001 | Tu | 607/113 |
| 6,269,819 B1 | 8/2001 | Oz et al. | 128/898 |
| 6,285,903 B1 | 9/2001 | Rosenthal et al. | |
| 6,287,317 B1 | 9/2001 | Makower et al. | 606/153 |
| 6,298,257 B1 | 10/2001 | Hall et al. | |
| 6,306,133 B1 | 10/2001 | Tu et al. | 606/41 |
| 6,312,447 B1 | 11/2001 | Grimes | 606/219 |
| 6,319,263 B1 | 11/2001 | Levinson | |
| 6,332,089 B1 | 12/2001 | Acker et al. | 600/424 |
| 6,332,893 B1 | 12/2001 | Mortier et al. | |
| 6,352,543 B1 | 3/2002 | Cole | |
| 6,385,472 B1 | 5/2002 | Hall et al. | |
| 6,401,720 B1 | 6/2002 | Stevens et al. | |
| 6,402,680 B2 | 6/2002 | Mortier et al. | |
| 6,402,781 B1 | 6/2002 | Langberg et al. | 623/2.36 |
| 6,406,420 B1 | 6/2002 | McCarthy et al. | |
| 6,447,522 B2 | 9/2002 | Gambale et al. | 606/108 |
| 6,461,366 B1 | 10/2002 | Seguin | 606/144 |
| 6,500,184 B1 | 12/2002 | Chan et al. | |
| 6,524,303 B1 | 2/2003 | Garibaldi | |
| 6,530,952 B2 | 3/2003 | Vesely | 623/2.18 |
| 6,537,198 B1 | 3/2003 | Vidlund et al. | |
| 6,537,314 B2 | 3/2003 | Langberg et al. | 623/2.36 |
| 6,542,766 B2 | 4/2003 | Hall et al. | |
| 6,544,230 B1 | 4/2003 | Flaherty et al. | 604/164.12 |
| 6,554,852 B1 | 4/2003 | Oberlander | |
| 6,562,019 B1 | 5/2003 | Sell | |
| 6,565,562 B1 | 5/2003 | Shah et al. | |
| 6,589,208 B2 | 7/2003 | Ewers et al. | |
| 6,594,517 B1 | 7/2003 | Nevo | |
| 6,596,014 B2 | 7/2003 | Levinson et al. | |
| 6,619,291 B2 | 9/2003 | Hlavka et al. | |
| 6,626,919 B1 | 9/2003 | Swanstrom | |
| 6,626,930 B1 | 9/2003 | Allen et al. | 606/213 |
| 6,629,534 B1 | 10/2003 | St. Goar et al. | 128/898 |
| 6,629,921 B1 | 10/2003 | Schweich, Jr. et al. | |
| 6,655,386 B1 | 12/2003 | Makower et al. | 128/898 |
| 6,656,221 B2 | 12/2003 | Taylor et al. | 623/2.11 |
| 6,669,687 B1 | 12/2003 | Saadat | |
| 6,669,707 B1 | 12/2003 | Swanstrom et al. | |
| 6,676,702 B2 | 1/2004 | Mathis | 623/2.36 |
| 6,689,164 B1 | 2/2004 | Seguin | |
| 6,699,263 B2 | 3/2004 | Cope | |
| 6,702,825 B2 | 3/2004 | Frazier et al. | |
| 6,702,826 B2 | 3/2004 | Liddicoat et al. | |
| 6,718,985 B2 | 4/2004 | Hlavka et al. | |
| 6,723,038 B1 | 4/2004 | Schroeder et al. | |
| 6,730,112 B2 | 5/2004 | Levinson | |
| 6,733,509 B2 | 5/2004 | Nobles et al. | |
| 6,736,808 B1 | 5/2004 | Motamedi et al. | |
| 6,746,472 B2 | 6/2004 | Frazier et al. | |
| 6,764,500 B1 | 7/2004 | Muijs Van De Moer et al. | |
| 6,769,434 B2 | 8/2004 | Liddicoat et al. | |
| 6,793,618 B2 | 9/2004 | Schweich, Jr. et al. | |
| 6,866,673 B2 | 3/2005 | Oren et al. | |
| 6,913,608 B2 | 7/2005 | Liddicoat et al. | |
| 6,921,407 B2 | 7/2005 | Nguyen et al. | |
| 6,923,823 B1 | 8/2005 | Bartlett et al. | |
| 6,942,694 B2 | 9/2005 | Liddicoat et al. | |
| 6,945,978 B1 | 9/2005 | Hyde | |
| 6,964,674 B1 | 11/2005 | Matsuura et al. | |
| 6,964,683 B2 | 11/2005 | Kowalsky et al. | |
| 7,004,958 B2 | 2/2006 | Adams et al. | |
| 7,037,334 B1 | 5/2006 | Hlavka et al. | |
| 7,101,395 B2 | 9/2006 | Tremulis et al. | |
| 7,166,127 B2 | 1/2007 | Spence et al. | |
| 7,211,094 B2 | 5/2007 | Gannoe et al. | |
| 2001/0005787 A1 | 6/2001 | Oz et al. | 606/142 |
| 2001/0039436 A1 | 11/2001 | Frazier et al. | |
| 2001/0041916 A1* | 11/2001 | Bonutti | 606/232 |
| 2001/0049492 A1 | 12/2001 | Frazier et al. | 604/104 |
| 2002/0013571 A1 | 1/2002 | Goldfarb et al. | 606/1 |
| 2002/0016628 A1 | 2/2002 | Langberg et al. | 623/2.36 |
| 2002/0026198 A1 | 2/2002 | Ockuly et al. | 606/108 |
| 2002/0026216 A1 | 2/2002 | Grimes | 606/213 |
| 2002/0029080 A1 | 3/2002 | Mortier et al. | |

| | | | | | | |
|---|---|---|---|---|---|---|
| 2002/0042621 A1 | 4/2002 | Liddicoat et al. ............. 606/151 | | 2005/0119735 A1 | 6/2005 | Spence et al. |
| 2002/0072758 A1 | 6/2002 | Reo et al. | | 2005/0125011 A1 | 6/2005 | Spence et al. |
| 2002/0087169 A1 | 7/2002 | Brock et al. .................. 606/139 | | 2005/0131438 A1 | 6/2005 | Cohn |
| 2002/0087173 A1 | 7/2002 | Alferness et al. ............. 606/151 | | 2005/0143811 A1 | 6/2005 | Realyvasquez |
| 2002/0087178 A1 | 7/2002 | Nobles et al. | | 2005/0148815 A1 | 7/2005 | Mortier et al. |
| 2002/0095167 A1 | 7/2002 | Liddicoat et al. ............. 606/151 | | 2005/0149014 A1 | 7/2005 | Hauck et al. |
| 2002/0100485 A1 | 8/2002 | Stevens et al. | | 2005/0159810 A1 | 7/2005 | Filsoufi |
| 2002/0103532 A1 | 8/2002 | Langberg et al. ............. 623/2.36 | | 2005/0177228 A1 | 8/2005 | Solem et al. |
| 2002/0107531 A1 | 8/2002 | Schreck et al. | | 2005/0184122 A1 | 8/2005 | Hlavka et al. |
| 2002/0128708 A1 | 9/2002 | Northrup, III et al. | | 2005/0216039 A1 | 9/2005 | Lederman |
| 2002/0156526 A1 | 10/2002 | Hlavka et al. | | 2005/0251157 A1 | 11/2005 | Saadat et al. |
| 2002/0165535 A1 | 11/2002 | Lesh et al. | | 2005/0251159 A1 | 11/2005 | Ewers et al. |
| 2002/0169359 A1 | 11/2002 | McCarthy et al. | | 2005/0251202 A1 | 11/2005 | Ewers et al. |
| 2002/0169502 A1 | 11/2002 | Mathis .......................... 623/2.11 | | 2005/0251205 A1 | 11/2005 | Ewers et al. |
| 2002/0169504 A1 | 11/2002 | Alferness et al. ............. 623/2.36 | | 2005/0251206 A1 | 11/2005 | Maahs et al. |
| 2002/0173841 A1 | 11/2002 | Ortiz et al. | | 2005/0251207 A1 | 11/2005 | Flores et al. |
| 2002/0183766 A1 | 12/2002 | Seguin | | 2005/0251208 A1 | 11/2005 | Elmer et al. |
| 2002/0183836 A1 | 12/2002 | Liddicoat et al. ............. 623/2.11 | | 2005/0251209 A1 | 11/2005 | Saadat et al. |
| 2002/0183837 A1 | 12/2002 | Streeter et al. ................ 623/2.11 | | 2005/0251210 A1 | 11/2005 | Westra et al. |
| 2002/0183838 A1 | 12/2002 | Liddicoat et al. ............. 623/2.11 | | 2005/0267571 A1 | 12/2005 | Spence et al. |
| 2002/0183841 A1 | 12/2002 | Cohn et al. .................... 623/2.36 | | 2006/0069429 A1 | 3/2006 | Spence et al. |
| 2002/0188170 A1 | 12/2002 | Santamore et al. | | 2006/0142756 A1 | 6/2006 | Davies et al. |
| 2003/0018358 A1 | 1/2003 | Saadat | | 2006/0212045 A1 | 9/2006 | Schilling et al. |
| 2003/0069593 A1 | 4/2003 | Tremulis et al. | | 2007/0010857 A1 | 1/2007 | Sugimoto et al. |
| 2003/0069636 A1 | 4/2003 | Solem et al. .................. 623/2.37 | | 2007/0080188 A1 | 4/2007 | Spence et al. |
| 2003/0078465 A1 | 4/2003 | Pai et al. | | 2007/0106310 A1 | 5/2007 | Goldin et al. |
| 2003/0078654 A1 | 4/2003 | Taylor et al. .................. 623/2.36 | | 2007/0112424 A1 | 5/2007 | Spence et al. |
| 2003/0078671 A1 | 4/2003 | Lesniak et al. | | 2008/0228165 A1 | 9/2008 | Spence et al. |
| 2003/0083538 A1 | 5/2003 | Adams et al. .................... 600/16 | | 2008/0228198 A1 | 9/2008 | Traynor et al. |
| 2003/0105474 A1 | 6/2003 | Bonutti | | 2008/0228265 A1 | 9/2008 | Spence et al. |
| 2003/0105520 A1 | 6/2003 | Alferness et al. ............. 623/2.36 | | 2008/0228266 A1 | 9/2008 | McNamara et al. |
| 2003/0120340 A1 | 6/2003 | Liska et al. | | 2008/0228267 A1 | 9/2008 | Spence et al. |
| 2003/0130730 A1 | 7/2003 | Cohn et al. .................... 623/2.36 | | 2008/0275503 A1 | 11/2008 | Spence et al. |
| 2003/0144697 A1 | 7/2003 | Mathis et al. ................. 606/232 | | | | |
| 2003/0160721 A1 | 8/2003 | Gilboa et al. | | | | |
| 2003/0171776 A1 | 9/2003 | Adams et al. | | | | |
| 2003/0171806 A1 | 9/2003 | Mathis et al. ................. 623/2.36 | | | | |
| 2003/0199974 A1 | 10/2003 | Lee et al. | | | | |
| 2003/0208195 A1 | 11/2003 | Thompson et al. | | | | |
| 2003/0212453 A1 | 11/2003 | Mathis et al. ................. 623/2.11 | | | | |
| 2003/0220685 A1 | 11/2003 | Hlavka et al. | | | | |
| 2003/0233142 A1 | 12/2003 | Morales et al. | | | | |
| 2004/0003819 A1 | 1/2004 | St. Goar et al. ............... 128/898 | | | | |
| 2004/0019378 A1 | 1/2004 | Hlavka et al. | | | | |
| 2004/0024414 A1 | 2/2004 | Downing | | | | |
| 2004/0030382 A1 | 2/2004 | St. Goar et al. | | | | |
| 2004/0039442 A1 | 2/2004 | St. Goar et al. | | | | |
| 2004/0044364 A1 | 3/2004 | DeVries et al. | | | | |
| 2004/0049211 A1 | 3/2004 | Tremulis et al. | | | | |
| 2004/0092962 A1 | 5/2004 | Thornton et al. | | | | |
| 2004/0093023 A1 | 5/2004 | Allen et al. | | | | |
| 2004/0127983 A1 | 7/2004 | Mortier et al. | | | | |
| 2004/0133063 A1 | 7/2004 | McCarthy et al. | | | | |
| 2004/0147958 A1 | 7/2004 | Lam et al. | | | | |
| 2004/0152947 A1 | 8/2004 | Schroeder et al. | | | | |
| 2004/0162568 A1 | 8/2004 | Saadat et al. | | | | |
| 2004/0167539 A1 | 8/2004 | Kuehn et al. | | | | |
| 2004/0167620 A1 | 8/2004 | Ortiz et al. | | | | |
| 2004/0172046 A1 | 9/2004 | Hlavka et al. | | | | |
| 2004/0186486 A1 | 9/2004 | Roue et al. | | | | |
| 2004/0186566 A1 | 9/2004 | Hindrichs et al. | | | | |
| 2004/0193191 A1 | 9/2004 | Starksen et al. | | | | |
| 2004/0220473 A1 | 11/2004 | Lualdi | | | | |
| 2004/0236419 A1 | 11/2004 | Milo | | | | |
| 2004/0243153 A1 | 12/2004 | Liddicoat et al. | | | | |
| 2004/0243227 A1 | 12/2004 | Starksen et al. | | | | |
| 2004/0260317 A1 | 12/2004 | Bloom et al. | | | | |
| 2005/0033446 A1 | 2/2005 | Deem et al. | | | | |
| 2005/0049681 A1 | 3/2005 | Greenhalgh et al. | | | | |
| 2005/0055087 A1 | 3/2005 | Starksen | | | | |
| 2005/0055089 A1 | 3/2005 | Macoviak et al. | | | | |
| 2005/0065550 A1 | 3/2005 | Starksen et al. | | | | |
| 2005/0065601 A1 | 3/2005 | Lee et al. | | | | |
| 2005/0075723 A1 | 4/2005 | Schroeder et al. | | | | |
| 2005/0107810 A1 | 5/2005 | Morales et al. | | | | |
| 2005/0107812 A1 | 5/2005 | Starksen et al. | | | | |
| 2005/0107871 A1 | 5/2005 | Realyvasquez et al. | | | | |
| 2005/0119523 A1 | 6/2005 | Starksen et al. | | | | |
| 2005/0119734 A1 | 6/2005 | Spence et al. | | | | |

FOREIGN PATENT DOCUMENTS

| | | |
|---|---|---|
| JP | 2002523137 A | 7/2002 |
| JP | 2002525155 A | 8/2002 |
| WO | 9604852 A1 | 2/1996 |
| WO | WO 99/00059 | 1/1999 |
| WO | WO 00/03759 | 1/2000 |
| WO | 00/18302 A2 | 4/2000 |
| WO | 0044311 A2 | 8/2000 |
| WO | 0060995 A2 | 10/2000 |
| WO | WO 00/60995 | 10/2000 |
| WO | 0067640 A2 | 11/2000 |
| WO | 0200099 A2 | 1/2002 |
| WO | 02051329 A1 | 7/2002 |
| WO | 02/085252 A1 | 10/2002 |
| WO | 02096275 A2 | 12/2002 |
| WO | 03007796 A2 | 1/2003 |
| WO | WO/03/001893 | 1/2003 |
| WO | 03/053289 A1 | 7/2003 |
| WO | 2004/045378 A2 | 6/2004 |
| WO | 2004/112658 A1 | 12/2004 |
| WO | 2005011463 A2 | 2/2005 |
| WO | 2005013832 A1 | 2/2005 |
| WO | 2005/025644 A2 | 3/2005 |
| WO | 2006064490 A1 | 6/2006 |
| WO | 2007005394 A1 | 1/2007 |

OTHER PUBLICATIONS

U.S. Patent and Trademark Office, Office Action in U.S. Appl. No. 11/111,044, Feb. 26, 2008.
U.S. Patent and Trademark Office, Office Action in U.S. Appl. No. 10/622,207, May 21, 2007.
U.S. Patent and Trademark Office, Office Action in U.S. Appl. No. 10/622,207, Jul. 14, 2006.
U.S. Patent and Trademark Office, Office Action in U.S. Appl. No. 10/622,207, Aug. 23, 2005.
U.S. Patent and Trademark Office, Office Action in U.S. Appl. No. 10/622,207, Dec. 28, 2004.
*Anatomical Landscape of Heartport Technology*, Heartport Common Stock Prospectus, Apr. 25, 1996, Cardiology Roundtable Interviews.
F. Maisano et al., *The Double-Orifice Technique as a Standardized Approach to Treat Mitral Regurgitation Due to Severe Myxomatous Disease: Surgical Technique*, European Journal of Cardio-thoracic Surgery, 1998.

Douglas P. Zipes, MD et al., *Ablation of Free Wall Acessory Pathways*, Catheter Ablation of Arrhythmias, Chapter 8, 7 pgs., 1994.

Zsolt L. Nagy et al., *Mitral Annuloplasty With a Suture Technique*, European Journal of Cardio-thoracic Surgery 18, Aug. 15, 2000, 1 pg.

David L.S. Morales et al., *Development of an Off Bypass Mitral Valve Repair*, Department of Surgery, Columbia University, College of Physicians and Surgeons, New York, NY.

http://www.hsforum.com/vol2/issue2/1999-4963 tables.html.

http:/www.hsforum.com/vol2/issue2/1999-4963figures.html.

http://medtronic.com/cardiac/heartvalves/duran_band/.

European Patent Office, International Search Report and Written Opinion in PCT Serial No. PCT/US2006/024897, Dec. 6, 2006.

U.S. Patent and Trademark Office, Office Action in U.S. Appl. No. 10/948,922, Sep. 11, 2007.

U.S. Patent and Trademark Office, Office Action in U.S. Appl. No. 11/111,044, Jul. 16, 2007.

U.S. Patent and Trademark Office, Office Action in U.S. Appl. No. 10/948,923, Mar. 18, 2008.

European Patent Office, Supplementary Search Report in EP Application No. 02764186.9, Jan. 26, 2007.

European Patent Office, Supplementary Search Report in EP Application No. 02733960.5, Jan. 25, 2007.

U.S. Patent and Trademark Office, Office Action in U.S. Appl. No. 10/949,412, Aug. 6, 2008.

U.S. Patent and Trademark Office, Office Action in U.S. Appl. No. 10/622,207, Apr. 11, 2008.

U.S. Patent and Trademark Office, International Search Report and Written Opinion in PCT Application Serial No. PCT/US2008/056620, Oct. 15, 2008.

U.S. Patent and Trademark Office, International Search Report and Written Opinion in PCT Application Serial No. PCT/US2008/080735, Dec. 17, 2008.

U.S. Patent and Trademark Office, Office Action in U.S. Appl. No. 10/949,133, Dec. 10, 2008.

Canadian Patent Office, Office Action in CA Application No. 2,500,512, Jul. 20, 2007.

Canadian Patent Office, Office Action in CA Application No. 2,500,512, Oct. 8, 2008.

European Patent Office, Supplemental Search Report in European Patent Application No. EP 03774914 dated May 20, 2009.

* cited by examiner

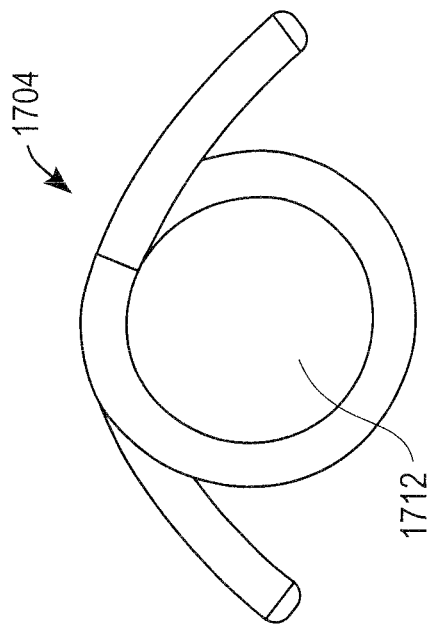
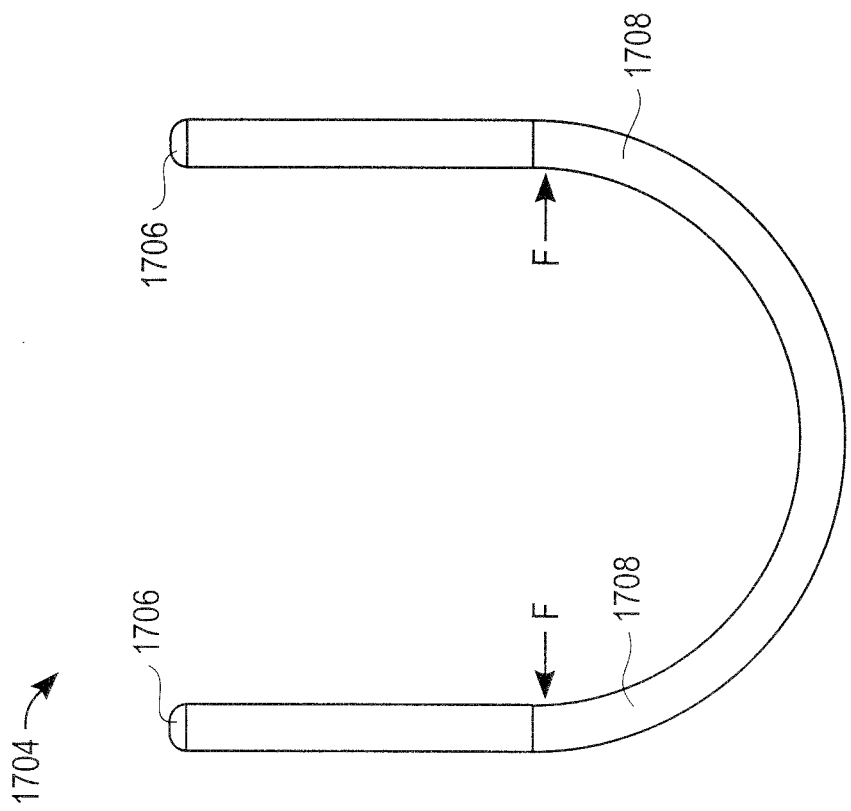
FIG. 17b
FIG. 17a

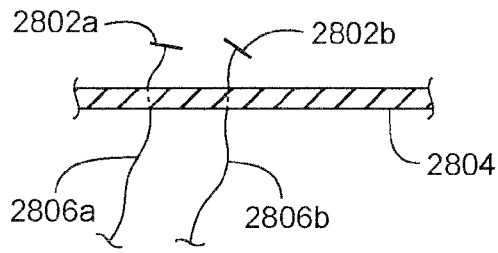
FIG. 28a
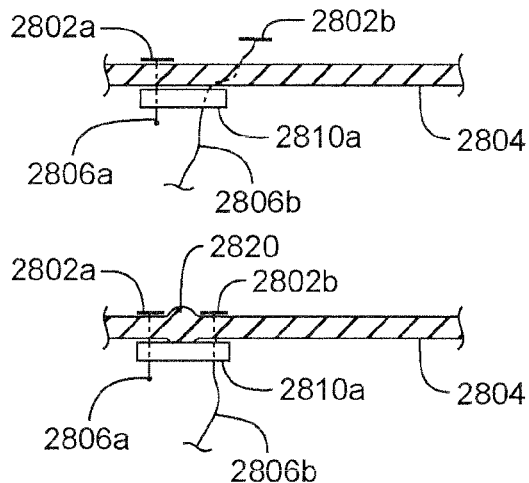
FIG. 28b
FIG. 28c
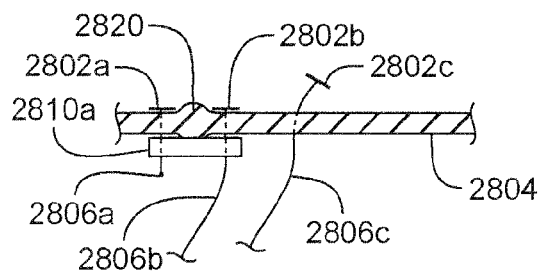
FIG. 28d
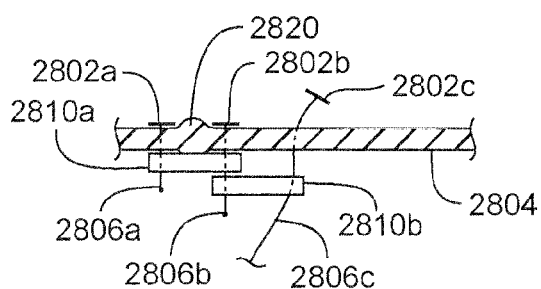
FIG. 28e
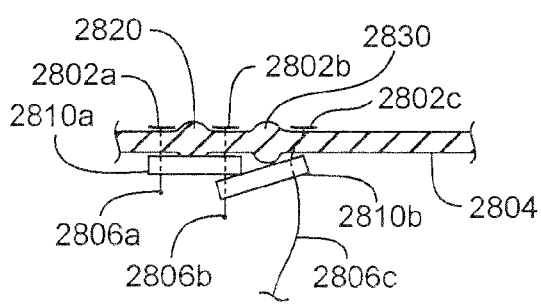
FIG. 28f

METHOD AND APPARATUS FOR PERFORMING CATHETER-BASED ANNULOPLASTY USING LOCAL PLICATIONS

The present invention claims priority of U.S. Provisional Patent Application No. 60/420,095, filed Oct. 21, 2002, which is hereby incorporated by reference in its entirety.

CROSS REFERENCE TO RELATED APPLICATIONS

The present invention is related to U.S. Pat. No. 6,619,291 entitled "Method and Apparatus for Catheter-Based Annuloplasty," filed Apr. 24, 2001 and issued Sep. 16, 2003, and to co-pending U.S. patent application Ser. No. 09/866,550, entitled "Method and Apparatus for Catheter-Based Annuloplasty Using Local Plications, which are each incorporated herein by reference in their entireties.

BACKGROUND OF THE INVENTION

1. Field of Invention

The present invention relates generally to techniques for treating mitral valve insufficiencies such as mitral valve leakage. More particularly, the present invention relates to systems and methods for treating a leaking mitral valve in a minimally invasive manner.

2. Description of the Related Art

Congestive heart failure (CHF), which is often associated with an enlargement of the heart, is a leading cause of death. As a result, the market for the treatment of CHF is becoming increasingly prevalent. For instance, the treatment of CHF is a leading expenditure of Medicare and Medicaid dollars in the United States of America. Typically, the treatment of CHF enables many who suffer from CHF to enjoy an improved quality of life.

Referring initially to FIG. 1, the anatomy of a heart, specifically the left side of a heart, will be described. The left side of a heart 104 includes a left atrium 108 and a left ventricle 112. An aorta 114 receives blood from left ventricle 112 through an aortic valve 120, which serves to prevent regurgitation of blood back into left ventricle 112. A mitral valve 116 is disposed between left atrium 108 and left ventricle 112, and effectively controls the flow of blood between left atrium 108 and left ventricle 112.

Mitral valve 116, which will be described below in more detail with respect to FIG. 2a, includes an anterior leaflet and a posterior leaflet that are coupled to cordae tendonae 124 which serve as "tension members" that prevent the leaflets of mitral valve 116 from opening indiscriminately. When left ventricle 112 contracts, cordae tendonae 124 allow the anterior leaflet to open upwards until limited in motion by cordae tendonae 124. Normally, the upward limit of opening corresponds to a meeting of the anterior and posterior leaflets and the prevention of backflow. Cordae tendonae 124 arise from a columnae carnae 128 or, more specifically, a musculi papillares of columnae carnae 128.

Left ventricle 112 includes trabeculae 132 which are fibrous cords of connective tissue that are attached to wall 134 of left ventricle 112. Trabeculae 132 are also attached to an interventricular septum 136 which separates left ventricle 112 from a right ventricle (not shown) of heart 104. Trabeculae 132 are generally located in left ventricle 112 below columnae carnae 128.

FIG. 2a is a cut-away top-view representation of mitral valve 116 and aortic valve 120. Aortic valve 120 has a valve wall 204 that is surrounded by a skeleton 208a of fibrous material. Skeleton 208a may generally be considered to be a fibrous structure that effectively forms a ring around aortic valve 120. A fibrous ring 208b, which is substantially the same type of structure as skeleton 208a, extends around mitral valve 116. Mitral valve 116 includes an anterior leaflet 212 and a posterior leaflet 216, as discussed above. Anterior leaflet 212 and posterior leaflet 216 are generally thin, flexible membranes. When mitral valve 116 is closed (as shown in FIG. 2a), anterior leaflet 212 and posterior leaflet 216 are generally aligned and contact one another to create a seal. Alternatively, when mitral valve 116 is opened, blood may flow through an opening created between anterior leaflet 212 and posterior leaflet 216.

Many problems relating to mitral valve 116 may occur and these insufficiencies may cause many types of ailments. Such problems include, but are not limited to, mitral regurgitation. Mitral regurgitation, or leakage, is the backflow of blood from left ventricle 112 into the left atrium 108 due to an imperfect closure of mitral valve 116. That is, leakage often occurs when a gap is created between anterior leaflet 212 and posterior leaflet 216.

In general, a relatively significant gap may exist between anterior leaflet 212 and posterior leaflet 216 (as shown in FIG. 2b) for a variety of different reasons. For example, a gap may exist due to congenital malformations, because of ischemic disease, or because a heart has been damaged by a previous heart attack. A gap may also be created when congestive heart failure, e.g., cardiomyopathy, or some other type of distress causes a heart to be enlarged. When a heart is enlarged, the walls of the heart, e.g., wall 134 of a left ventricle, may stretch or dilate, causing posterior leaflet 216 to stretch. It should be appreciated that anterior leaflet 212 generally does not stretch. As shown in FIG. 2b, a gap 220 between anterior leaflet 212 and stretched posterior leaflet 216' is created when wall 134' stretches. Hence, due to the existence of gap 220, mitral valve 116 is unable to close properly, and may begin to leak.

Leakage through mitral valve 116 generally causes a heart to operate less efficiently, as the heart must work harder to maintain a proper amount of blood flow therethrough. Leakage through mitral valve 116, or general mitral insufficiency, is often considered to be a precursor to CHF. There are generally different levels of symptoms associated with heart failure. Such levels are classified by the New York Heart Association (NYHA) functional classification system. The levels range from a Class 1 level which is associated with an asymptomatic patient who has substantially no physical limitations to a Class 4 level which is associated with a patient who is unable to carry out any physical activity without discomfort, and has symptoms of cardiac insufficiency even at rest. In general, correcting for mitral valve leakage may be successful in allowing the NYHA classification grade of a patient to be reduced. For instance, a patient with a Class 4 classification may have his classification reduced to Class 3 and, hence, be relatively comfortable at rest.

Treatments used to correct for mitral valve leakage or, more generally, CHF, are typically highly invasive, open-heart surgical procedures. Ventricular assist devices such as artificial hearts may be implanted in a patient whose own heart is failing. The implantation of a ventricular assist device is often expensive, and a patient with a ventricular assist device must be placed on extended anti-coagulant therapy. As will be appreciated by those skilled in the art, anti-coagulant therapy reduces the risk of blood clots being formed, as for example, within the ventricular assist device. While reducing the risks of blood clots associated with the ventricular assist device is desirable, anti-coagulant therapies may increase the risk of uncontrollable bleeding in a patient, e.g., as a result of a fall, which is not desirable.

Rather than implanting a ventricular assist device, bi-ventricular pacing devices similar to pace makers may be implanted in some cases, e.g., cases in which a heart beats inefficiently in a particular asynchronous manner. While the implantation of a bi-ventricular pacing device may be effective, not all heart patients are suitable for receiving a bi-ventricular pacing device. Further, the implantation of a bi-ventricular pacing device is expensive.

Open-heart surgical procedures which are intended to correct for mitral valve leakage, specifically, involve the implantation of replacement valves. Valves from animals, e.g., pigs, may be used to replace a mitral valve 116 in a human. While the use of a pig valve may relatively successfully replace a mitral valve, such valves generally wear out, thereby requiring additional open surgery at a later date. Mechanical valves, which are less likely to wear out, may also be used to replace a leaking mitral valve. However, when a mechanical valve is implanted, there is an increased risk of thromboembolism, and a patient is generally required to undergo extended anti-coagulant therapies.

A less invasive surgical procedure involves heart bypass surgery associated with a port access procedure. For a port access procedure, the heart may be accessed by cutting a few ribs, as opposed to opening the entire chest of a patient. In other words, a few ribs may be cut in a port access procedure, rather than opening a patient's sternum.

One open-heart surgical procedure that is particularly successful in correcting for mitral valve leakage and, in addition, mitral regurgitation, is an annuloplasty procedure. During an annuloplasty procedure, an annuloplasty ring may be implanted on the mitral valve to cause the size of a stretched mitral valve 116 to be reduced to a relatively normal size. FIG. 3 is a schematic representation of an annuloplasty ring. An annuloplasty ring 304 is shaped approximately like the contour of a normal mitral valve. That is, annuloplasty ring 304 is shaped substantially like the letter "D." Typically, annuloplasty ring 304 may be formed from a rod or tube of biocompatible material, e.g., plastic, that has a DACRON mesh covering.

In order for annuloplasty ring 304 to be implanted, a surgeon surgically attaches annuloplasty ring 304 to the mitral valve on the atrial side of the mitral valve. Conventional methods for installing ring 304 require open-heart surgery which involve opening a patient's sternum and placing the patient on a heart bypass machine. As shown in FIG. 4, annuloplasty ring 304 is sewn to a posterior leaflet 318 and an anterior leaflet 320 of a top portion of mitral valve 316. In sewing annuloplasty ring 304 onto mitral valve 316, a surgeon generally alternately acquires a relatively large amount of tissue from mitral tissue, e.g., a one-eighth inch bite of tissue, using a needle and thread, followed by a smaller bite from annuloplasty ring 304. Once a thread has loosely coupled annuloplasty ring 304 to mitral valve tissue, annuloplasty ring 304 is slid onto mitral valve 316 such that tissue that was previously stretched out, e.g., due to an enlarged heart, is effectively pulled in using tension applied by annuloplasty ring 304 and the thread which binds annuloplasty ring 304 to the mitral valve tissue. As a result, a gap, such as gap 220 of FIG. 2b, between anterior leaflet 320 and posterior leaflet 318 may be substantially closed off. After the mitral valve is shaped by ring 304, the anterior and posterior leaflets 320, 318 will reform to create a new contact line and will enable mitral valve 318 to appear and to function as a normal mitral valve.

Once implanted, tissue generally grows over annuloplasty ring 304, and a line of contact between annuloplasty ring 304 and mitral valve 316 will essentially enable mitral valve 316 to appear and function as a normal mitral valve. Although a patient who receives annuloplasty ring 304 may be subjected to anti-coagulant therapies, the therapies are not extensive, as a patient is only subjected to the therapies for a matter of weeks, e.g., until tissue grows over annuloplasty ring 304.

A second surgical procedure which is generally effective in reducing mitral valve leakage involves placing a single edge-to-edge suture in the mitral valve. With reference to FIG. 5a, such a surgical procedure, e.g., an Alfieri stitch procedure or a bow-tie repair procedure, will be described. An edge-to-edge stitch 404 is used to stitch together an area at approximately the center of a gap 408 defined between an anterior leaflet 420 and a posterior leaflet 418 of a mitral valve 416. Once stitch 404 is in place, stitch 404 is pulled in to form a suture which holds anterior leaflet 420 against posterior leaflet 418, as shown. By reducing the size of gap 408, the amount of leakage through mitral valve 416 may be substantially reduced.

Although the placement of edge-to-edge stitch 404 is generally successful in reducing the amount of mitral valve leakage through gap 408, edge-to-edge stitch 404 is conventionally made through open-heart surgery. In addition, the use of edge-to-edge stitch 404 is generally not suitable for a patient with an enlarged, dilated heart, as blood pressure causes the heart to dilate outward, and may put a relatively large amount of stress on edge-to-edge stitch 404. For instance, blood pressure of approximately 120/80 or higher is typically sufficient to cause the heart to dilate outward to the extent that edge-to-edge stitch 404 may become undone, or tear mitral valve tissue.

Another surgical procedure which reduces mitral valve leakage involves placing sutures along a mitral valve annulus around the posterior leaflet. A surgical procedure which places sutures along a mitral valve with be described with respect to FIG. 5b. Sutures 504 are formed along an annulus 540 of a mitral valve 516 around a posterior leaflet 518 of mitral valve 516, and may be formed as a double track, e.g., in two "rows," from a single strand of suture material. Sutures 504 are tied off at approximately a central point 506 of posterior leaflet 518. Pledgets 546 are often positioned under selected sutures 504, e.g., at central point 506, to prevent sutures 504 from tearing through annulus 540. When sutures 504 are tied off, annulus 540 may effectively be tightened to a desired size such that the size of a gap 508 between posterior leaflet 518 and an anterior leaflet 520 may be reduced.

The placement of sutures 504 along annulus 540, in addition to the tightening of sutures 504, is generally successful in reducing mitral valve leakage. However, the placement of sutures 504 is conventionally accomplished through open-heart surgical procedures. That is, like other conventional procedures, a suture-based annuloplasty procedure is invasive.

While invasive surgical procedures have proven to be effective in the treatment of mitral valve leakage, invasive surgical procedures often have significant drawbacks. Any time a patient undergoes open-heart surgery, there is a risk of infection. Opening the sternum and using a cardiopulmonary bypass machine has also been shown to result in a significant incidence of both short and long term neurological deficits. Further, given the complexity of open-heart surgery, and the significant associated recovery time, people who are not greatly inconvenienced by CHF symptoms, e.g., people at a Class 1 classification, may choose not to have corrective surgery. In addition, people who most need open heart surgery, e.g., people at a Class 4 classification, may either be too frail or too weak to undergo the surgery. Hence, many people who may benefit from a surgically repaired mitral valve may not undergo surgery.

Therefore, what is needed is a minimally invasive treatment for mitral valve leakage. Specifically, what is desired is a method for reducing leakage between an anterior leaflet and a posterior leaflet of a mitral valve that does not require conventional surgical intervention.

SUMMARY OF THE INVENTION

The present invention relates to a non-invasive method of performing annuloplasty. Performing an annuloplasty on a mitral valve by accessing the left ventricle of the heart, as for example using a catheter, enables complicated surgical procedures to be avoided when treating mitral valve leakage. Avoiding open-heart surgical procedures generally makes annuloplasty more accessible to patients who may benefit from annuloplasty. As mitral valve leakage is often considered to be an early indicator of congestive heart failure, a minimally invasive annuloplasty procedure that corrects for leakage problems, such as one which involves positioning discrete plications in fibrous tissue around the mitral valve, may greatly improve the quality of life of many patients who might not be suitable for invasive annuloplasty procedures.

According to one aspect of the present invention, a method for performing annuloplasty includes creating a first plication in the tissue near a mitral valve of a heart, using at least a first plication element, and creating a second plication in the tissue near the mitral valve such that the second plication is substantially coupled to the first plication. In one embodiment, the method also includes accessing a left ventricle of the heart to provide the first plication element to the left ventricle, and engaging the first plication element to the tissue near the mitral valve. Engaging the first plication element includes causing the first plication element to substantially pass through a portion of the tissue to substantially anchor the first plication element to the tissue near the mitral valve.

According to another aspect of the present invention, a method for performing annuloplasty includes accessing a heart to provide a plurality of plication elements to the heart. The plurality of plication elements are provided to the heart through a catheter arrangement, and include a first anchor arrangement. The method also includes engaging the first anchor arrangement to tissue near a mitral valve of the heart using the catheter arrangement by causing the first anchor arrangement to substantially pass through the tissue to substantially anchor the first anchor arrangement to the tissue near the mitral valve. Finally, the method includes creating at least a first plication and a second plication using the first anchor arrangement.

In accordance with still another embodiment of the present invention, a method for performing annuloplasty includes accessing an area of a heart to provide a first plication element to the area using a catheter arrangement which has a first portion and a second portion, and substantially anchoring the first portion of the catheter arrangement to tissue near a mitral valve of the heart. The method further includes positioning a tip of the second portion of the catheter arrangement at a first distance from the first portion, and substantially engaging the first anchor to the tissue near the mitral valve of the heart using the second portion of the catheter arrangement. Substantially engaging the first anchor includes causing the first anchor to substantially pass through a portion of the tissue to substantially anchor the first anchor to the tissue near the mitral valve using the second portion of the catheter arrangement. In one embodiment, substantially anchoring the first portion of the catheter arrangement to tissue near the mitral valve of the heart includes positioning the first portion of the catheter arrangement over a guide that is at least temporarily anchored to the tissue near the mitral valve.

These and other advantages of the present invention will become apparent upon reading the following detailed descriptions and studying the various figures of the drawings.

BRIEF DESCRIPTION OF THE DRAWINGS

The invention may best be understood by reference to the following description taken in conjunction with the accompanying drawings in which:

FIG. 17a is a representation of a local plication element, which is formed from a shape memory material, in an open state in accordance with an embodiment of the present invention.

FIG. 17b is a representation of the local plication element of FIG. 17a in a closed state in accordance with an embodiment of the present invention.

FIGS. 28a-f are representations of anchors and lockers which are used in a process of creating a daisy chain of plications in accordance with an embodiment of the present invention.

DETAILED DESCRIPTION OF THE EMBODIMENTS

Invasive, open-heart surgical procedures are generally effective in the treatment of mitral valve leakage. However, open-heart surgical procedures may be particularly hazardous to some patients, e.g., frail patients or patients who are considered as being very ill, and undesirable to other patients, e.g., patients who are asymptomatic and do not wish to undergo a surgical procedure. As such, open-heart surgical procedures to correct mitral valve leakage or, more generally, mitral valve insufficiency, are not suitable for many patients who would likely benefit from reducing or eliminating the mitral valve leakage.

A catheter-based annuloplasty procedure enables annuloplasty to be performed on a patient without requiring that the patient undergo open-heart surgery, or be placed on cardiopulmonary bypass. Catheters may be introduced into the left ventricle of a heart through the aorta to position a guide wire and plication implants on the ventricular side of a mitral valve, i.e., under a mitral valve. Catheters may also be used to couple the plication implants to fibrous tissue associated with the skeleton of the heart around the mitral valve.

The use of catheters to perform an annuloplasty procedure by delivering and engaging plication implants or structures enables the annuloplasty procedure to be performed without open-heart surgery, and without a bypass procedure. Recovery time associated with the annuloplasty, as well as the risks associated with annuloplasty, may be substantially minimized when the annuloplasty is catheter-based. As a result, annuloplasty becomes a more accessible procedure, since many patients who might previously not have received treatment for mitral valve leakage, e.g., frail patients and asymptomatic patients, may choose to undergo catheter-based annuloplasty.

Figure 1:
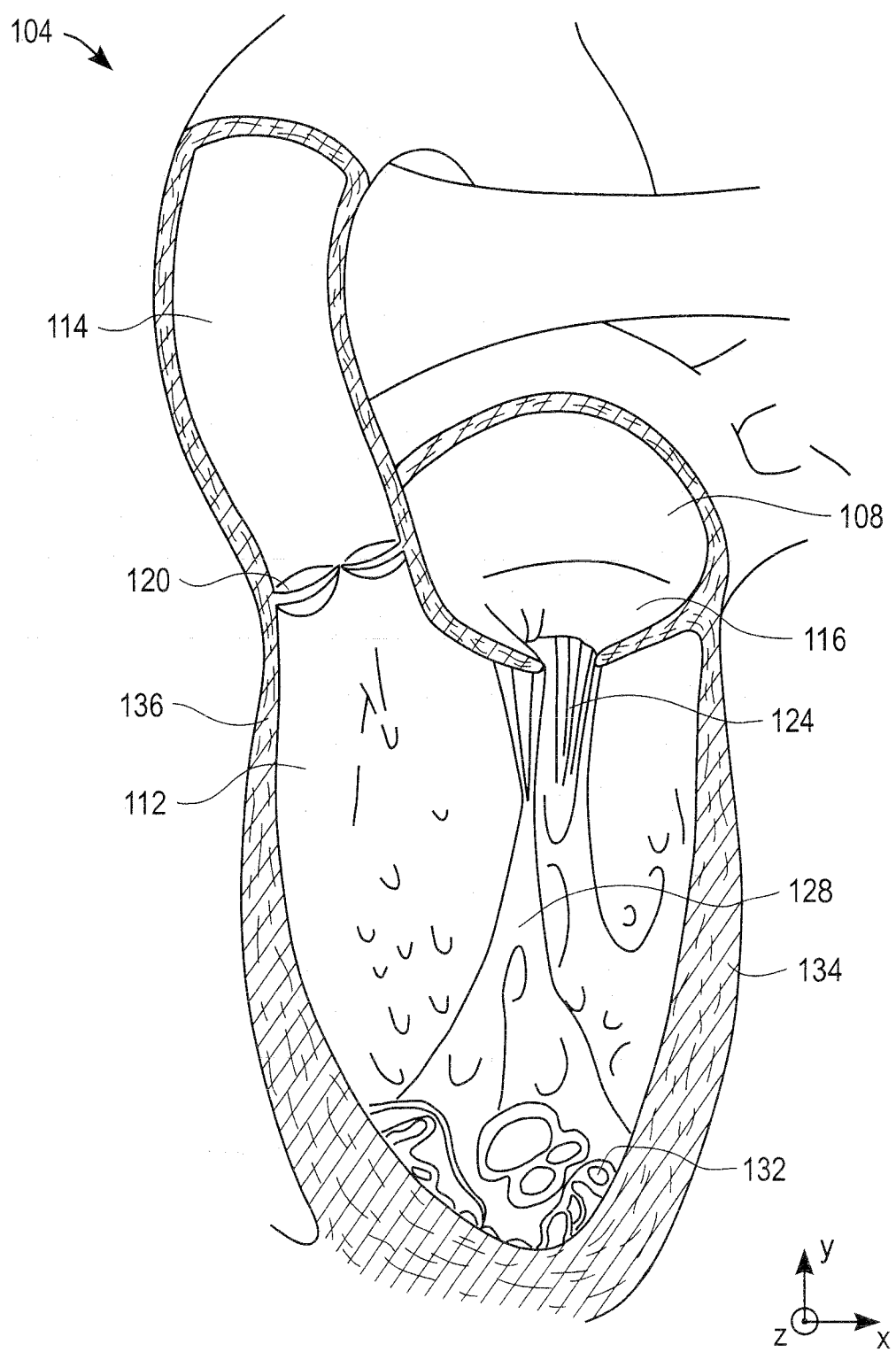
FIG. 1 is a cross-sectional front-view representation of the left side of a human heart.
Figure 2A:
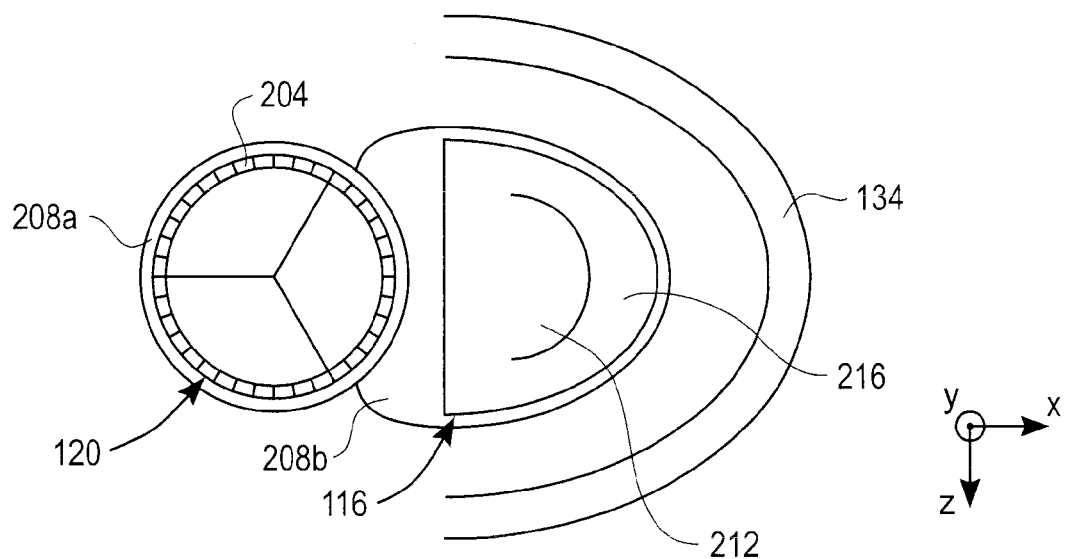
FIG. 2a is a cut-away top-view representation of the mitral valve and the aortic valve of FIG. 1.
Figure 2B:
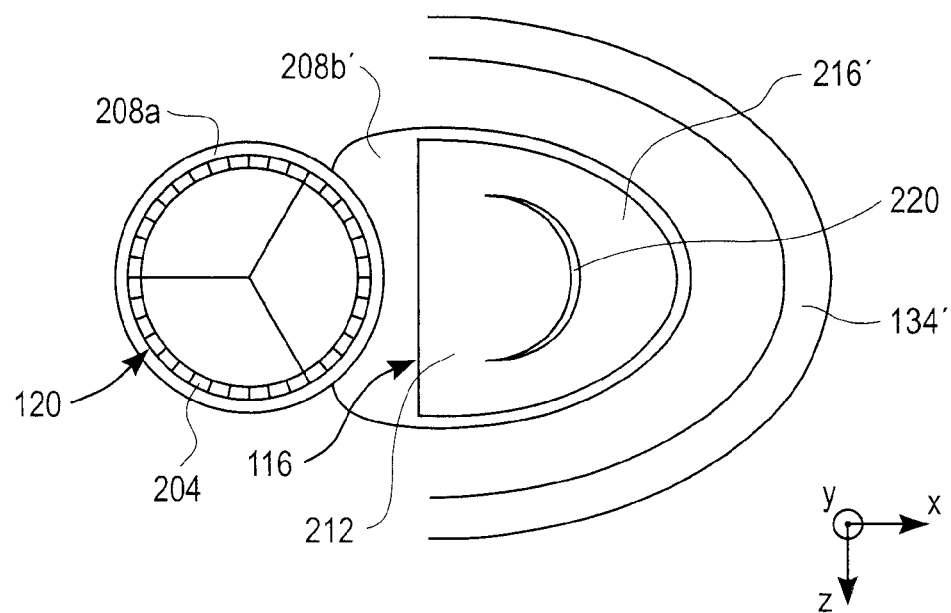
FIG. 2b is a cut-away representation of a stretched mitral valve and an aortic valve.
Figure 3:
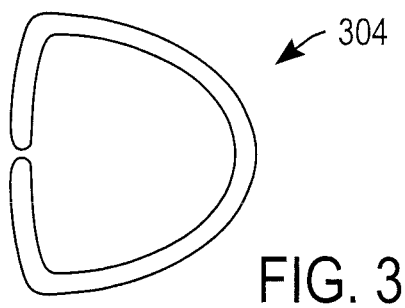
FIG. 3 is a representation of an annular ring that is suitable for use in performing a conventional annuloplasty procedure.
Figure 4:
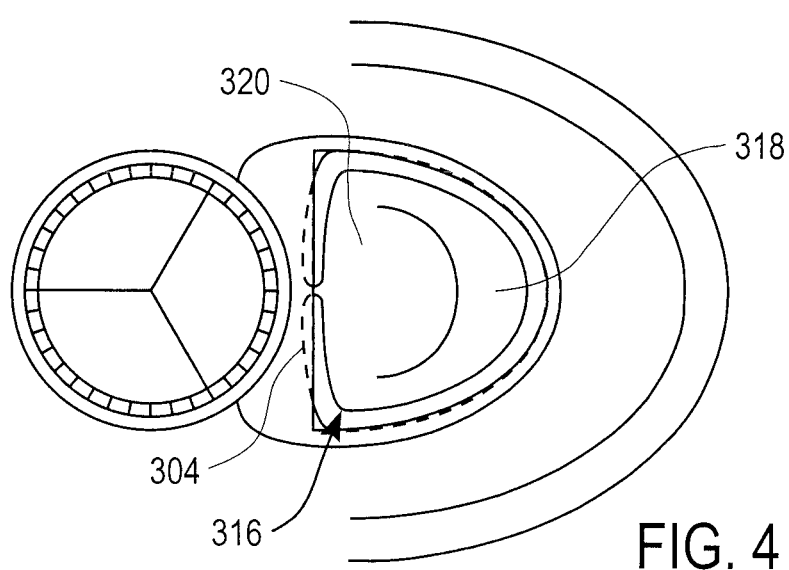
FIG. 4 is a representation of a mitral valve and an aortic valve after the annular ring of FIG. 3 has been implanted.
Figure 5A:
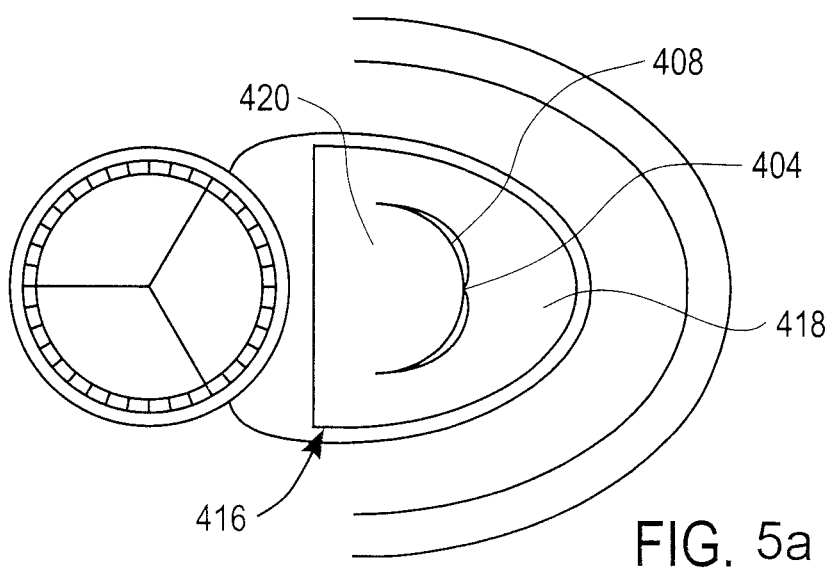
FIG. 5a is a representation of a mitral valve and an aortic valve after a single edge-to-edge suture has been applied to reduce mitral regurgitation.
Figure 5B:
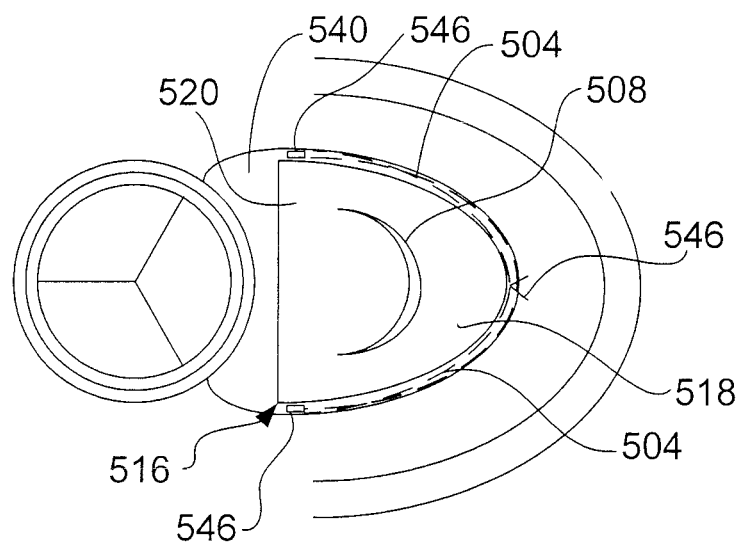
FIG. 5b is a representation of a mitral valve and an aortic valve after sutures along a mitral valve annulus have been applied to reduce mitral regurgitation.
Figure 6A:
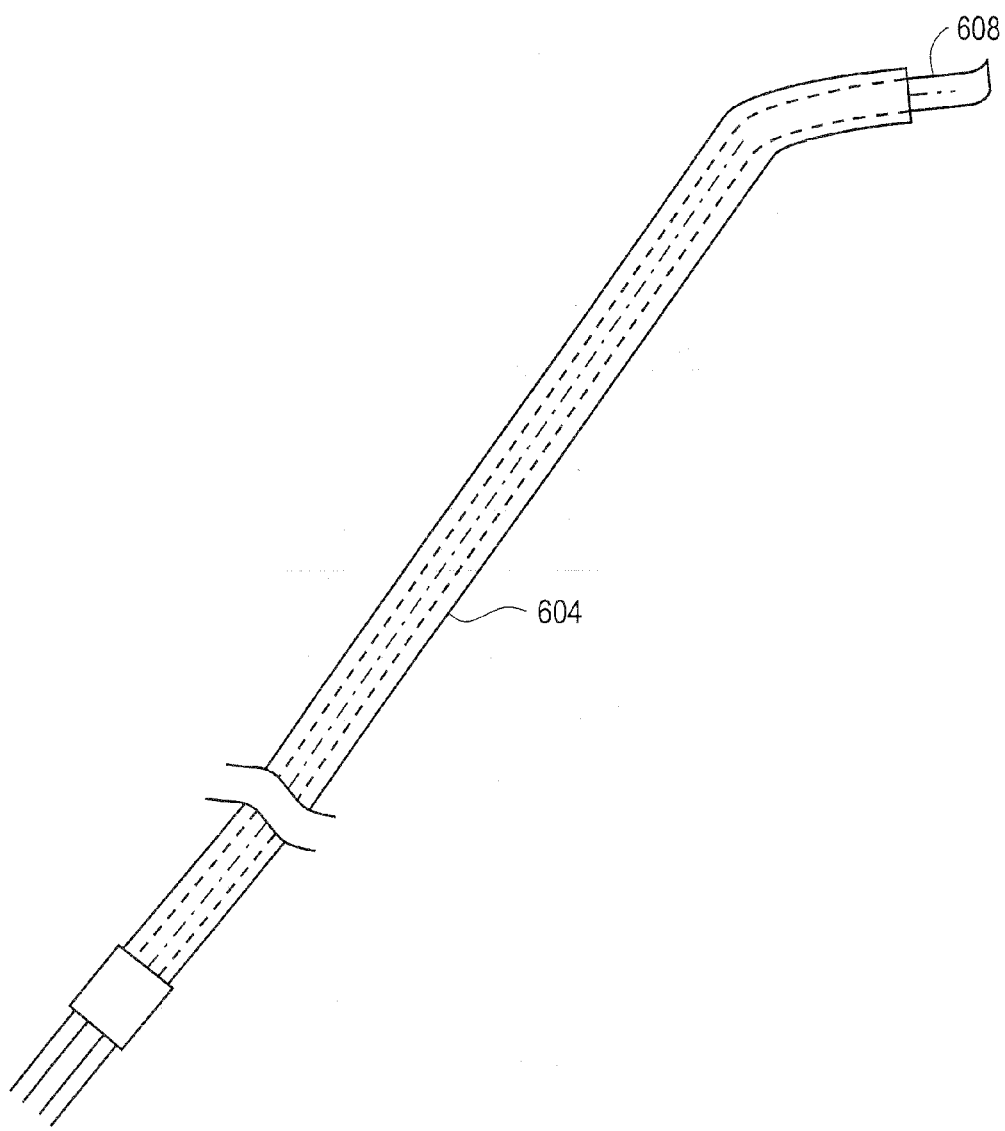
FIG. 6a is a representation of a delivery tube and a J-catheter in accordance with an embodiment of the present invention.

To begin a catheter-based annuloplasty procedure, a delivery tube and a J-catheter may be inserted into a left ventricle of the heart through the aorta. Inserting the delivery tube and the J-catheter through the aorta enables the left ventricle of the heart to be reached substantially without coming into contact with trabeculae or the cordae tendonae in the left ventricle. FIG. 6a is a diagrammatic representation of a delivery tube and a J-catheter in accordance with an embodiment of the present invention. Delivery tube 604 has a substantially circular cross section, and is configured to receive a J-catheter 608. J-catheter 608 is arranged to move longitudinally through and opening in delivery tube 604 as needed.

In general, delivery tube 604 is an elongated body which may be formed from a flexible, durable, biocompatible material such as nylon, urethane, or a blend of nylon and urethane, e.g., PEBAX®. Likewise, J-catheter 608, which is also an elongated body, may also be formed from a biocompatible material. A material used to form J-catheter 608 is typically also relatively flexible. In the described embodiment, a tip of J-catheter 608 is rigid enough to allow the tip of J-catheter 608 to maintain a relatively curved shape, e.g., a "J" shape. The curve in J-catheter 608 is configured to facilitate the positioning of a gutter catheter, as will be described below with respect to FIGS. 7a-c.

Figure 6B:
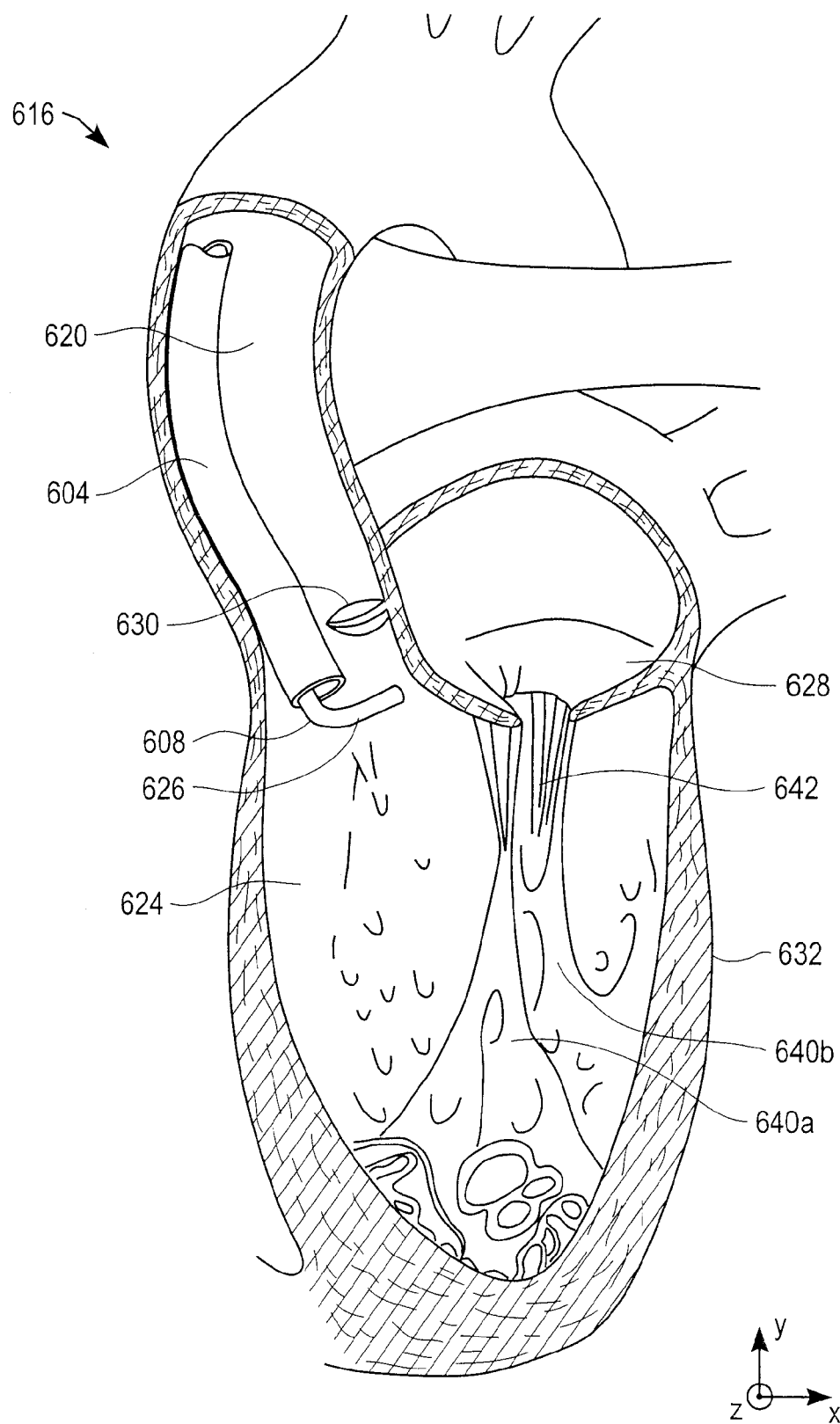
FIG. 6b is a cut-away front view of the left side of a heart in which the delivery tube and the J-catheter of FIG. 6a have been inserted in accordance with an embodiment of the present invention.

FIG. 6b is a schematic representation of delivery tube 604 and J-catheter 608 positioned within a heart in accordance with an embodiment of the present invention. As shown, after delivery tube 604 and J-catheter 608 are effectively "snaked" or inserted through a femoral artery, portions of delivery tube 604 and of J-catheter 608 are positioned within an aorta 620 of a heart 616. A tip 626 of J-catheter 608, which is substantially oriented at a right angle from the body of J-catheter 608, and an end of delivery tube 604 are oriented such that they pass through an aortic valve 630. Hence, an end of delivery tube 604 and tip 626 are positioned at a top portion of left ventricle 624, where wall 632 of left ventricle 624 is relatively smooth. The relative smoothness of the top portion of left ventricle 624 enables a catheter to be properly positioned within left ventricle 624 by guiding the tip of the catheter along wall 632. In one embodiment, tip 626 is oriented such that it is positioned approximately just below a mitral valve 628 on the ventricular side of mitral valve 628.

Once positioned within left ventricle 624, J-catheter 608 may be rotated within delivery tube 604 such that tip 626 is may enable a gutter catheter fed therethrough to run along the contour of wall 632. Typically, the gutter catheter runs along the contour of wall 632 in an area that is effectively defined between a plane associated with papillary muscles 640, a plane associated with the posterior leaflet of mitral valve 628, cordae tendonae 642, and wall 632. A "gutter" is located in such an area or region and, more specifically, is positioned substantially right under mitral valve 628 where there is a relatively insignificant amount of trabeculae.

Figure 7A:
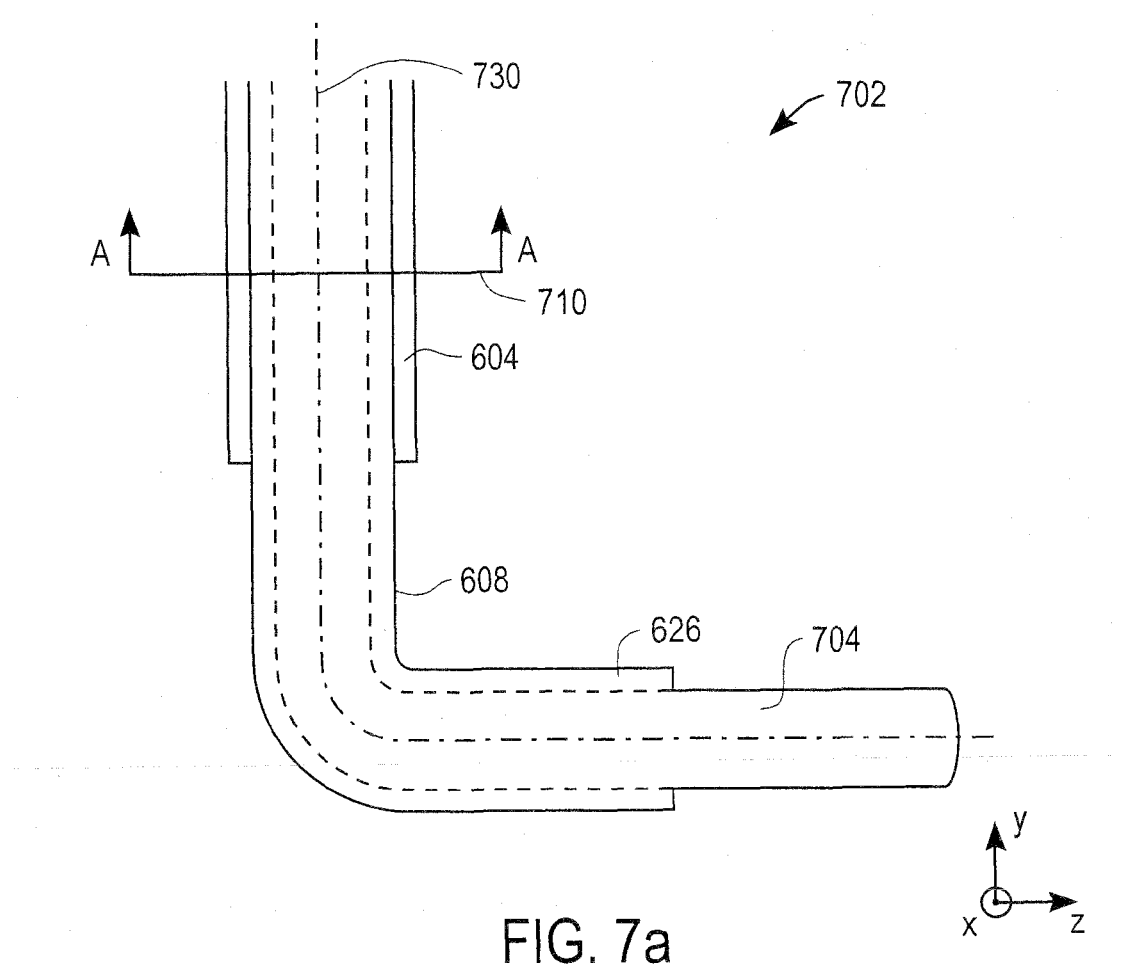
FIG. 7a is a representation of a catheter assembly in accordance with an embodiment of the present invention.
Figure 7B:
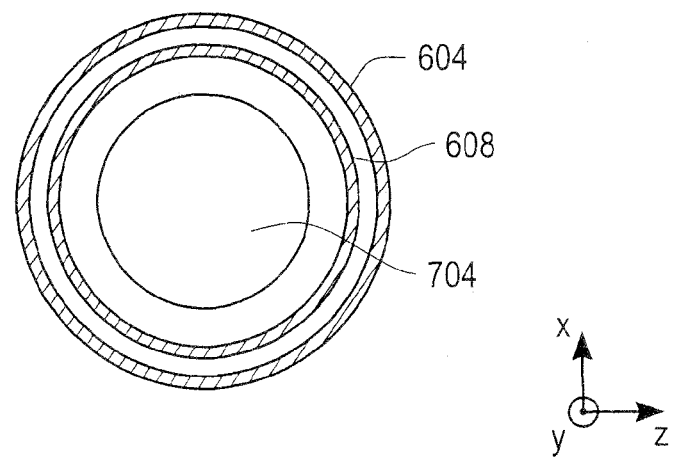
FIG. 7b is a cross-sectional representation of the catheter assembly of FIG. 7a in accordance with an embodiment of the present invention.
Figure 7C:
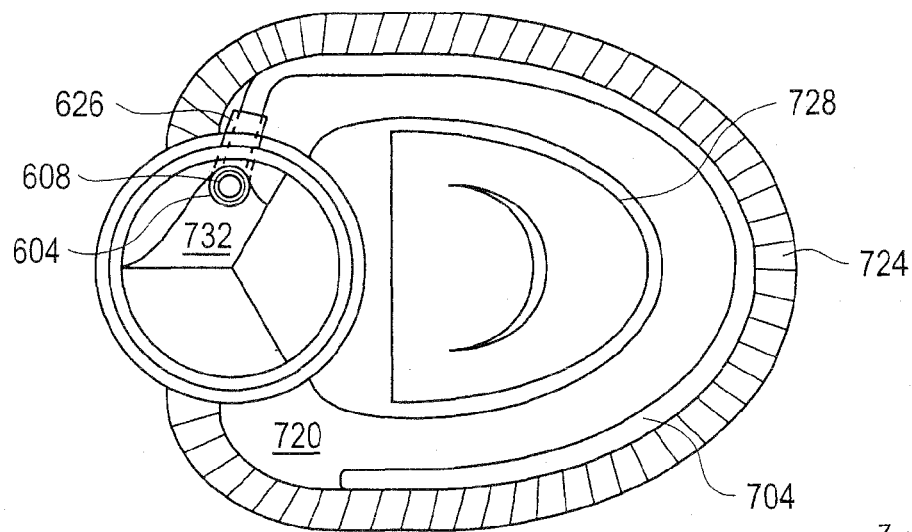
FIG. 7c is a cut-away top-view representation of a left ventricle in which the gutter catheter of FIGS. 7a and 7b has been positioned in accordance with an embodiment of the present invention.

With reference to FIGS. 7a-7c, a gutter catheter will be described in accordance with an embodiment of the present invention. A gutter catheter 704, which is part of a catheter assembly 702 as shown in FIG. 7a, is arranged to be extended through J-catheter 626 such that gutter catheter 704 may be steered within a left ventricle just beneath a mitral valve. Gutter catheter 704, which may include a balloon tip (not shown), is typically formed from a flexible material such as nylon, urethane, or PEBAX®. In one embodiment, gutter catheter 704, which is steerable, may be formed using a shape memory material.

As shown in FIG. 7a and FIG. 7b, which represents a cross section of catheter assembly 702 taken at a location 710, gutter catheter 704 is at least partially positioned within J-catheter 608 which, in turn, is at least partially positioned within delivery tube 604. Gutter catheter 704 may be free to rotate within and extend through J-catheter 608, while J-catheter 608 may be free to rotate within and extend through delivery tube 604.

Referring next to FIG. 7c, the positioning of gutter catheter 704 within a left ventricle of the heart will be described in accordance with an embodiment of the present invention. It should be appreciated that the representation of gutter catheter 704 within a left ventricle 720 has not been drawn to scale, for ease of illustration and ease of discussion. For instance, the distance between a wall 724 of left ventricle 720 and a mitral valve 728 has been exaggerated. In addition, it should also be appreciated that the positioning of delivery tube 604 and, hence, J-catheter 608 and gutter catheter 704 within aortic valve 732 may vary.

Gutter catheter 704 protrudes through tip 626 of J-catheter 608, and, through steering, essentially forms an arc shape similar to that of mitral valve 728 along the contour of a wall 724 of left ventricle 720 just beneath mitral valve 728, i.e., along the gutter of left ventricle 720. Wall 724 of left ventricle 720 is relatively smooth just beneath mitral valve 728, i.e., generally does not include trabeculae. Hence, inserting catheter assembly 702 through an aortic valve 732 into an upper portion left ventricle 720 allows gutter catheter 704 to be navigated within left ventricle 720 along wall 724 substantially without being obstructed by trabeculae or cordae tendonae.

Figure 8:
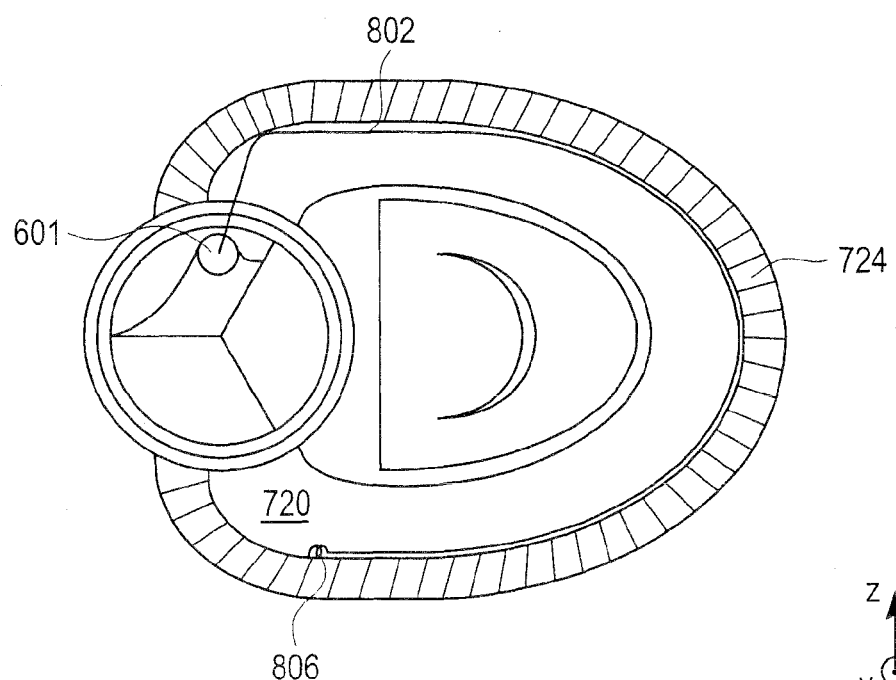
FIG. 8 is a cut-away top-view representation of a left ventricle in which a guide wire has been positioned in accordance with an embodiment of the present invention.

Gutter catheter 704 generally includes an opening or lumen (not shown) that is sized to accommodate a guide wire through which a guide wire may be inserted. The opening may be located along the central axis of gutter catheter 704, i.e., central axis 730 as shown in FIG. 7a. Delivering a guide wire through gutter catheter 704 enables the guide wire to effectively follow the contour of wall 724. In general, the guide wire may include an anchoring tip which enables the guide wire to be substantially anchored against wall 724. FIG. 8 is a diagrammatic top-view cut-away representation of a left side of a heart in which a guide wire has been positioned in accordance with an embodiment of the present invention. It should be appreciated that the representation of the left side of a heart in FIG. 8 has not been drawn to scale, and that various features have been exaggerated for ease of discussion. A guide wire 802 is positioned along wall 724 of left ventricle 720. Once guide wire 802 is inserted through gutter catheter 704 of FIGS. 7a-7c, and anchored against wall 724 using an anchoring tip 806, gutter catheter 704, along with J-catheter 708, are withdrawn from the body of the patient. It should be appreciated that delivery tube 604 typically remains positioned within the aorta after guide wire 802 is anchored to wall 724.

Guide wire 802, which may be formed from a material such as stainless steel or a shape memory material, is generally anchored such that guide wire 802 effectively passes along a large portion of wall 724. Typically, guide wire 802 serves as a track over which a catheter that carries plication structures may be positioned, i.e., a lumen of a catheter that delivers a plication element may pass over guide wire 802. Such a catheter may include a balloon structure (not shown), or an expandable structure, that may facilitate the positioning of local plication structures by pushing the local plication structures substantially against the fibrous tissue around the mitral valve.

Figure 9A:
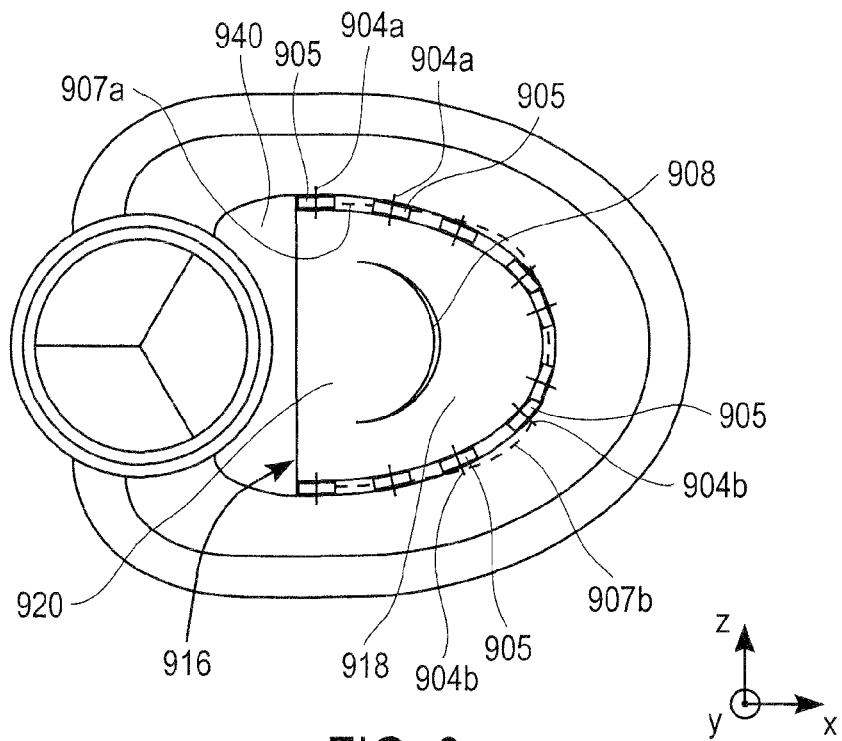
FIG. 9a is a cut-away top-view representation of a left ventricle of the heart in which local plication suture structures have been implanted in accordance with an embodiment of the present invention.

Forming local plications causes bunches of the fibrous tissue around the mitral valve to be captured or gathered, thereby causing dilation of the mitral valve to be reduced. In general, the local plications are discrete plications formed in the fibrous tissue around the mitral valve using suture structures or discrete mechanical elements. FIG. 9a is a representation of a top-down cut-away view of a left ventricle of the heart in which local plication suture structures have been implanted in accordance with an embodiment of the present invention. Suture structures, which include T-bars 904 and threads 907, are implanted in tissue near a mitral valve 916, e.g., an annulus of mitral valve 916. Typically, the tissue in which suture structures are implanted is fibrous tissue 940 which is located substantially around mitral valve 916. Suitable suture structures include, but are not limited to, structures which include T-bars 904 and threads 907, as will be described below with reference to FIGS. 10a, 10b, 11, and 12a-c.

Figure 13A:
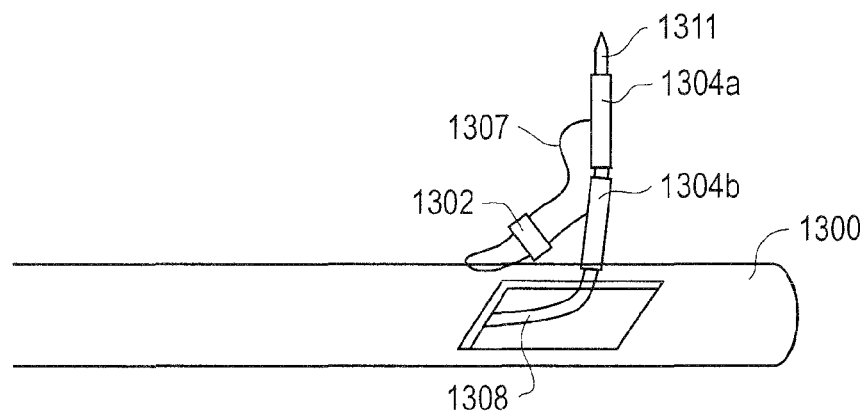
FIG. 13a is a representation of a first catheter which is suitable for use in delivering and implementing a suture structure in accordance with an embodiment of the present invention.

Since T-bars 904 or similar structures, when implanted, may cut through tissue 940, pledgets 905 may against a ventricular side tissue 940 to effectively "cushion" T-bars 904. Hence, portions of T-bars 904 are positioned above mitral valve 916, i.e., on an atrial side of mitral valve 916, while pledgets 905 are positioned on the ventricular side of mitral valve 916. It should be appreciated that additional or alternative pledgets may be positioned on the atrial side of mitral valve 916, substantially between tissue 940 and T-bars 904. Catheters which deliver suture structures 904 to an atrial side of mitral valve 916 from a ventricular side of mitral valve 916 will be discussed below with respect to FIGS. 13a-c.

In the described embodiment, T-bars 904 are coupled such that every two T-bars, e.g., T-bars 904a, is coupled by a thread, e.g., thread 907a. Thread 907a is configured to enable T-bars 904a to be tensioned together and locked against tissue 940. Locking T-bars 904a enables tissue 940 to be bunched or slightly gathered, thereby effectively constraining the size, e.g., arc length, of mitral valve 916 by reducing the an arc length associated with tissue 940. In other words, the presence of T-bars 904 which cooperate with thread 907 to function substantially as sutures, allows the size of a gap 908 between an anterior leaflet 920 and a posterior leaflet 918 to be reduced and, further, to be substantially prevented from increasing. As will be appreciated by those skilled in the art, over time, scar tissue (not shown) may form over pledgets 905 and T-bars 904.

Generally, the number of T-bars 904 used to locally bunch or gather tissue 940 may be widely varied. For instance, when substantially only a small, localized regurgitant jet occurs in mitral valve 916, only a small number of T-bars 904 may be implemented in proximity to the regurgitant jet. Alternatively, when the size of gap 908 is significant, and there is a relatively large amount of mitral valve leakage, then a relatively large number of T-bars 904 and, hence, pledgets 905 may be used to reduce the size of gap 908 by reducing the arc length of mitral valve 916. Some pledgets 905 may be arranged to at least partially overlap. To correct for a regurgitant jet that is centralized to only one section of mitral valve 916, T-bars 904 may be implemented as plicating elements near the regurgitant jet, and as reinforcing elements away from the regurgitant jet, e.g., to prevent progression of mitral valve disease from causing a substantial gap to eventually form.

Figure 9B:
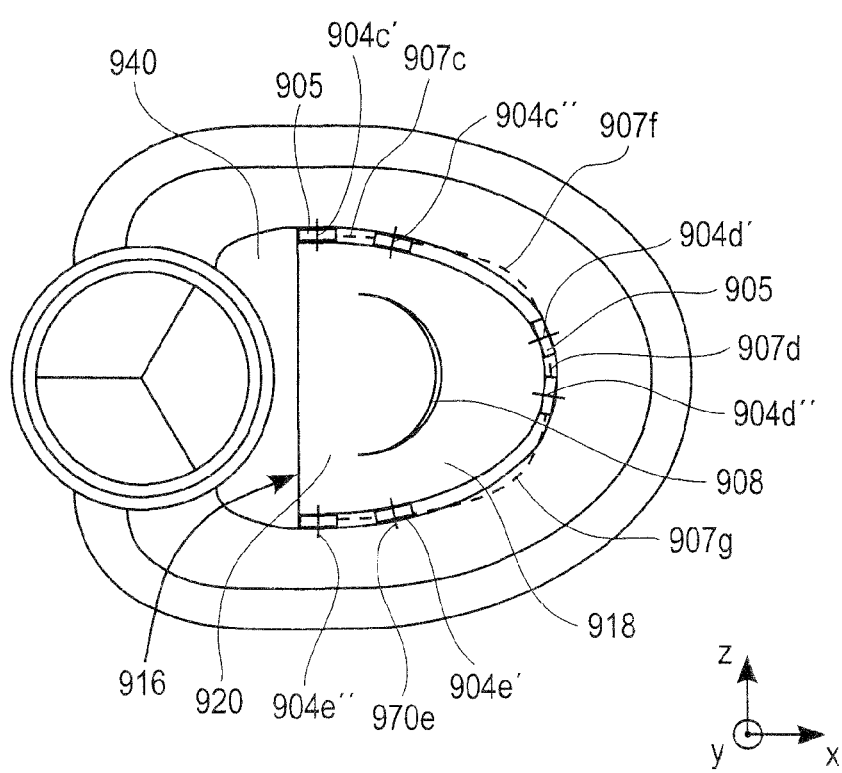
FIG. 9b is a cut-away top-view representation of a left ventricle of the heart in which local plication suture structures which are coupled have been implanted in accordance with an embodiment of the present invention.

While the coupling of two T-bars 904a with thread 907a has been described, it should be understood that the number of T-bars 904 coupled by a thread or threads 907 may vary. For example, if multiple T-bars 904 are coupled by multiple threads 907, then it may be possible to gather more fibrous tissue using fewer total T-bars 904. With reference to FIG. 9b, the use of multiple T-bars 904 which are coupled by multiple threads 907 will be described. T-bars 904c are coupled by a thread 907c, while T-bars 904d are coupled by a thread 907c. Similarly, T-bars 904e are coupled by a thread 907e. T-bar 904d' is further coupled by a thread 907f to T-bar 904c", and T-bars 904d" is also coupled by a thread 907g to T-bar 904e'. As will be discussed below, threads 907 enable T-bars 904 to be pulled against pledgets 905 and, hence, tissue 940. Such coupling of T-bars 904 enables plications in tissue 940 to be made between T-bars 904c, between T-bars 904d, and between T-bars 904e, while allowing tissue to be at least somewhat gathered between T-bar 904c" and T-bar 904d', and between T-bar 904d" and T-bar 904e'.

Figures 10A, 10B:
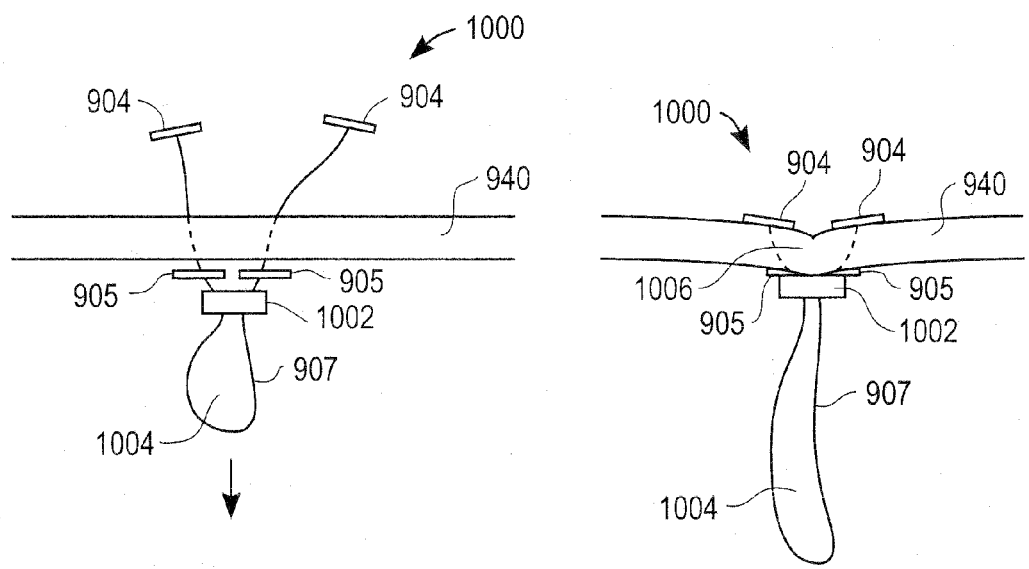
FIG. 10a is a representation of a suture structure after T-bars have been introduced to an atrial side of a mitral valve through fibrous tissue near the mitral valve in accordance with an embodiment of the present invention.
FIG. 10b is a representation of the suture structure of FIG. 10a after the T-bars have been engaged to the fibrous tissue in accordance with an embodiment of the present invention.

In general, the configurations of suture structures which include T-bars 904 and threads 907 may vary. One embodiment of a suitable suture structure is shown in FIGS. 10a and 10b. FIGS. 10a and 10b are representations of a suture structure after T-bars have been introduced to an atrial side of fibrous tissue near a mitral valve in accordance with an embodiment of the present invention. For purposes of illustration, it should be understood that the elements and structures represented in FIGS. 10a and 10b, as well as substantially all other figures, have not been drawn to scale. A suture structure 1000 includes T-bars 904, or reinforcing elements, that are coupled to thread 907 such that when thread 907 is pulled, T-bars 904 effectively push against tissue 940. As shown in FIG. 10b, pulling on thread 907 and pushing on a locking element 1002 causes locking element 1002 to contact a ventricular side of tissue 940 and to effectively hold T-bars 904 against tissue 940. Specifically, pulling on a loop 1004 of thread 907 while pushing on locking element 1002 tightens T-bars 904 against tissue 940 such that a plication 1006 may be formed in tissue 940 when locking element 1002 locks into position to lock T-bars 904 into place.

Pledgets 905, as will be appreciated by those skilled in the art, may serve as plication anchors for T-bars 904 which essentially function as sutures. That is, pledgets 905 may prevent T-bars 904 from cutting through tissue 940. In general, the configuration of pledgets 905 may vary widely. For example, pledgets 905 may have a substantially tubular form, and may be formed from a material such as surgical, e.g., Dacron, mesh. However, it should be appreciated that pledgets 905 may be formed in substantially any shape and from substantially any material which promotes or supports the growth of scar tissue therethrough. Suitable materials include, but are not limited to silk and substantially any biocompatible porous or fibrous material.

Locking element 1002 may be a one-way locking element, e.g., an element which may not be easily unlocked once it is locked, that is formed from a biocompatible polymer. The configuration of a locking element 1002 may be widely varied. Alternative configurations of locking element 1002 will be described below with respect to FIG. 11 and FIGS. 12a-c. In order to engage locking element 1002 against pledgets 905, a catheter which is used to deliver T-bars 904 may be used to push locking element 1002 into a locked position. A catheter which delivers T-bars 904 and may also be used to engage locking element 1002 will be discussed below with reference to FIGS. 13a-c.

Like locking element 1002, T-bars 904 may also be formed from a biocompatible polymer. Thread 907, which may be coupled to T-bars 904 through tying T-bars 904 to thread 907 or molding T-bars 904 over thread 907, may be formed from substantially any material which is typically used to form sutures. Suitable materials include, but are not limited to, silk, prolene, braided Dacron, and polytetrafluoroethylene (PTFE, or GoreTex).

Figure 11:
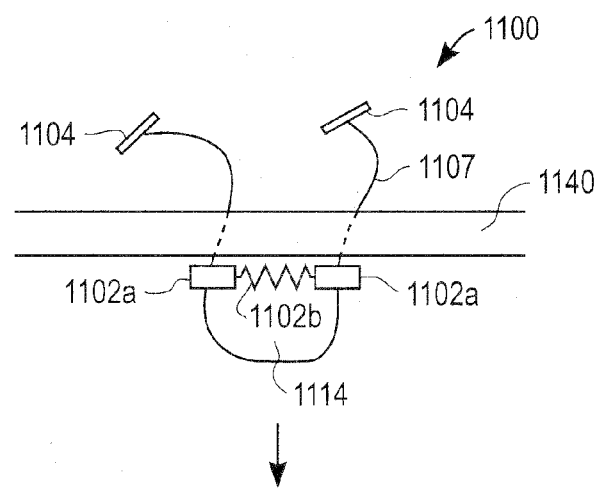
FIG. 11 is a representation of a suture structure which includes a locking element with a spring in accordance with an embodiment of the present invention.

As mentioned above, the configuration of locking element 1002 may vary. For example, a locking element may include a spring element as shown in FIG. 11. A suture structure 1100 include T-bars 1104, a thread 1107, and a locking element 1102. For ease of illustration, the elements of suture structure 1100 have not been drawn to scale. Although suture structure 1100 is not illustrated as including a pledget, it should be appreciated that suture structure 1100 may include a pledget or pledgets which serve as reinforcing elements which generally support the growth of scar tissue.

Locking element 1102 includes solid elements 1102a and a spring element 1102b. Although solid elements 1102a may be formed from a biocompatible polymer, solid elements 1102a may also be formed from material which is typically used to form pledgets. Spring element 1102b is arranged to be held in an extended position, as shown, while a loop 1114 in thread 1107 is pulled on. Once T-bars 1104 are in contact with tissue 1140, solid elements 1102a may come into contact with tissue 1140, and spring element 1102b may contract to create a spring force that pulls solid elements 1102a toward each other. In other words, once T-bars 1104 are properly positioned against tissue 1140, locking element 1102 may be locked to form a plication or local bunching of tissue 1140.

Figure 12A:
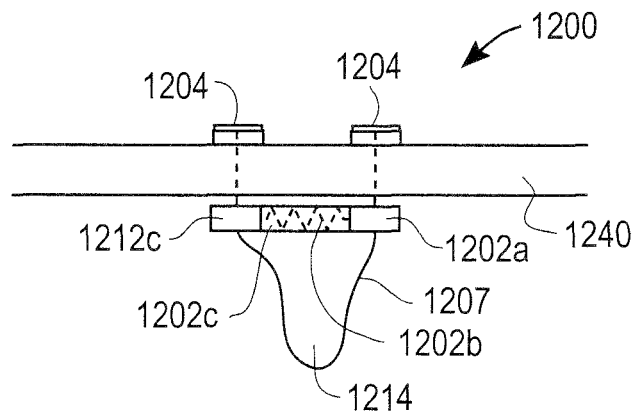
FIG. 12a is a representation of a suture structure which includes a locking element with a resorbable component in accordance with an embodiment of the present invention.
Figure 12B:
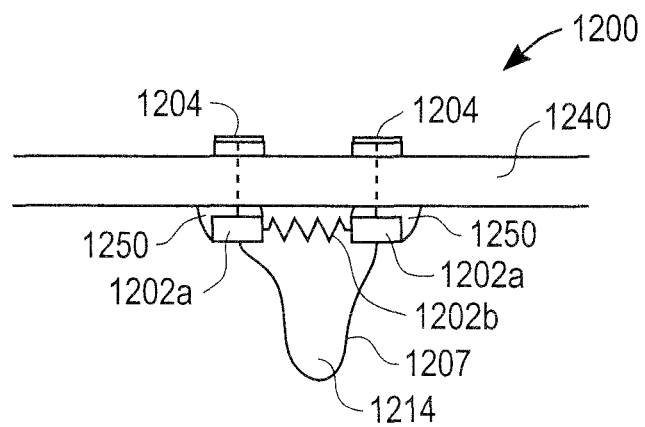
FIG. 12b is a representation of the suture structure of FIG. 12a after the resorbable component has degraded in accordance with an embodiment of the present invention.
Figure 12C:
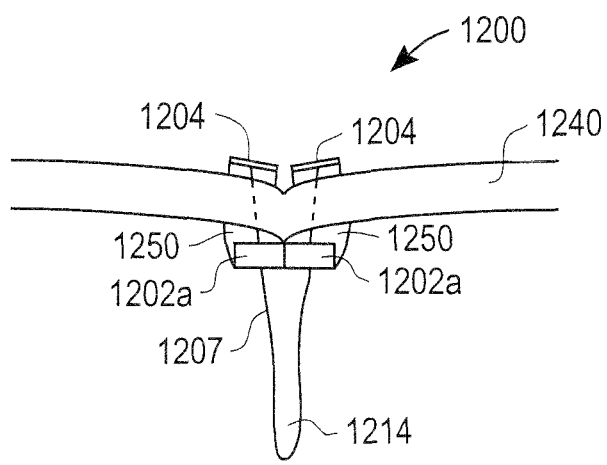
FIG. 12c is a representation of the suture structure of FIG. 12b after a plication has been created in accordance with an embodiment of the present invention.

In one embodiment, the formation of scar tissue on the fibrous tissue which is in proximity to a mitral valve may be promoted before a plication is formed, or before the fibrous tissue is gathered to compensate for mitral valve insufficiency. With reference to FIGS. 12a-c, a locking element which promotes the growth of scar tissue before a plication is formed will be described in accordance with an embodiment of the present invention. As shown in FIG. 12a, a suture structure 1200, which is not drawn to scale, includes a locking element 1204, a thread 1207, and T-bars 1204. Locking element 1204, which includes solid elements 1202a, a spring element 1202b, and a resorbable polymer overmold 1202c formed over spring element 1202b is coupled to thread 1207 on a ventricular side of tissue 1240.

Overmold 1202c, which may be formed from a resorbable lactide polymer such as PURASORB, which is available from PURAC America of Lincolnshire, Ill., is formed over spring element 1202b while spring element 1202b is in an extended position. Overmold 1202c is arranged to remain intact while scar tissue 1250 forms over solid elements 1202a. In one embodiment, in order to facilitate the formation of scar tissue, solid elements 1202a may be formed from material that is porous or fibrous, e.g., "pledget material."

Once scar tissue is formed over solid elements 1202a, overmold 1202c breaks down, e.g., degrades, to expose spring element 1202b, as shown in FIG. 12b. As will be understood by one of skill in the art, the chemical composition of overmold 1202c may be tuned such that the amount of time that elapses before overmold 1202c breaks down may be controlled, e.g., controlled to break down after a desired amount of scar tissue is expected to be formed. Hence, once overmold 1202c breaks down, and spring element 1202b is allowed to contract, as shown in FIG. 12c, enough scar tissue 1250 will generally have formed over solid elements 1202a to effectively bond solid elements 1202a against tissue 1240 to allow for the formation of a relatively strong plication or gathering of tissue 1240.

While a loop 1214 of thread 1207 may be allowed to remain extended into a left ventricle of a heart, thread 1207 may be cut, i.e., loop 1214 may be effectively removed, to reduce the amount of loose thread 1207 in the heart. Alternatively, loose thread 1207 may effectively be eliminated by gathering thread 1207 around a cylindrical arrangement (not shown) positioned over locking element 1202. That is, a spool or similar element may be included as a part of suture structure 1200 to enable loose thread 1207 to either be gathered within the spool or gathered around the exterior of the spool.

The use of overmold 1202c enables anchoring forces which hold T-bars 1204 and locking element 1202 in position to be relatively low, as substantially no significant forces act on tissue 1240 until after scar tissue or tissue ingrowth is created. Once scar tissue is created, and overmold 1202c has degraded, then spring 1202b compresses. The anchoring forces generated at this time may be relatively high. However, as scar tissue has been created, the likelihood that T-bars 1204 cut into tissue 1240 at this time is generally relatively low.

As mentioned above, catheters may be used to deliver suture structures into a heart, and to engage the suture structures to tissue around the mitral valve of the heart. One embodiment of a suture structure delivery catheter which is suitable for use in a catheter-based annuloplasty that uses local plications will be described with respect to FIG. 13a. A delivery catheter 1300 may be positioned over a guide wire, e.g., guide wire 802 as shown in FIG. 8, which serves as a track to enable delivery catheter 1300 to be delivered in the gutter of a heart. It should be appreciated that the elements of delivery catheter 1302 have not been drawn to scale. Within delivery catheter 1300 is a wire 1308 which carries T-bars 1304 of a suture structure. In one embodiment, T-bars 1300 are coupled to a thread 1307 and a locking element 1300 to form the suture structure. Typically, a pointed or sharpened end 1311 of wire 1308 is configured to penetrate tissue (not shown), e.g., fibrous tissue of the heart near a mitral valve. Once end 1311 and T-bar 1304 are located above fibrous tissue, e.g., on an atrial side of a mitral valve, wire 1308 may be retracted a repositioned. After wire 1308 is repositioned, end 1311 may once again penetrate tissue to effectively deposit T-bar 1304 over tissue on the atrial side of the mitral valve.

Wire 1308 or, more specifically, end 1311 may be used to pull thread 1307 and to push locking element 1302 into position against tissue near the mitral valve. By way of example, end 1311 may pull on thread 1307 until T-bars 1304 contact the tissue. Then, end 1311 may be used to lock locking element 1302 against the tissue and, as a result, create a plication in the tissue to effectively shrink the annulus of the mitral valve.

In order to create additional plications, wire 1308 and, in one embodiment, delivery catheter 1300, may be retracted entirely out of a patient to enable additional T-bars to be loaded onto wire 1308. Once additional T-bars are positioned on wire 1308, wire 1308 may be reinserted into delivery catheter 1300, and delivery catheter 1300 may be used to enable another plication to be created in the tissue which is located near the mitral valve.

Figure 13B:
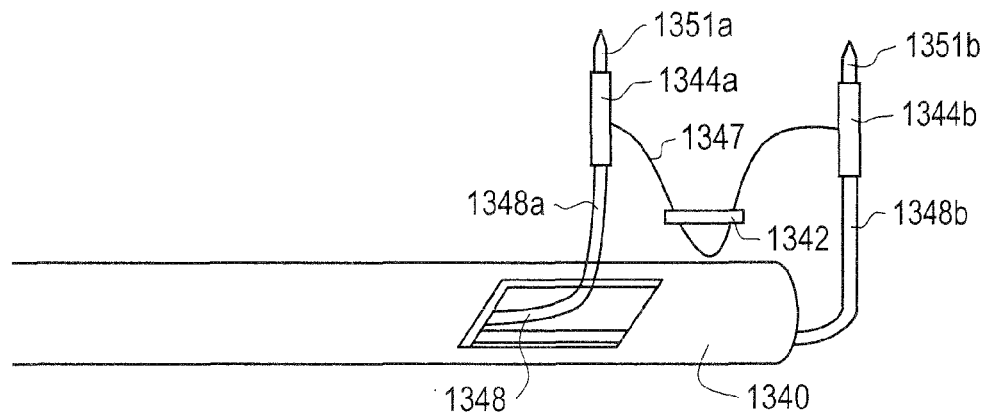
FIG. 13b is a representation of a second catheter which is suitable for use in delivering and implementing a suture structure in accordance with an embodiment of the present invention.

FIG. 13b is a representation of a second catheter which is suitable for delivering a suture structure in accordance with an embodiment of the present invention. A catheter 1340, which is not drawn to scale and which may include a lumen (not shown) that is arranged to be inserted over a guide wire, includes two wires 1348 which are arranged to cooperate to carry a suture structure. As shown, wire 1348a carries a T-bar 1344a while wire 1348b carries a T-bar 1344b which are coupled by a thread 1347 and, together with a locking element 1342, form a suture structure. Tips 1351 of wires 1348 pass through tissue near a mitral valve to deposit T-bars 1344 above the mitral valve. Once T-bars 1344 are deposited, tips 1351 may be used to pull T-bars 1344 against the tissue, as well as to lock locking element 1342 against an opposite side of the tissue. By way of example, tip 1351b may be configured to pull on thread 1347 while tip 1351a pushes against locking element 1342.

Figure 13C:
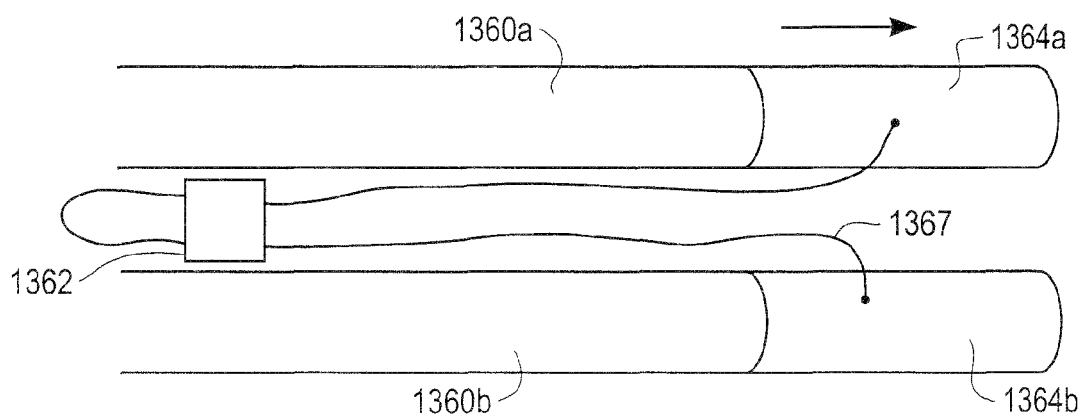
FIG. 13c is a representation of a third catheter assembly which is suitable for use in delivering and implementing a suture structure in accordance with an embodiment of the present invention.

With reference to FIG. 13c, a catheter arrangement which may deploy T-bars from its tip will be described in accordance with an embodiment of the present invention. A catheter arrangement 1360 includes two catheters which each carry a T-bar 1364. It should be appreciated that the elements of FIG. 13c have not been drawn to scale for ease of illustration. Specifically, catheter 1360a carries T-bar 1364a at its tip, while catheter 1360b carries T-bar 1364b at its tip. A thread 1367 couples T-bars 1364 together such that a locking element 1362 through which thread 1367 passes may lock T-bars 1364 substantially against tissue of a heart.

In one embodiment, catheter arrangement 1360 may require the use of two guide wires to guide each of catheter 1360a and catheter 1360b into the gutter of the heart. Alternatively, catheter 1360a and catheter 1360b may be arranged such that both catheter 1360a and catheter 1360b may be guided through the gutter of the heart through the use of a single guide wire.

Catheter 1360a is configured to push T-bar 1364a through tissue near the mitral valve of the heart, and to release T-bar 1364a once T-bar 1364a is located on an atrial side of the mitral valve. Similarly, catheter 1360b is configured to push T-bar 1364b through the tissue, and to release T-bar 1364b. T-bars 1364 may be released, for example, when heat is applied to a dielectric associated with catheters 1360 that causes T-bars 1364 to be effectively snapped off. Alternatively, a mechanical mechanism (not shown) that engages T-bars 1364 to catheters 1360 may be disengaged to release T-bars 1354. Once T-bars 1364 are positioned on the atrial side of the mitral valve, catheter 1360 may be used to pull on thread 1367 and to push on locking element 1362.

Figure 14A:
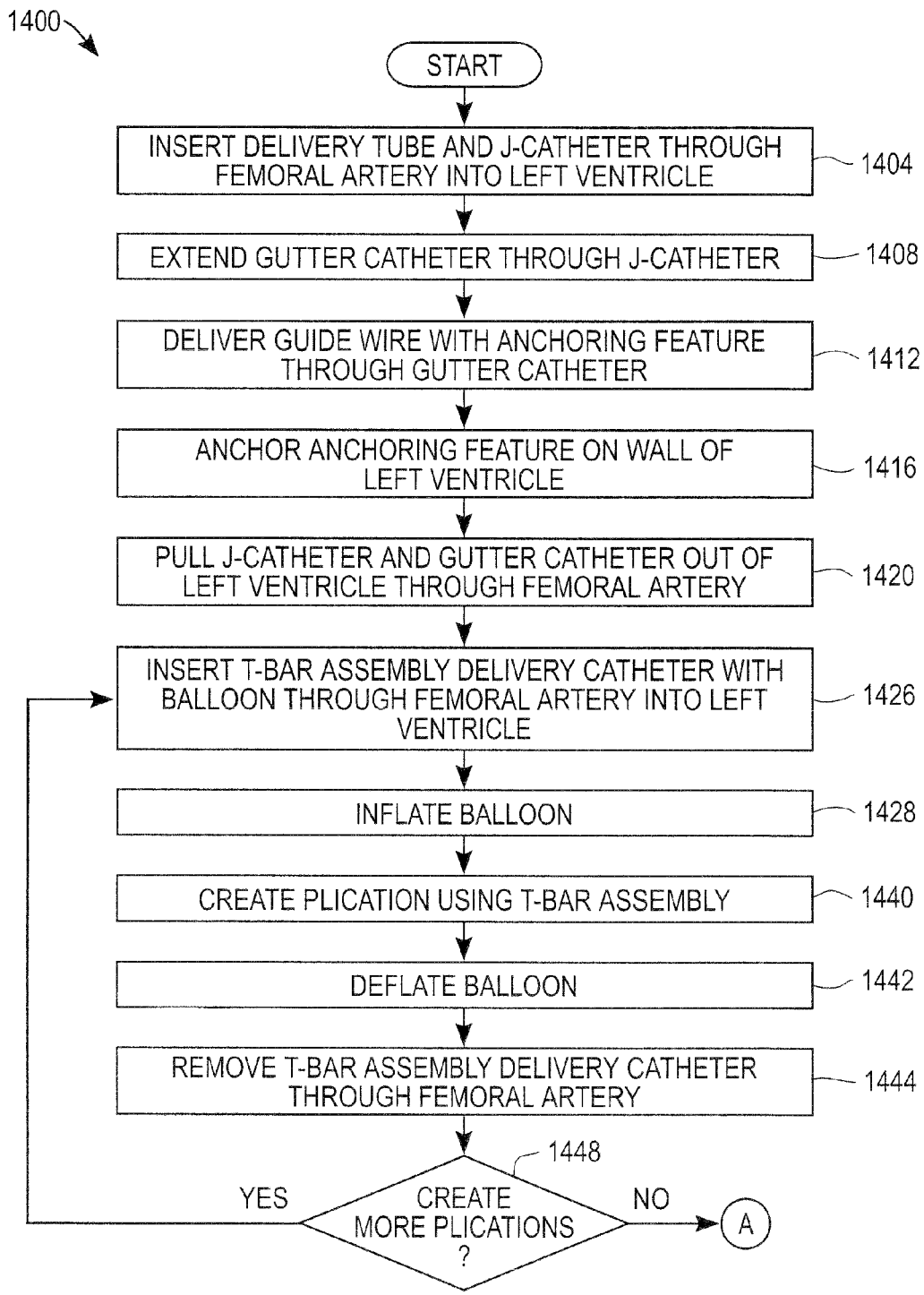
FIGS. 14a and 14b are a process flow diagram which illustrates the steps associated with one method of performing annuloplasty using a suture structure and a catheter in accordance with an embodiment of the present invention.
Figure 14B:
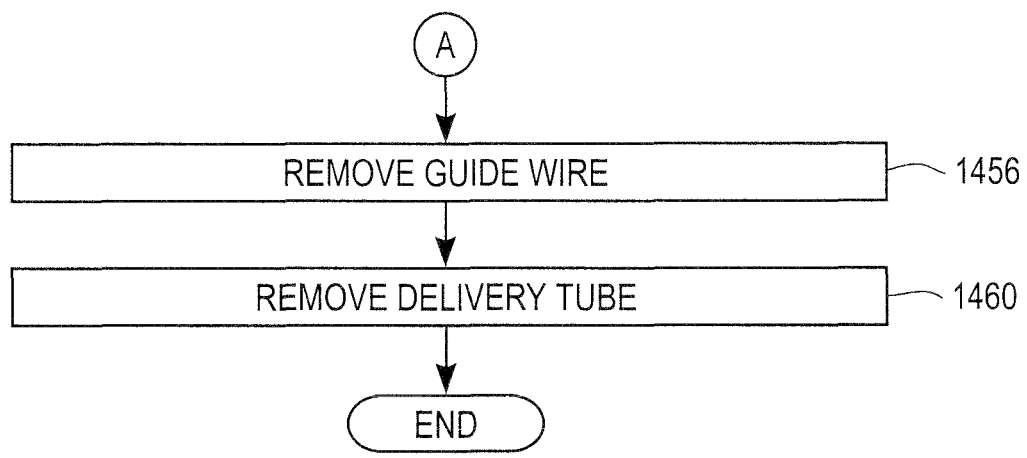

With reference to FIGS. 14a and 14b, the performance of an annuloplasty procedure using a catheter-based system which implants suture structures in tissue near a mitral valve will be described in accordance with an embodiment of the present invention. Once a patient is prepared, e.g., sedated, an annuloplasty procedure 1400 may begin with the insertion of a delivery tube and a J-catheter into the left ventricle of the heart of the patient. The delivery tube and the J-catheter may be inserted into the body of the patient through the femoral artery, and threaded through the femoral artery and the aorta into the left ventricle of the heart. Generally, the J-catheter is positioned within the delivery tube. One embodiment of the delivery tube and a J-catheter were described above with respect to FIGS. 6a and 6b. As will be appreciated by those skilled in the art, the delivery tube and the J-catheter are typically each threaded through the aortic valve to reach the left ventricle.

Once the delivery tube and the J-catheter are positioned within the left ventricle, a gutter catheter may be extended through the J-catheter in step 1408. As was discussed above with reference to FIGS. 7a-c, the gutter catheter is arranged to effectively run against a gutter of the wall of the left ventricle substantially immediately under the mitral valve. Specifically, the gutter catheter may be positioned in the space in the left ventricle between the mitral valve and the musculi papillares, or papillary muscles. The gutter catheter often has a tip that is steerable and flexible. In one embodiment, the tip of the gutter catheter may be coupled to an inflatable balloon. The J-catheter serves, among other purposes, the purpose of allowing the gutter catheter to be initially oriented in a proper direction such that the gutter catheter may be positioned along the wall of the left ventricle.

In step 1412, a guide wire with an anchoring feature may be delivered through the gutter catheter, e.g., through a lumen or opening in the gutter catheter. The guide wire is delivered through the gutter catheter such that it follows the contour of the gutter catheter against the wall of the left ventricle. After the guide wire is delivered, the anchoring feature of the guide wire is anchored on the wall of the left ventricle in step 1416. Anchoring the guide wire, or otherwise implanting the guide wire, on the wall of the left ventricle enables the guide wire to maintain its position within the left ventricle.

The J-catheter and the gutter catheter are pulled out of the left ventricle through the femoral artery in step 1420, leaving the guide wire anchored within the left ventricle, as was discussed above with respect to FIG. 8. A T-bar assembly delivery catheter which carries a T-bar assembly is then inserted through the femoral artery into the left ventricle over the guide wire in step 1436. In one embodiment, the T-bar assembly delivery catheter carries an uninflated balloon.

After the T-bar assembly delivery catheter is inserted into the left ventricle, the balloon is inflated in step 1428. Inflating the balloon, e.g., an elastomeric balloon, at a relatively modest pressure using, for example, an air supply coupled to the balloon through the T-bar assembly delivery catheter, serves to enable substantially any catheter which uses the guide wire as a track to be pressed up against the fibrous tissue around the mitral valve. Generally, the inflated balloon substantially occupies the space between the mitral valve and the papillary muscles. In one embodiment, more than one balloon may be inflated in the left ventricle.

Once the balloon is inflated in step 1428. The T-bar assembly delivery catheter effectively delivers T-bars, or similar mechanisms, pledgets, and thread which are arranged to attach or otherwise couple with an annulus of the mitral valve, e.g., the fibrous tissue of the skeleton around the mitral valve, to create plications. Suitable catheters were described above with respect to FIGS. 13a-c. In step 1440, a plication is created using the T-bar assembly in substantially any suitable tissue near the mitral valve. For example, a plication may be created by essentially forcing T-bars through the tissue, then locking the T-bars against the tissue using a locking mechanism of the T-bar assembly. Specifically, the plication or bunching of tissue may be created by extending sharpened wires which carry elements such as T-bars through the tissue, then retracting the sharpened wires, and pulling the T-bars into place. Positioning the T-bars, and locking the locking mechanism causes the tissue between the T-bars and the locking mechanism may bunch together.

Once the plication is created in step 1440, the balloon is generally deflated in step 1442. The T-bar assembly delivery catheter may then be removed through the femoral artery in step 1444. A determination is made in step 1448 after the T-bar assembly delivery catheter is removed as to whether additional plications are to be created. If it is determined that additional plications are to be created, then process flow returns to step 1436 in which the T-bar assembly delivery catheter, which carries a T-bar assembly or suture structure, is reinserted into the femoral artery.

Alternatively, if it is determined in step 1448 that there are no more plications to be created, then process flow proceeds to step 1456 in which the guide wire may be removed. After the guide wire is removed, the delivery tube may be removed in step 1460. Once the delivery tube is removed, the annuloplasty procedure is completed.

Figure 15:
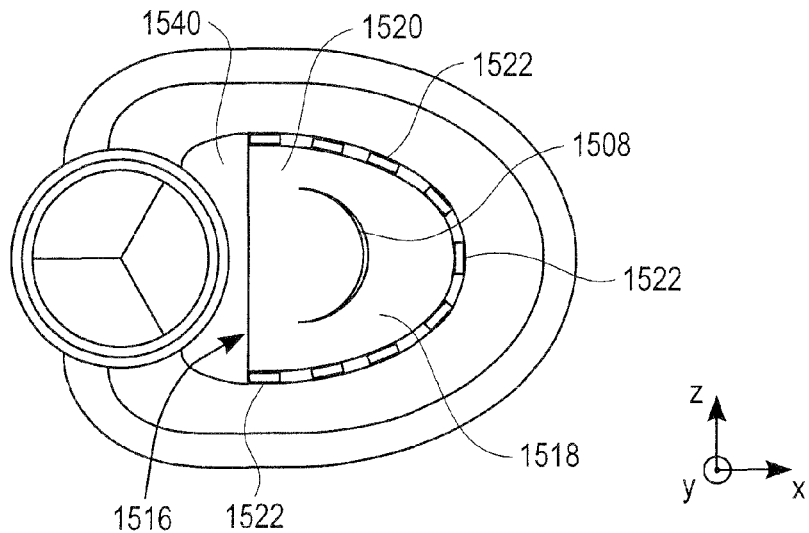
FIG. 15 is a cut-away top-view representation of a left ventricle of the heart in which local plication elements have been implanted in accordance with an embodiment of the present invention.

In lieu of using suture structures such as T-bar assemblies to create local plications, other elements may also be used to create local plications in fibrous tissue near the mitral valve during an annuloplasty procedure. FIG. 15 is a cut-away top view representation of a left side of a heart in which local plications have been created using individual, discrete elements in accordance with an embodiment of the present invention. Local plication elements 1522 are effectively implanted in fibrous tissue 1540 around portions of a mitral valve 1516 in order to reduce the size of a gap 1508 between an anterior leaflet 1520 and a posterior leaflet 1518, e.g., to reduce the arc length associated with posterior leaflet 1518. Local plication elements 1522 are arranged to gather sections of tissue 1540 to create local plications. The local plications created by local plication elements 1522, which are generally mechanical elements, reduce the size of the mitral valve annulus and, hence, reduce the size of gap 1508. As will be understood by those skilled in the art, over time, scar tissue may grow around or over local plication elements 1522.

Figure 16A:
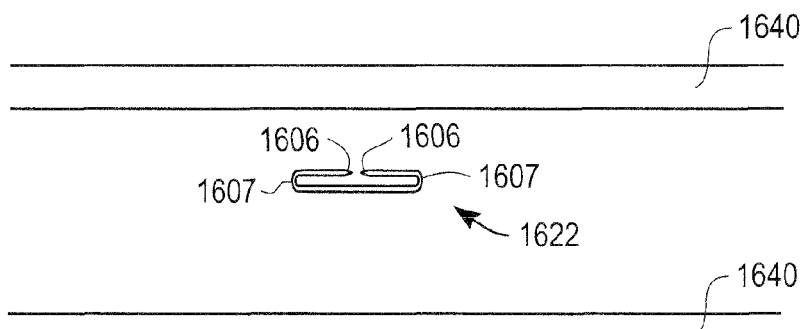
FIG. 16a is a representation of a local plication element which has spring-like characteristics in accordance with an embodiment of the present invention.
Figure 16B:
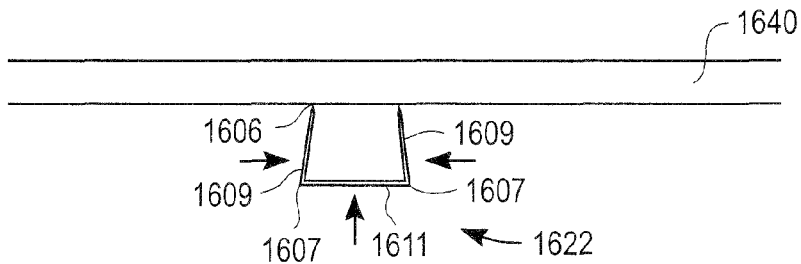
FIG. 16b is a representation of the local plication element of FIG. 16a after forces have been applied to open the local plication element in accordance with an embodiment of the present invention.
Figure 16C:
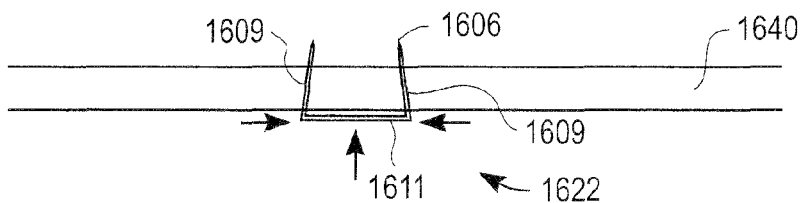
FIG. 16c is a representation of the local plication element of FIG. 16b after tips of the local plication element pierce through tissue in accordance with an embodiment of the present invention.
Figure 16D:
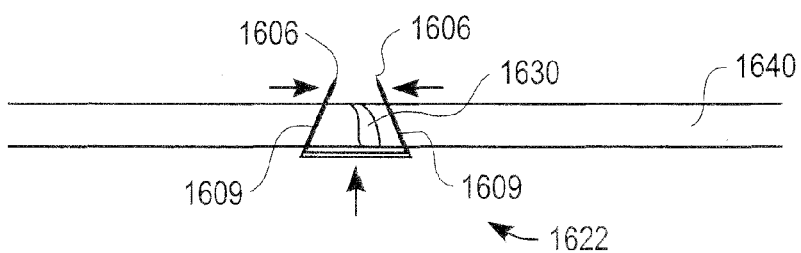
FIG. 16d is a representation of the local plication element of FIG. 16c after the tips of the local plication element engage the tissue to form a local plication in accordance with an embodiment of the present invention.

The configuration of local plication elements 1522 may be widely varied. For example, local plication elements 1522 may be metallic elements which have spring-like characteristics, or deformable metallic elements which have shape memory characteristics. Alternatively, each local plication element 1522 may be formed from separate pieces which may be physically locked together to form a plication. With reference to FIGS. 16a-d, one embodiment of a local plication element which has spring-like characteristics will be described in accordance with an embodiment of the present invention. A local plication element 1622 may be delivered to a ventricular side, or bottom side, of tissue 1640 which is located near a mitral valve. When delivered, as for example through a catheter, element 1622 is in a substantially folded, closed orientation, as shown in FIG. 16a. In other words, element 1622 is in a closed configuration that facilitates the delivery of element 1622 through a catheter. After an initial compressive force is applied at corners 1607 of element 1622, sides or tines 1609 of element 1622 may unfold or open. As tines 1609 open, tips 1606 of tines 1609 may be pressed against tissue 1640, as shown in FIG. 16b. The application of compressive force to tines 1609, as well as a pushing force to a bottom 1611 of element 1622, allows tips 1606 and, hence, tines 1609 to grab tissue 1640 as tips 1606 push through tissue 1640, as shown in FIG. 16c. The closing of tines 1609, due to compressive forces applied to tines 1609, causes tissue 1640 to be gathered between tines 1609 and, as a result, causes a plication 1630 to be formed, as shown in FIG. 16d. In one embodiment, the catheter (not shown) that delivers element 1622 may be used to apply forces to element 1622.

As mentioned above, elements used to create local plications may be created from shape memory materials. The use of a shape memory material to create a plication element allows the plication element to be self-locking. FIG. 17a is a representation of one plication element which is formed from a shape memory material in accordance with an embodiment of the present invention. A clip 1704, which may be formed from a shape memory material, i.e., an alloy of nickel and titanium, is arranged to be in an expanded state or open state when it is introduced, e.g., by a catheter, into the gutter of the left ventricle. Typically, holding clip 1704 in an expanded state involves applying force to clip 1704. In one embodiment, a catheter may hold sides 1708 of clip 1704 to maintain clip 1704 in an expanded state.

Once tips 1706 of clip 1704 are pushed through the fibrous tissue near the mitral valve of the heart such that tips 1706 are positioned on an atrial side of the mitral valve, force may be removed from clip 1704. Since clip 1704 is formed from a shape memory material, once force is removed, clip 1704 forms itself into its "rest" state of shape, as shown in FIG. 17b. In its rest state or preferred state, clip 1704 is arranged to gather tissue in an opening 1712 defined by clip 1704. That is, the default state of clip 1704 is a closed configuration which is effective to bunch tissue to create a local plication.

Figure 18A:
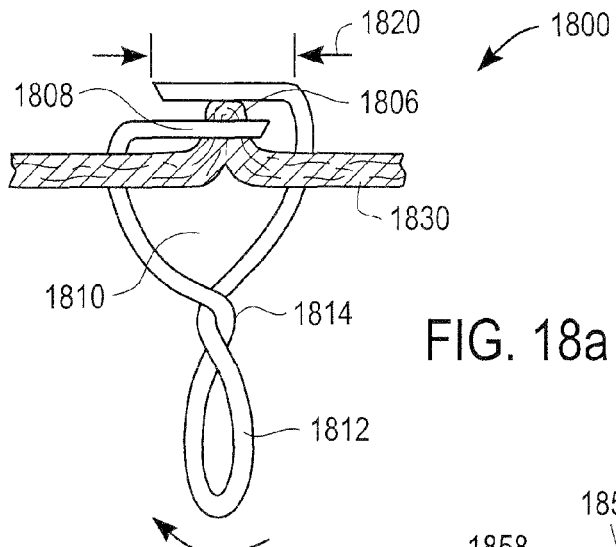
FIG. 18a is a representation of a first self-locking clip which is suitable for use in forming a local plication in accordance with an embodiment of the present invention.
Figure 18B:
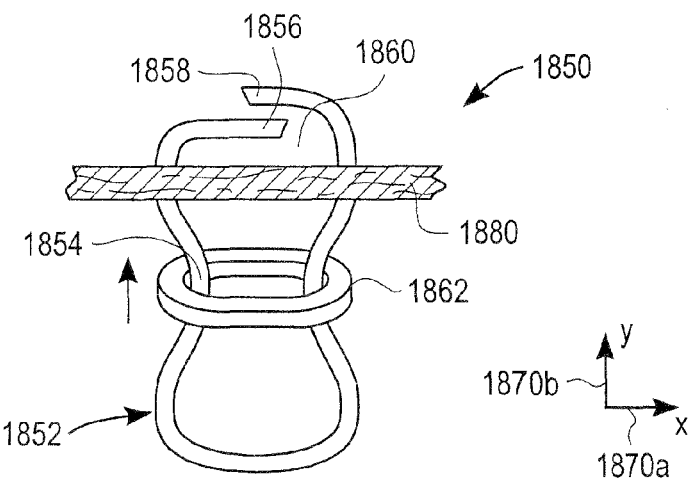
FIG. 18b is a representation of a second self-locking clip which is suitable for use in forming a local plication in accordance with an embodiment of the present invention.

Another discrete self-locking plication element which is suitable for creating a local plication is a clip which may twist from an open position to a closed, or engaged position, once force applied to hold the clip in an open position is removed. FIG. 18a is a representation of another self-locking plication element shown in a closed position in accordance with an embodiment of the present invention. A clip element 1800, which may be formed from a material such as stainless steel or a shape memory material, is preloaded such that once tissue 1830 is positioned in a gap 1810 between a tine 1806 and a tine 1808, clip element 1800 may return to a state which causes tissue 1830 to be pinched within a gap or space 1810.

Tine 1806 and tine 1808 first pierce tissue 1830, e.g., the tissue of an annulus of a mitral valve. As tine 1806 and tine 1808 are drawn together to create a plication, thereby reducing the size of gap 1810 by reducing a distance 1820, a bottom portion 1812 of clip element 1800 twists, as for example in a quarter turn, effectively by virtue of shape memory characteristics of clip element 1800. Thus, an effective lock that holds tine 1806 and tine 1808 in a closed position such that tissue 1830 is gathered to form a local plication results.

In lieu of a preloaded clip element, a clip element may include a lock mechanism which engages when force is applied. FIG. 18*a* is a representation of a self-locking plication element which includes a sliding lock in accordance with an embodiment of the present invention. A clip element 1850 includes a body 1852 and a slider 1862 which is arranged to slide over at least a portion of body 1852. Clip element 1850, which may be formed from a material such as stainless steel or a shape memory alloy, includes a tip 1856 and a tip 1858 which are substantially separated by a gap 1856 when slider 1862 is in an unlocked position. As shown, slider 1862 is in an unlocked or open position when slider 1862 is positioned about a tapered neck 1854 of body 1852.

When clip element 1850 is delivered into a left ventricle, e.g., using a catheter, clip element 1850 is positioned within the left ventricle such that tip 1856 and tip 1858 are effectively pierced through fibrous tissue 1880 near the mitral valve. After tip 1856 and tip 1858 are positioned substantially on an atrial side of tissue 1880, force may be applied to slider 1862 to move slider 1862 in a y-direction 1870*b* over body 1852. As slider moves in y-direction 1870*b* away from tapered neck 1854, slider 1862 forces tip 1856 and tip 1858 together close gap 1860, i.e., tip 1856 and tip 1858 move towards each other in an x-direction 1870*a*. When tip 1856 and tip 1858 cooperate to close gap 1860, tissue 1880 is gathered within clip element 1850, thereby creating a local plication.

In one embodiment, when slider 1862 is in a closed position such that tip 1856 and tip 1858 cooperate to close gap 1856, slider 1862 may contact tissue 1880. Hence, in order to promote the growth of scar tissue over parts of clip element 1850 or, more specifically, slider 1862, at least a top surface of slider 1862 may be covered with a pledget material, e.g., a mesh which supports the growth of scar tissue therethrough.

Figure 19:
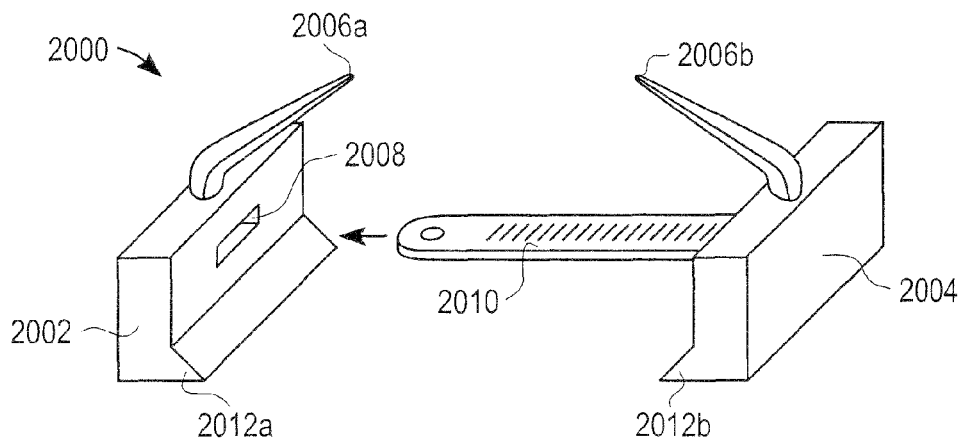
FIG. 19 is a representation of a plication-creating locking mechanism in accordance with an embodiment of the present invention.

Locking elements which create local plications may include elements which have two or more substantially separate pieces which lock together around tissue. An example of a locking element which includes two separate pieces is shown in FIG. 19. As shown in FIG. 19, a locking element 2000 may include a receiver piece 2002 and a locker piece 2004, which may generally be formed from substantially any suitable material, as for example a biocompatible plastic material. Receiver piece 2002 and locker piece 2004 each include a tine 2006. Tines 2006 are arranged to pierce and to engage tissue to create a local plication.

A cable tie portion 2010 of locker piece 2004 is configured to be drawn through an opening 2008 which engages cable tie portion 2010. Opening 2008 includes features (not shown) which allow cable tie portion 2010 to be pulled through opening 2008 and locked into position, and which prevent cable tie portion 2010 substantially from being pushed out of opening 2008. Cable tie portion 2010 is locked in opening 2008 when bevels 2012 come into contact and effectively force tines 2006 to clamp down. Once tines 2006 clamp down, and locker piece 2004 is locked against receiver piece 2002, a local plication is formed.

Figure 20A:
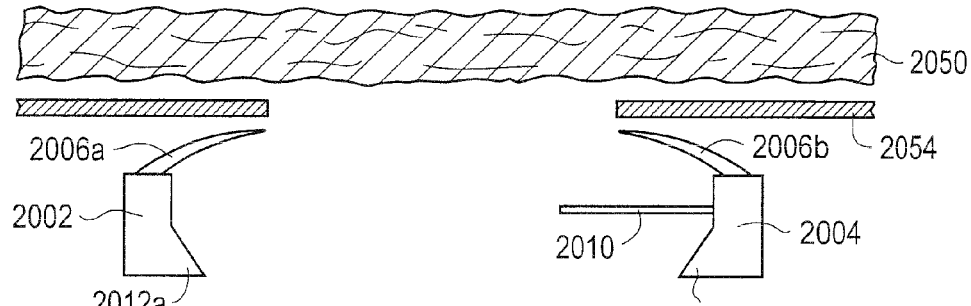
FIG. 20a is a representation of the plication-creating locking mechanism of FIG. 19 as provided within the left ventricle of a heart in accordance with an embodiment of the present invention.

The operation of locking element 2000 will be described with respect to FIGS. 20*a*-*d* in accordance with an embodiment of the present invention. As shown in FIG. 20*a*, receiver piece 2002 and locker piece 2004 may be delivered substantially beneath fibrous tissue 2050 near a mitral valve (not shown). Receiver piece 2002 and locker piece 2004 may be delivered using a catheter which includes a top surface 2054. Top surface 2054 of the catheter is arranged to apply force to tines 2006 such that tines 2006 remain in an effectively undeployed, e.g., partially bent or folded, position while being delivered by the catheter.

Figure 20B:
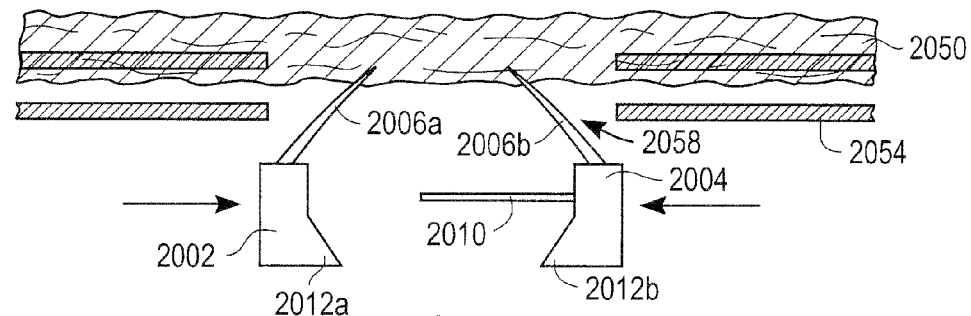
FIG. 20b is a representation of the plication-creating locking mechanism of FIG. 20a after forces have been applied to cause tines of the mechanism to contact tissue in accordance with an embodiment of the present invention.

Once receiver piece 2002 and locker piece 2004 are positioned under tissue 2050 near a location where a plication is to be formed, forces are applied to receiver piece 2002 and locker piece 2004 to push receiver piece 2002 and locker piece 2004 together and effectively through an opening 2058 in top surface 2054 of the catheter, as shown in FIG. 20*b*. The forces are typically applied by mechanisms (not shown) associated with the catheter. As tines 2006 pass through opening 2058, tines 2006 "open," or deploy in order to pierce tissue 2050.

Figure 20C:
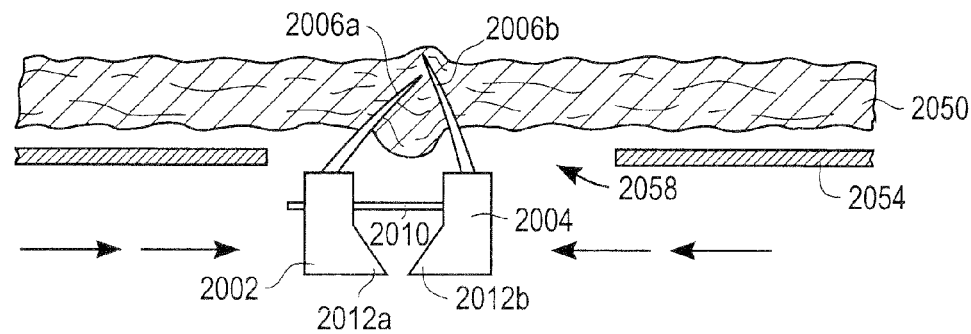
FIG. 20c is a representation of the plication-creating locking mechanism of FIG. 20b after tissue has been gathered between the tines of the mechanism in accordance with an embodiment of the present invention.
Figure 20D:
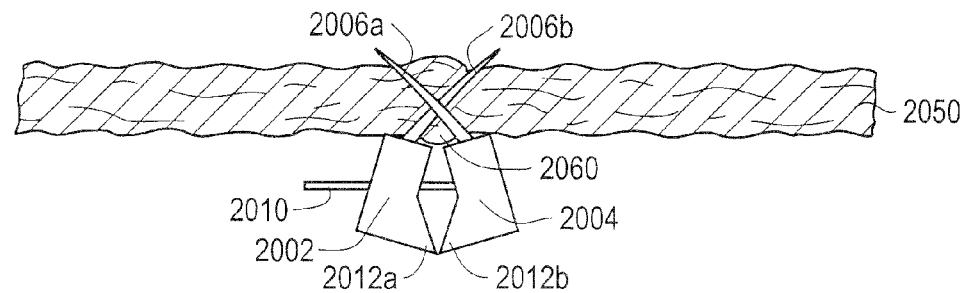
FIG. 20d is a representation of the plication-creating locking mechanism of FIG. 20c after a local plication has been formed in accordance with an embodiment of the present invention.

After piercing tissue 2050, tines 2006 continue to penetrate and to gather tissue 2050 while receiver piece 2002 and locker piece 2004 are pushed together. As receiver piece 2002 and locker piece 2004 are pushed together, cable tie portion 2010 is inserted into opening 2008 (shown in FIG. 19) of receiver portion 2002, as shown in FIG. 20*c*. Cable tie portion 2010 eventually locks with respect to opening 2008 when bevels 2012 come into contact. When bevels 2012 come into contact, tines 2006 close inwards, causing tissue 2050 to be captured, i.e., causing a local plication 2060 to be formed. Once a local plication is formed, and force is no longer required to push receiver piece 2002 and locker piece 2004 together, the catheter which delivered receiver piece 2002 and locker piece 2004 may be removed from the left ventricle.

Figure 21A:
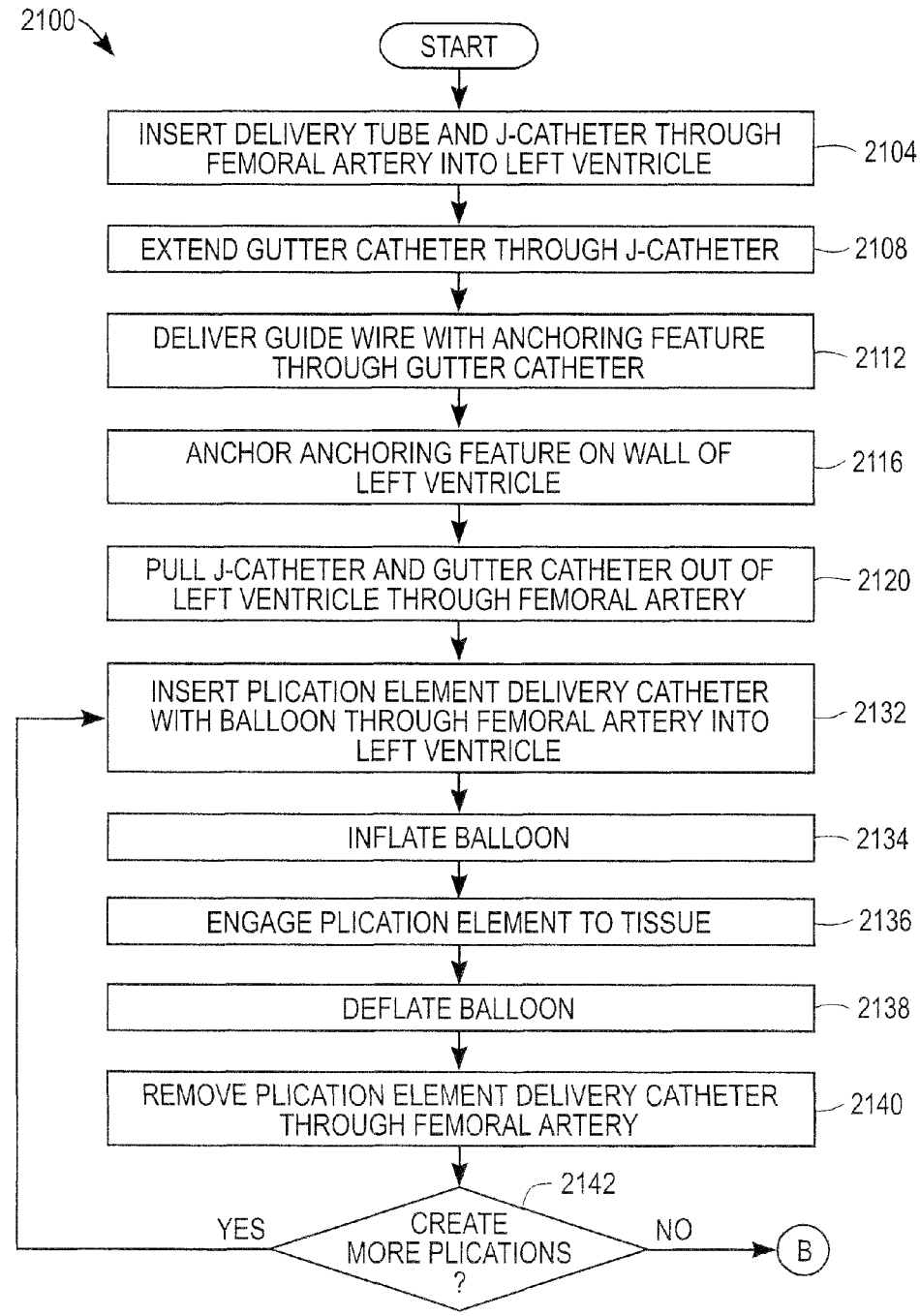
FIGS. 21a and 21b are a process flow diagram which illustrates the steps associated with one method of performing annuloplasty using a local plication element and a catheter in accordance with an embodiment of the present invention.
Figure 21B:
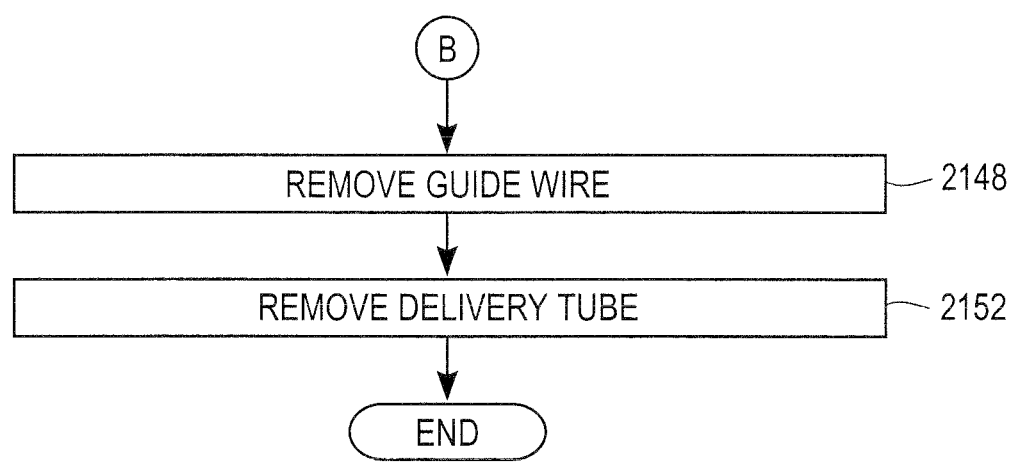

Referring next to FIGS. 21*a* and 21*b*, an annuloplasty procedure which uses a catheter-based system to create local plications in tissue near a mitral valve using discrete elements will be described in accordance with an embodiment of the present invention. After a patient is prepared, an annuloplasty procedure 2100 may begin with the insertion of a delivery tube and a J-catheter into the left ventricle of the heart of the patient in step 2104. Once the delivery tube and the J-catheter are positioned within the left ventricle, a gutter catheter may be extended through the J-catheter in step 2108. The gutter catheter, as described above, is arranged to effectively run against a gutter of the wall of the left ventricle, e.g., between the mitral valve and the papillary muscles. The gutter catheter often has a tip that is steerable and flexible.

In step 2112, a guide wire with an anchoring feature may be delivered through the gutter catheter, e.g., through a lumen or opening in the gutter catheter. The guide wire is delivered through the gutter catheter such that it follows the contour of the gutter catheter against the wall of the left ventricle. After the guide wire is delivered, the anchoring feature of the guide wire is anchored on the wall of the left ventricle in step 2116.

The J-catheter and the gutter catheter are pulled out of the left ventricle through the femoral artery in step 2120, leaving the guide wire anchored within the left ventricle, as was discussed above with respect to FIG. 8. A plication element delivery catheter which carries a plication element and, in one embodiment, is arranged to engage the plication element to the fibrous tissue around the mitral valve is inserted through the femoral artery into the left ventricle over the guide wire in step 2132. The plication element delivery catheter, in the described embodiment, is coupled to an uninflated balloon which is inflated in step 2134 to effectively allow the plication element delivery catheter to be positioned substantially directly under the fibrous tissue. Once the plication element delivery catheter is positioned in the left ventricle, e.g., over the guide wire in the gutter of the left ventricle, and the balloon is inflated, the plication element delivered by the delivery catheter is engaged to the fibrous tissue in step 2136. That is, the plication element is coupled to the fibrous tissue such that a local plication is formed in the fibrous tissue.

After the local plication is created in step 2136 by engaging tissue using the plication element, the balloon is deflated in step 2138. Upon deflating the balloon, the plication element delivery catheter may be removed through the femoral artery in step 2140. A determination is then made in step 2142 as to whether additional local plications are to be created. That is, it is determined if other plication elements are to be introduced into the left ventricle. If it is determined that additional local plications are to be created, process flow returns to step 2132 in which the plication element delivery catheter, which carries another plication element, is reinserted into the femoral artery.

Alternatively, if it is determined in step 2142 that there are no more local plications to be created, then the indication is that a sufficient number of local plications have already been created. Accordingly, the guide wire may be removed in step 2148, and the delivery tube may be removed in step 2152. After the delivery tube is removed, the annuloplasty procedure is completed.

Figure 22A:
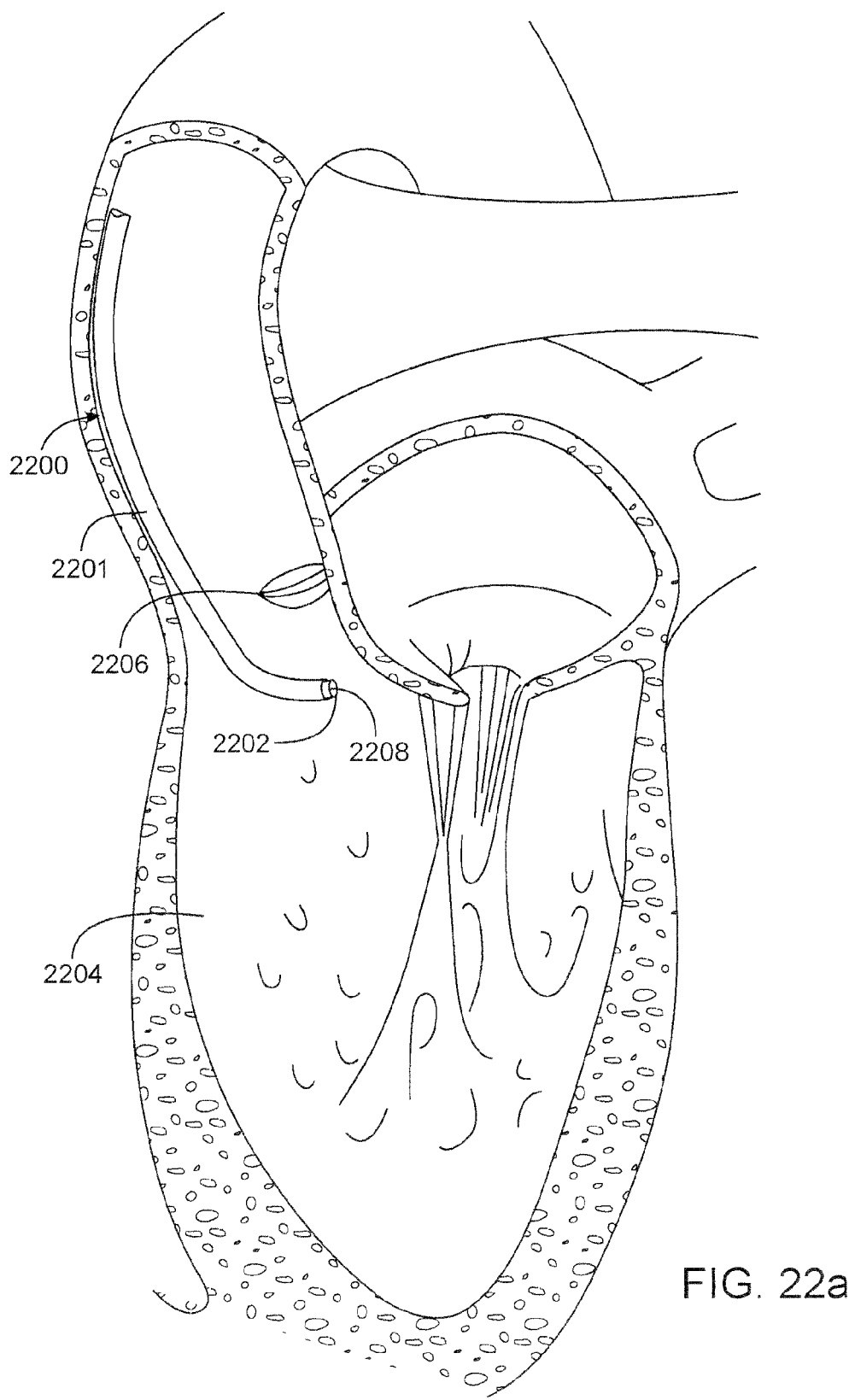
FIG. 22a is a cut-away front view of the left side of a heart in which an L-shaped catheter has been inserted in accordance with an embodiment of the present invention.

A catheter which may enable an orthogonal access to a mitral valve may enable the catheter to be more accurately positioned underneath the mitral valve. As discussed above, a catheter may become at least partially tangled in trabeculae which are located in the left ventricle of a heart. As such, inserting a catheter which does not extend too deeply into the left ventricle may prevent significant tangling. Any tangling may impede the efficiency with which the catheter may be positioned beneath a mitral valve. One catheter which may be less likely to become at least partially tangled in trabeculae, while also enabling an orthogonal access to a mitral valve, is an L-shaped catheter, which is shown in FIG. 22a. An L-shaped catheter arrangement 2200, which includes a delivery tube 2201 and an L-shaped catheter 2202 which may be formed from a biocompatible material that is typically also relatively flexible, is arranged to allow the tip of L-catheter 2202 to maintain an "L" shape when passed through an aortic valve 2206 into a left ventricle 2204. After delivery tube 2201 and L-shaped catheter 2202 are effectively "snaked" or inserted through a femoral artery, a tip 2208 of L-shaped catheter may be positioned at a top portion of left ventricle 2204, where there is typically a minimal amount of trabeculae.

Figure 22B:
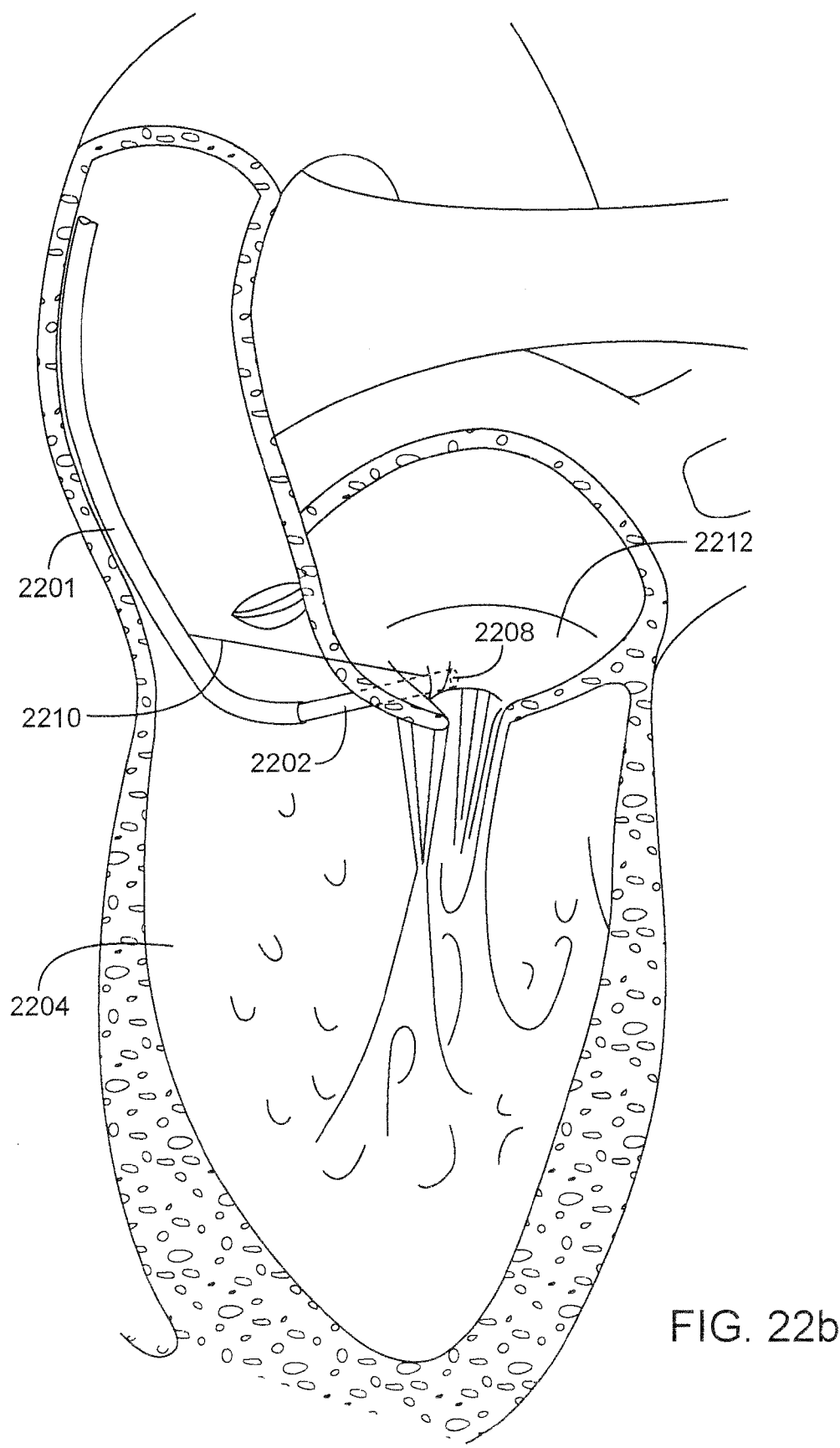
FIG. 22b is a cut-away front view of the left side of a heart in which an L-shaped catheter has been inserted and extended in accordance with an embodiment of the present invention.
Figure 22C:
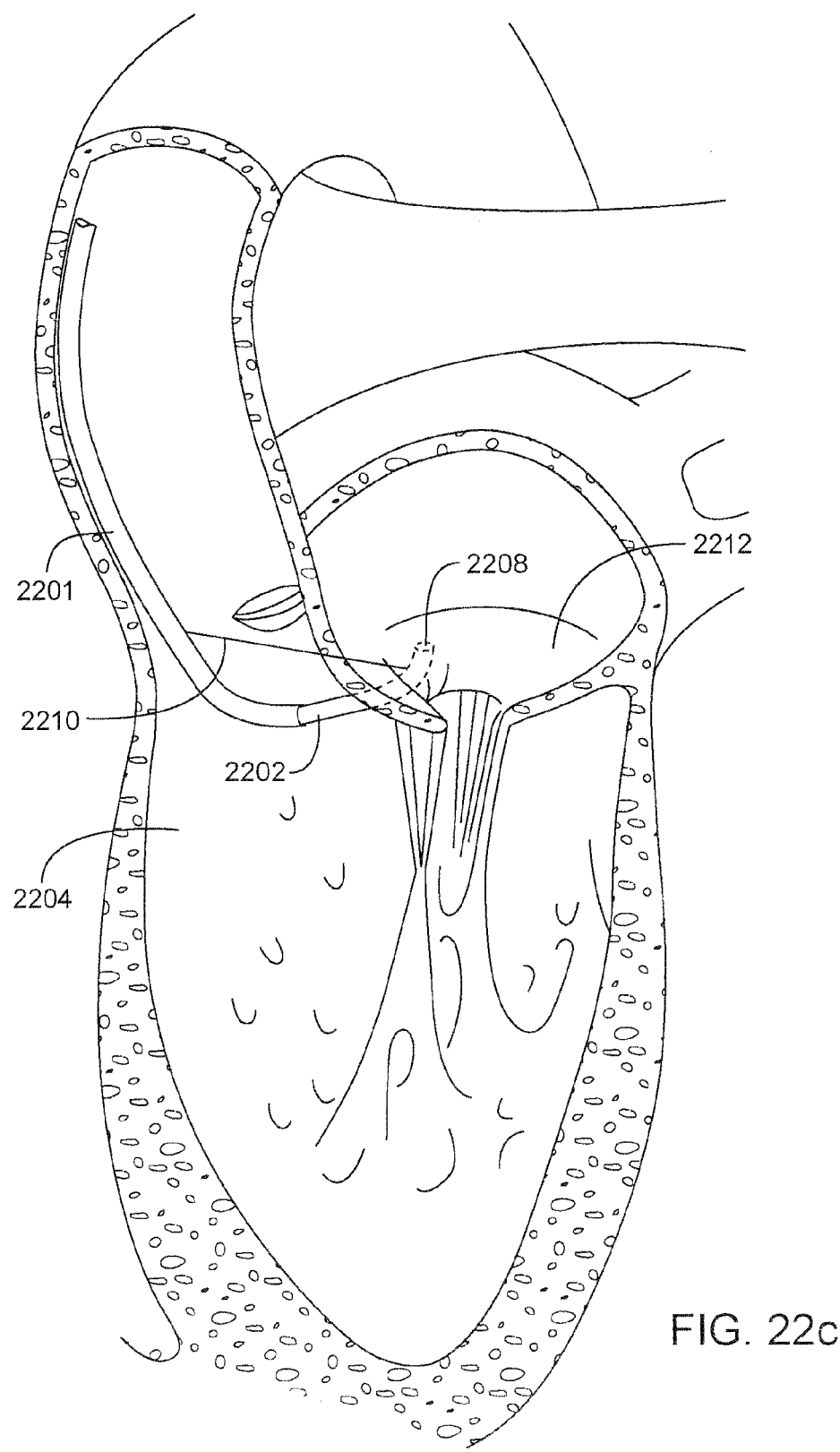
FIG. 22c is a cut-away front view of the left side of a heart in which an L-shaped catheter has been inserted, extended, and curved in accordance with an embodiment of the present invention.

Tip 2208 of L-shaped catheter 2202 may be extended in a straight orientation such that tip 2208 effectively forms an "L" with respect to delivery tube 2201 and the remainder of L-shaped catheter 2202. In one embodiment, as tip 2208 is extended under a mitral valve 2212, a string 2210 or another part, e.g., a wire, that may be coupled to tip 2208 may extend through an opening in delivery tube 2201 as shown in FIG. 22b. String 2210 may effectively allow tip 2208 to be bent or otherwise moved around underneath to position tip 2208 into contact with mitral valve 2212, as shown in FIG. 22c.

The use of string 2210 to pull on tip 2208 allows, in cooperation with extending L-shaped catheter 2202, tip 2208 to be moved beneath mitral valve 2212 into desired positions. Hence, desired locations beneath mitral valve 2212 may relatively easily be reached to enable plications (not shown) to be created in the desired locations. In the described embodiment, string 2210 may enable a curve to be created in L-shaped catheter 2202 that is substantially an approximately ninety degree curve.

L-shaped catheter 2202 may be used to create plications in mitral valve 2212 using a variety of different methods. Specifically, tip 2208 of L-shaped catheter 2202 may be temporarily fixed in a position beneath mitral valve 2212, e.g., in a gutter of the heart, during a process of creating a plication in mitral valve 2212. In one embodiment, suction may be used to gather a portion of tissue near mitral valve 2212 either such that a plication may be made in the portion, or such that a temporary anchor point may be created. Suction generally enables tissue to be substantially gathered such that an apparatus, as for example a clip or a similar apparatus, may be put into place to hold the gathered tissue. Alternatively, suction may be used to secure or firmly anchor tip 2208 against mitral valve 2212 such that an anchor for a plication may be deployed with improved accuracy. When tip 2208 is anchored into tissue near mitral valve 2212, an anchor for a plication or a temporary anchor may be more precisely placed, as the position of tip 2208 is effectively fixed.

Figure 23A:
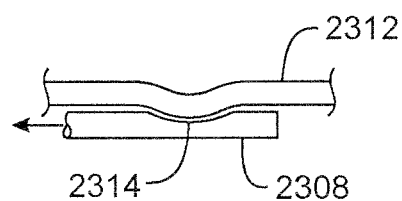
FIG. 23a is representation of a portion of a first catheter which may use suction to engage against tissue in accordance with an embodiment of the present invention.
Figure 23B:
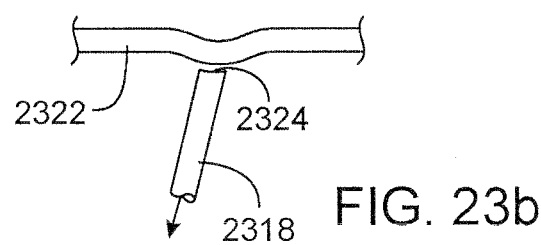
FIG. 23b is representation of a portion of a first catheter which may use suction to engage against tissue in accordance with an embodiment of the present invention.

FIGS. 23a and 23b are diagrammatic representations of orientations of a tip area of an L-shaped catheter which may be used with suction to anchor the tip area to a mitral valve in accordance with an embodiment of the present invention. As shown in FIG. 23a, a tip 2308 of a catheter such as an L-shaped catheter, e.g., L-shaped catheter 2202 of FIG. 22c, may include an opening 2314 on a side of tip 2308. Opening 2314 may be positioned under tissue 2312 such that when suction is applied through opening 2314, tip 2308 is effectively temporarily fixed against tissue 2312. Alternatively, as shown in FIG. 23b, a tip 2318 of an L-shaped catheter may include an end opening 2324, i.e., an opening at an endpoint of tip 2318, that allows opening 2324 to contact tissue 2322 such that when suction is applied through opening 2324, tip 2312 is held relatively firmly against tissue 2322. Temporarily anchoring a catheter near a mitral valve generally allows plication elements to be more accurately deployed using the catheter.

Figure 24A:
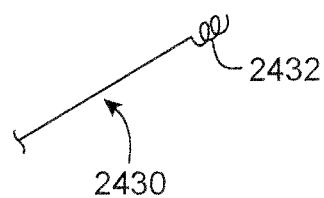
FIG. 24a is representation of a portion of a wire with a helical coil which may be used as a temporary anchor in accordance with an embodiment of the present invention.
Figure 24B:
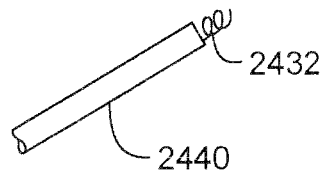
FIG. 24b is representation of a portion of a catheter with a helical coil which may be used as a temporary anchor in accordance with an embodiment of the present invention.

In lieu of using suction to anchor the tip area of a catheter to tissue near a mitral valve, a wire with a coil which may be extended through a catheter such that the wire may be temporarily anchored into tissue near the mitral valve such that other catheters may track over the wire. For example, a wire with a helical coil or a spiral at the tip may be engaged against tissue by applying force to the tip of the wire, turning the wire such that the helical coil portion of the wire turns through the tissue, the pushing the coil through the tissue. FIGS. 24a and 24b are diagrammatic representations of a wire with a helical coil which may be suitable for use in as a temporary anchor that is anchored into tissue near a mitral valve in accordance with an embodiment of the present invention. A wire 2430 with a coiled tip 2432, as shown in FIG. 24a, may be extended through a catheter (not shown) while a tip of the catheter may, in one embodiment, effectively be anchored against tissue near a mitral valve. Wire 2430 may be inserted in a catheter (not shown) such that a longitudinal axis of wire 2430 is parallel to a longitudinal axis of a tip (not shown) of the catheter. As shown in FIG. 24b, coiled tip 2432 may extend through a lumen of a tip 2440 of an L-shaped catheter to enable tip 2440 to be substantially anchored when coiled tip 2432 is anchored against tissue. Coiled tip 2432 is incorporated in the tip of the catheter, and would be engaged by rotating the entire catheter. This design features a working lumen that is coaxial with the center of the helical tip to enable a T-bar that is pushed down the lumen to pass through the center of the helix as the T-bar is effectively forced through tissue. It should be appreciated that, in one embodiment, a coiled tip may be included as a part of an L-shaped catheter, i.e., the catheter may include a coiled tip.

A wire 2430 with a coiled tip 2432 may generally be used as a temporary anchor which may remain coupled to tissue even after a catheter through which wire 2430 was deployed is retracted. That is, wire 2430 may serve as a track over which other catheters may be "run" to enable a particular position, i.e., a position identified by the location of coiled tip 2432 with respect to the tissue, to be repeatedly accessed or located by catheters.

In general, temporary fixation is a relatively reversible process. By effectively temporarily fixing or anchoring a catheter or a coiled tip of a wire against mitral valve tissue or tissue near a mitral valve, it is relatively easy to position, release, and re-position the wire and, hence, a catheter that tracks over the wire substantially without trauma, and substantially without causing an irreversible action to occur. A temporary anchor may provide a tension or counter-traction force for the application of a permanent anchor. That is, counter-traction on the temporary anchor may be used to provide a tissue penetration force for the permanent anchor. Possible permanent anchors generally include both single anchor points, e.g., applying one T-bar with a second T-bar being needed to for a plications, and dual anchor points, e.g., applying a clip or a staple which creates a plication between its points.

Figure 25:
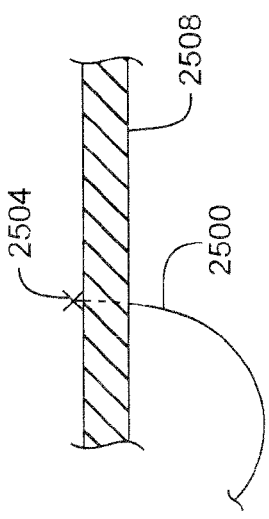
FIG. 25 is a representation of an anchor which is deployed and anchored into tissue in accordance with an embodiment of the present invention.

Once a catheter is effectively anchored into position, as for example over a wire such as wire 2430, then anchors which are used to create plications may be deployed. Typically, two anchor points are used to form a single plication. FIG. 25 is a diagrammatic representation of an anchor which is deployed and anchored into tissue in accordance with an embodiment of the present invention. An anchor 2504, which is coupled to a tether or a tail 2500, is deployed through tissue 2508 such that anchor 2504 is pushed through tissue 2508 while tail 2500 is allowed to extend, e.g., to an exterior of the body of a patient. In one embodiment, anchor 2504 may be a temporary anchor which is not actually used in the creation of a plication but is, instead, used to allow anchors used for plications to be positioned. In such an embodiment, anchor 2504 may be used to enable a first permanent anchor to be anchored. Alternatively, anchor 2504 may be an anchor, e.g., a T-bar, which is intended to be used to create a plication. For ease of discussion, anchor 2504 is described as being a first permanent anchor that was previously anchored into position by guiding a catheter over a temporary anchor (not shown).

An incrementor catheter may use tail 2500 as a guide over which the incrementor catheter may be positioned. An incrementor catheter, as shown in FIG. 26a, may generally include two sections. A first section 2602 of an incrementor catheter 2600, may be inserted over tail 2500. In one embodiment, first section 2602 may be used to insert anchor 2504, e.g., when incrementor catheter 2600 is configured as an L-shaped catheter.

Figure 26B:
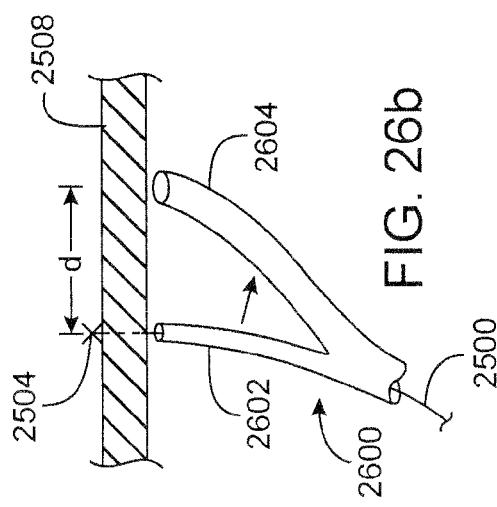
FIG. 26b is a representation of a portion of an incrementor catheter in an open configuration which is positioned over a tail and is extended such that a first section and a second section of the incrementor have tips that are separated by a distance in accordance with an embodiment of the present invention.
Figure 26A:
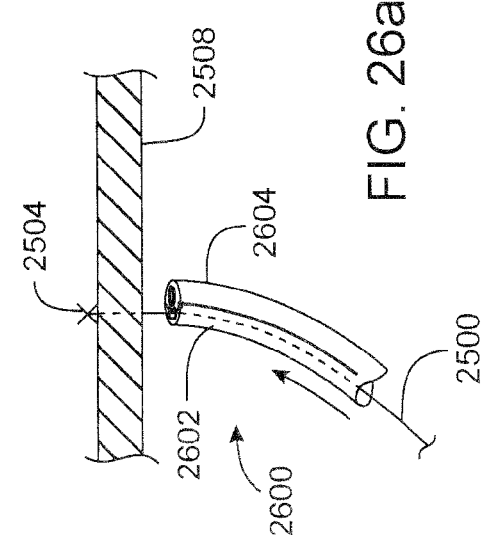
FIG. 26a is a representation of a portion of an incrementor catheter in a closed configuration which is positioned over a tail of an anchor in accordance with an embodiment of the present invention.

Once first section 2602 is positioned over tail 2500 such that first section 2602 is in relatively close proximity to tissue 2508, a second section 2604 may be extended away from first section 2602, as for example by a nominal separation or distance 'd,' as shown in FIG. 26b. The positioning of first section 2602 over tail 2500 enables first section 2602 to be temporarily fixed. With first section 2602 being temporarily fixed, second section 2604 may be controlled such that a tip of second section 2604 may be rotated, extended, or retraced to control the penetration angle of an anchor (not shown) that is to be deployed.

Additionally, when first section 2602 is temporarily fixed, the position of first section 2602 may be maintained for enough time to perform substantially all desired tests and to withstand forces associated with the desired test. Further, substantially all forces associated with the manipulation of incrementor catheter 2602.

Distance 'd' may be substantially any distance, and is typically selected to be a distance which allows a plication created using anchor 2504 and an anchor (not shown) that is to be deployed through second section 2604 to be effectively created. When second section 2604 is used to deploy either a temporary or permanent anchor (not shown), second section 2604 is effectively a working lumen of incrementor catheter 2600.

The location of anchors may generally be verified using a number of technologies which include, but are not limited to, ultrasound techniques, fluoroscopy techniques, and electrical signals. With some of the technologies, the injection of marking agents, e.g., contrast agents for fluoroscopy or microspheres for ultrasound, may increase contrast and promote visibility. Typically, such injections may be into a ventricular space, within mitral valve tissue, or in through the mitral valve tissue into atrial space. It should be appreciated that the verification of locations may further enable a distance 'd' between consecutive anchors to be more accurately maintained.

Figure 27:
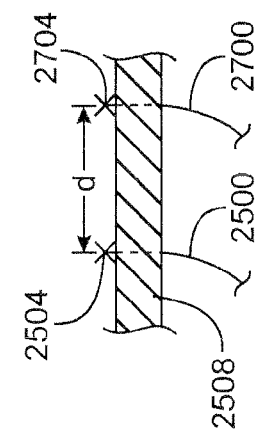
FIG. 27 is a representation of two anchors which may be used to create a plication in accordance with an embodiment of the present invention.

FIG. 27 is a diagrammatic representation of two anchors which may be used to create a plication in accordance with an embodiment of the present invention. Anchor 2504 and an anchor 2704, which may be deployed using second section 2604 of incrementor catheter 2600 of FIG. 26b, are separated by distance 'd.' Each anchor 2504, 2704 has a tail section, i.e., tail 2500 and a tail 2700, respectively, which, after incrementor catheter 2600 of FIG. 26b is withdrawn from underneath tissue 2508, may be pulled on or tensioned such that a plication is effectively created between anchor 2504 and anchor 2704. Once a plication is created, tails 2500, 2700 may be trimmed.

In general, a daisy chain of plications may be created using an incrementor catheter. That is, the incrementor catheter may be used to anchor a series of anchors which are each substantially separated by a distance 'd.' Once a daisy chain of anchors is in place in mitral valve tissue, pairs of the anchors may effectively be tied off to create a series or a daisy chain of plications. With reference to FIG. 28a-f, a process of creating a daisy chain of plications will be described in accordance with an embodiment of the present invention. As shown in FIG. 28a, a first anchor 2802a, which may be a T-bar, has a tail 2806a such as a suture and is anchored to tissue 2804. Typically, tissue 2804 is tissue of a mitral valve annulus, or tissue near a mitral valve. A second anchor 2802b, which has a tail 2806b is also anchored into tissue 2804. Typically, the distance between second anchor 2802b and first anchor 2802a is a measured distance, i.e., the distance between second anchor 2802b and first anchor 2802a is predetermined. In one embodiment, the distance is substantially controlled using an incrementor catheter.

Once first anchor 2802a and second anchor 2802b are in place, a locker 2810a is delivered over tails 2806a, 2806b, as shown in FIG. 28b. Once locker 2810a is delivered, tail 2806a may be tensioned, substantially locked, and trimmed. Tensioning of tail 2806b, as shown in FIG. 28c, allows a first plication 2820 to be effectively created. Tail 2806b remains untrimmed, as second anchor 2802b is arranged to be included in a second plication of a daisy chain of plications. That is, second anchor 2802b may effectively be shared by more than one plication. A third anchor 2802c which has a tail 2806c, as shown in FIG. 28d, is anchored into tissue 2804 at a specified distance from second anchor 2802b, e.g., through the use of an incrementor catheter.

A locker 2810*b* may be delivered over tail 2806*b* and tail 2806*c*, and tail 2806*b* may be tensioned, locked, and trimmed as shown in FIG. 28*e*. When tail 2806*c* is tensioned, a second plication 2830 is created, as shown in FIG. 28*f*. It should be appreciated that if tail 2806 is also locked and trimmed, then a daisy chain of two plications 2820, 2830 is completed. Alternatively, if more plications are to be added, then additional anchors and lockers may be positioned as appropriate such that tail 2806*c* serves as a "starting point" for the additional plications.

Figure 29A:
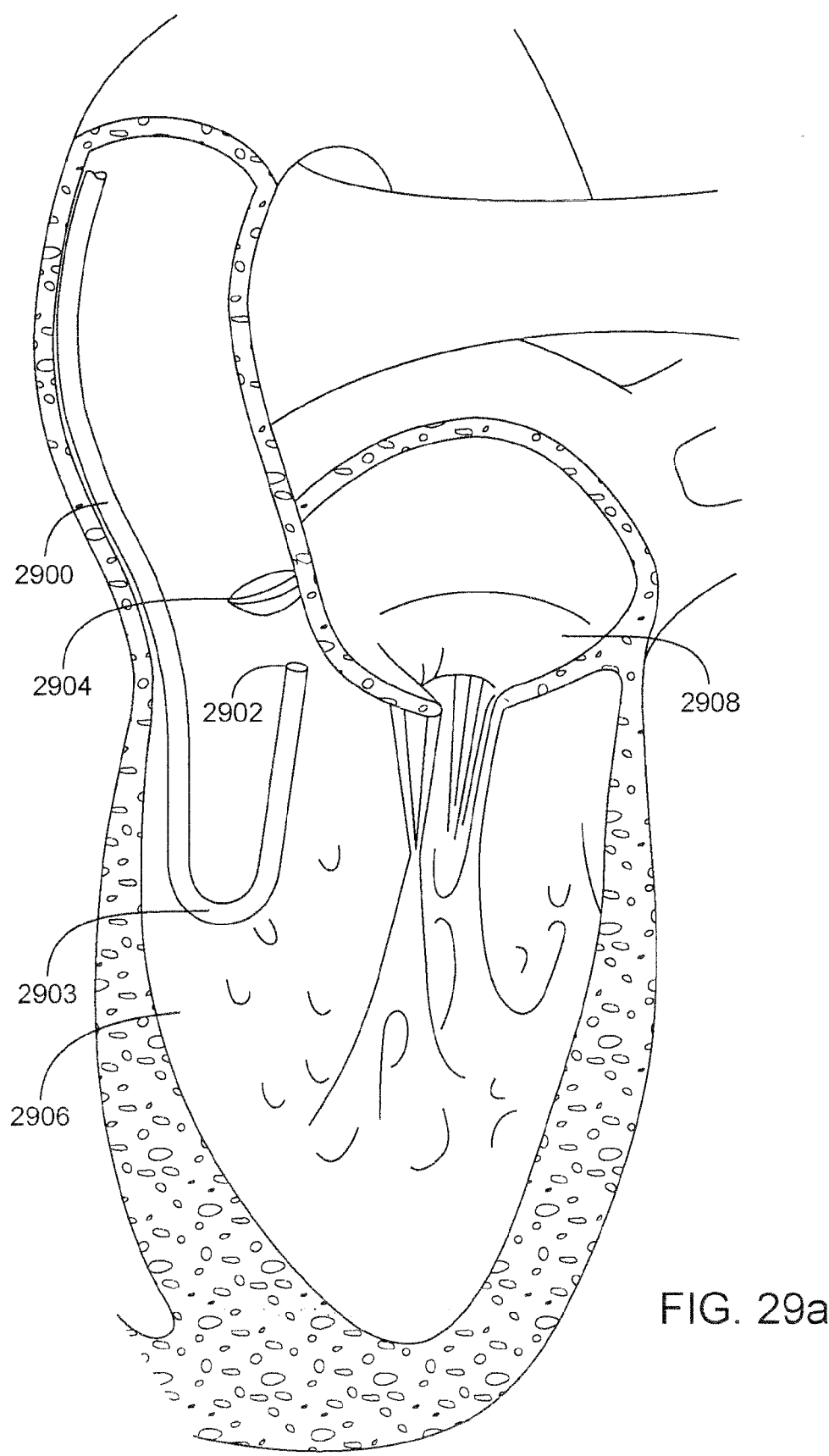
FIG. 29a is a cut-away front view of the left side of a heart in which a hook catheter has been inserted in accordance with an embodiment of the present invention.

Instead of using an L-shaped catheter to create anchor points, substantially any other suitable catheter may be used to access tissue near a mitral valve or a mitral valve annulus, e.g., to achieve a substantially orthogonal access to mitral valve tissue. In one embodiment, a suitable catheter may be a hook catheter which effectively includes an approximately 180 degree curve may be used to create anchor points and plications. FIG. 29*a* is a diagrammatic representation of a hook catheter in accordance with an embodiment of the present invention. A hook catheter 2900, which includes a tip 2902 that is effectively a terminus of a curved portion 2903 of hook catheter 2900, is inserted through an aortic valve 2904 into a left ventricle 2906.

Figure 29B:
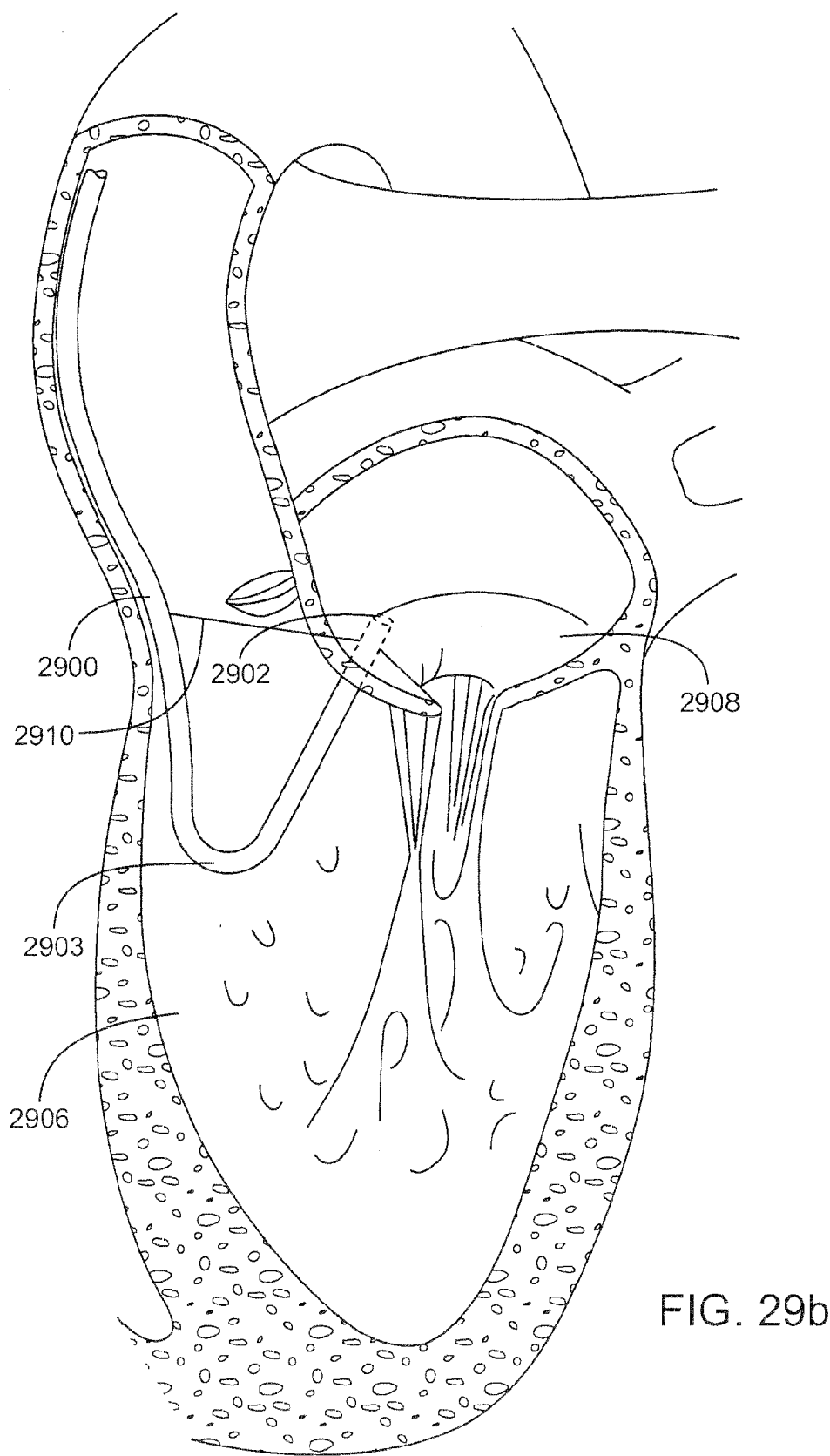
FIG. 29b is a cut-away front view of the left side of a heart in which a hook catheter is positioned beneath a mitral valve in accordance with an embodiment of the present invention.
Figure 29C:
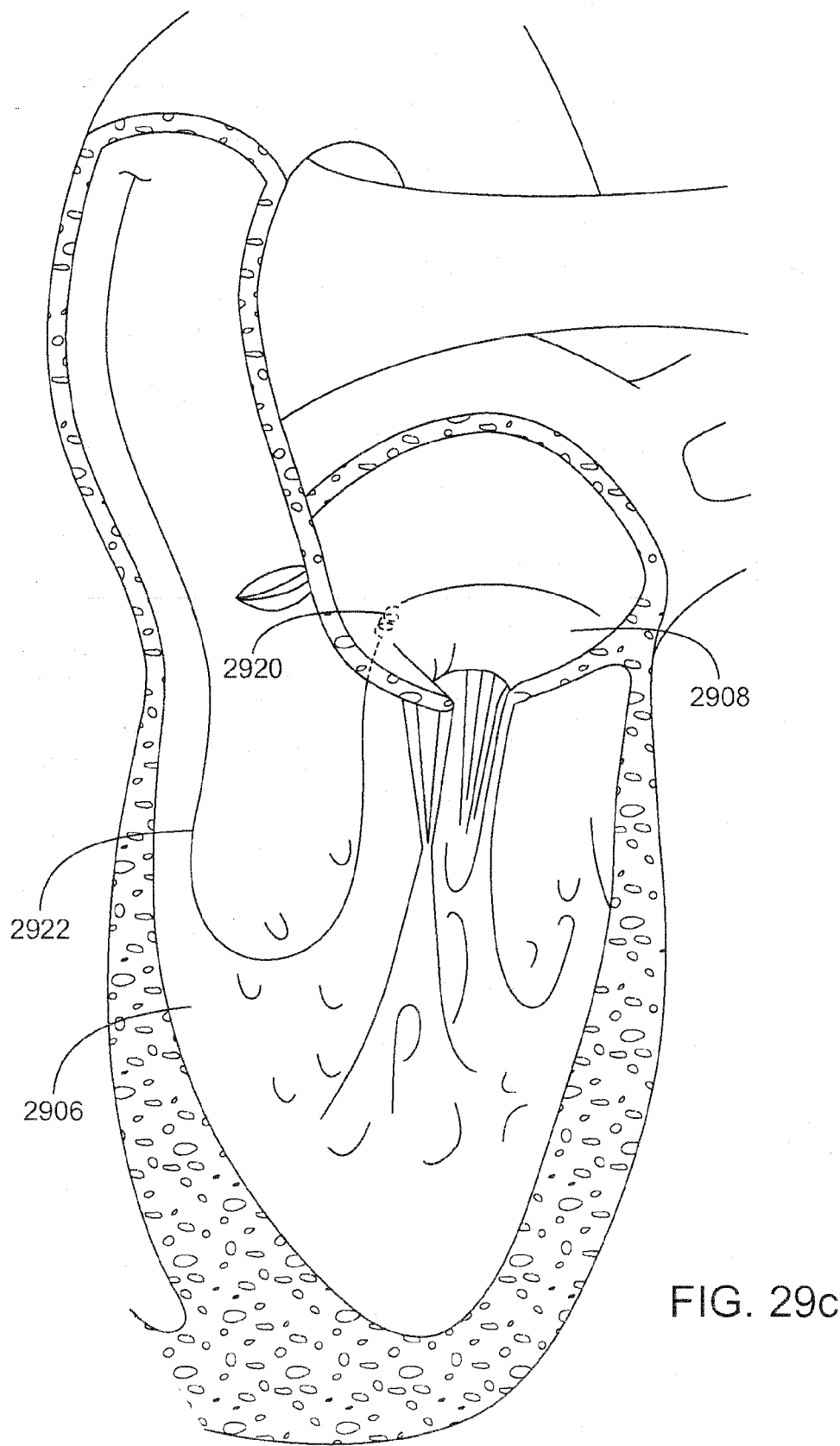
FIG. 29c is a cut-away front view of the left side of a heart in which a temporary anchor has been inserted in accordance with an embodiment of the present invention.

Once hook catheter 2900 is positioned or, more specifically, once tip 2902 is positioned near mitral valve tissue 2908, a string 2910 which may be coupled to tip 2902 as shown in FIG. 29*b*, may be pulled on or tensioned and slackened, as appropriate, to enable tip 2902 to be positioned in a desired location with respect to mitral valve tissue 2908. As will be appreciated by those skilled in the art, string 2910 is often a wire such as a pull wire or a deflection wire that is axially translatable. By allowing string 2910 to enable tip 902 to be positioned in a desired location, hook catheter 2900 may effectively be considered to be a deflectable or steerable tip catheter. A temporary anchor, e.g., a helical coil such as helical coil 2432 of FIG. 24*a*, may be anchored to mitral valve tissue 2908 by deploying the temporary anchor through hook catheter 2900. FIG. 29*c* is a diagrammatic representation of a temporary anchor that is positioned within a heart in accordance with an embodiment of the present invention. An anchoring coil 2920, which is coupled to a wire 2922, may be anchored to mitral valve tissue 2908 such that wire 2922 may serve as a guide over which a catheter, as for example either a catheter such as a hook catheter which delivers a permanent anchor or an incrementor catheter, which may also deliver a permanent anchor, may be positioned.

Figure 29D:
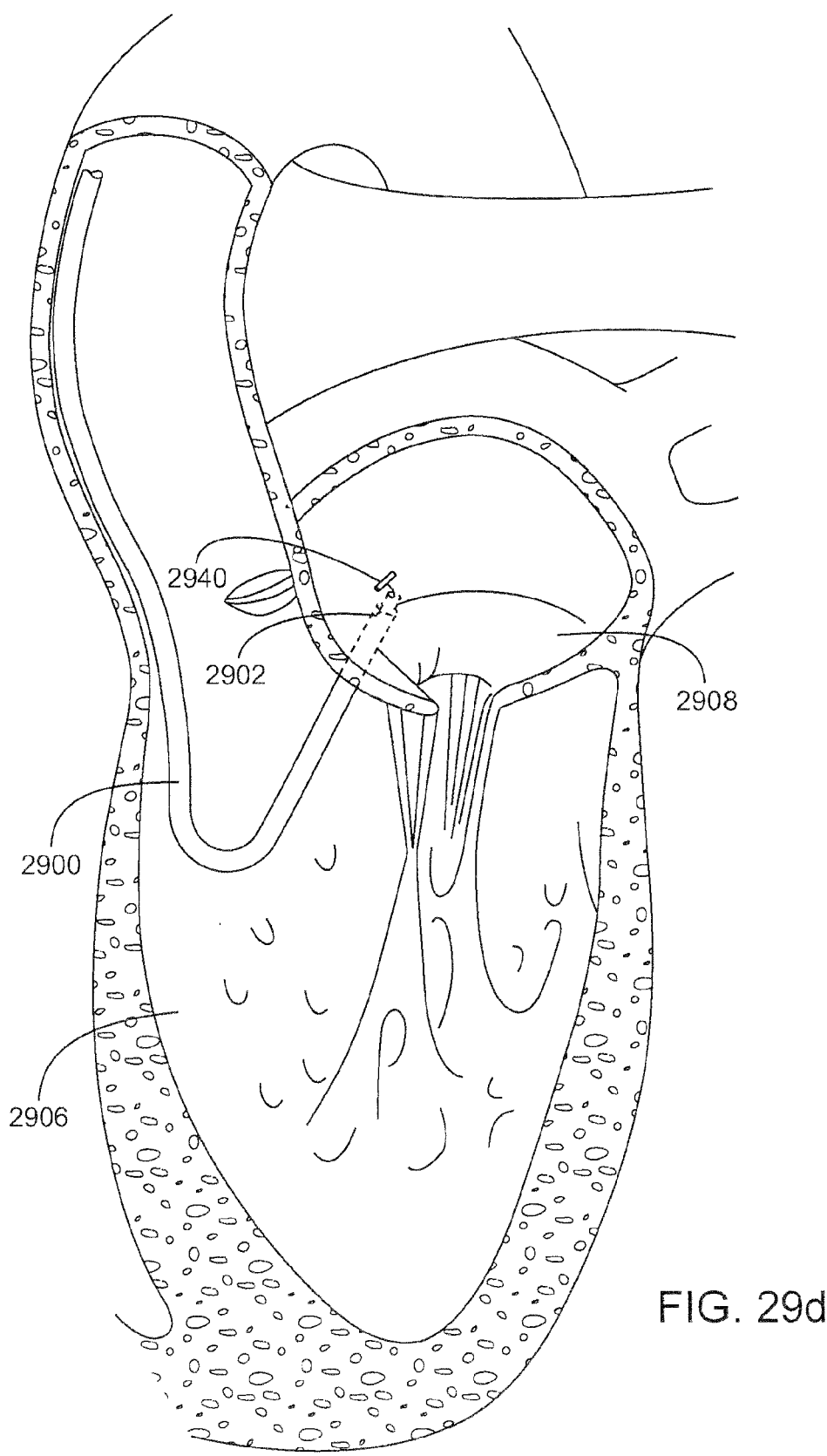
FIG. 29d is a cut-away front view of the left side of a heart in which a hook catheter which carries a permanent anchor is inserted in accordance with an embodiment of the present invention.
Figure 29E:
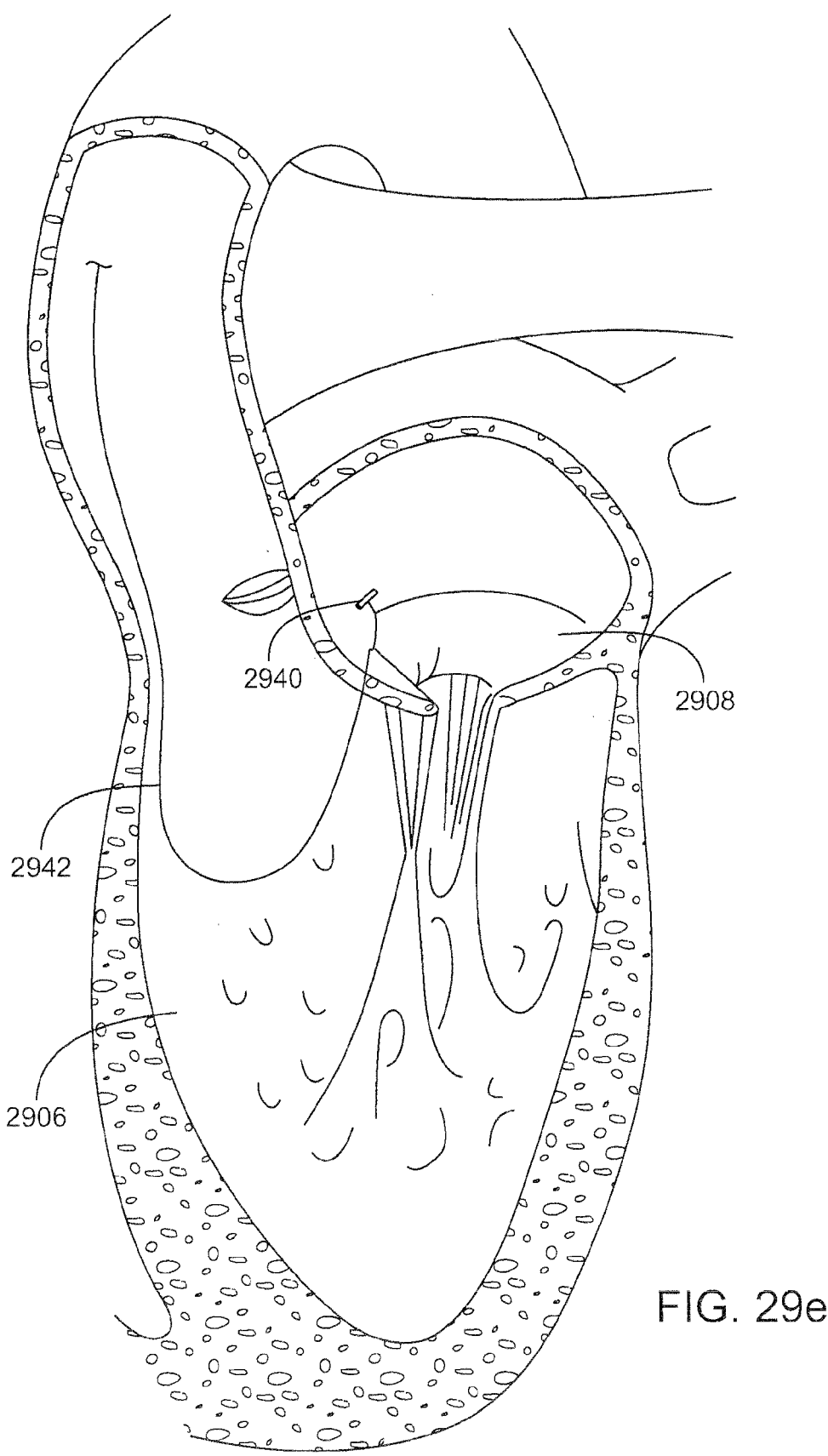
FIG. 29e is a cut-away front view of the left side of a heart in which a permanent anchor has been inserted in accordance with an embodiment of the present invention.

In lieu of using hook catheter 2900 to deploy a temporary anchor, catheter 2900 may instead be used to deploy a more permanent anchor such as a T-bar. As shown in FIG. 29*d*, a T-bar 2940 may be pushed through mitral valve tissue 2908 using tip 2902 of hook catheter 2900. When hook catheter 2900 is withdrawn from left ventricle 2906, T-bar 2940 effectively remains anchored in mitral valve tissue 2908, while a tail 2942 of T-bar 2940 may extend to an exterior of the body of a patient, as shown in FIG. 29*e*.

Figure 29F:
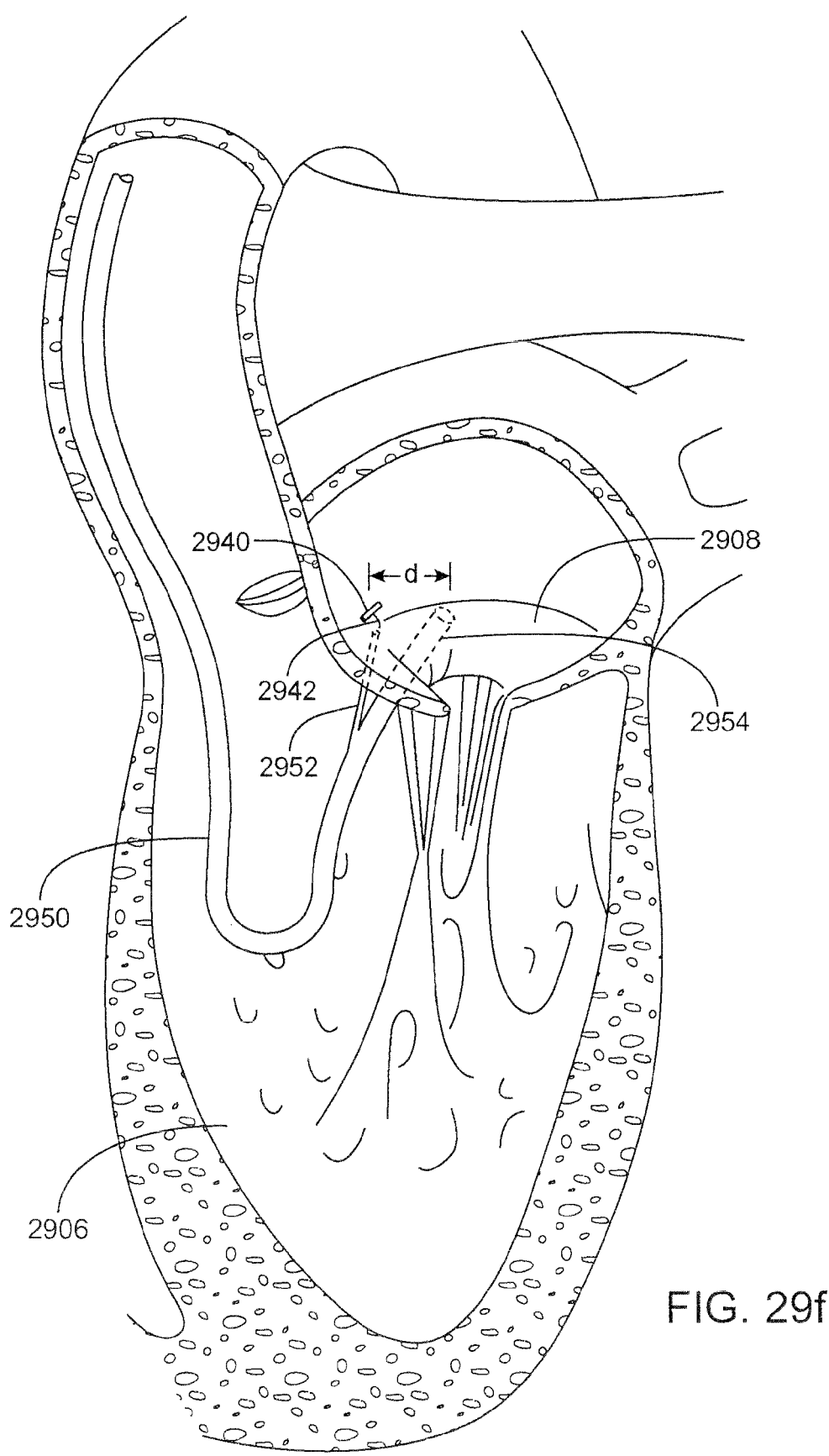
FIG. 29f is a cut-away front view of the left side of a heart in which an incrementor catheter has been inserted in accordance with an embodiment of the present invention.

After T-bar 2940 or, more generally, an anchor is in position, then an incrementor catheter may be snaked or otherwise passed over tail 2942. FIG. 29*f* is a diagrammatic representation of an incrementor catheter that is positioned over tail 2942 in accordance with an embodiment of the present invention. An incrementor catheter 2950 is positioned such that a first section 2952 of incrementor catheter 2950 may be guided by tail 2942 until a tip of first section 2952 is substantially directly under T-bar 2940. Then, a second section 2954 of incrementor catheter 2950 may be extended until a tip of second section 2954 is positioned approximately a distance 'd' away from T-bar 2940. A second T-bar (not shown) or anchor may then be deployed using second section 2954. Once a second T-bar is deployed, incrementor catheter 2950 may be removed from left ventricle 2906.

Figure 29G:
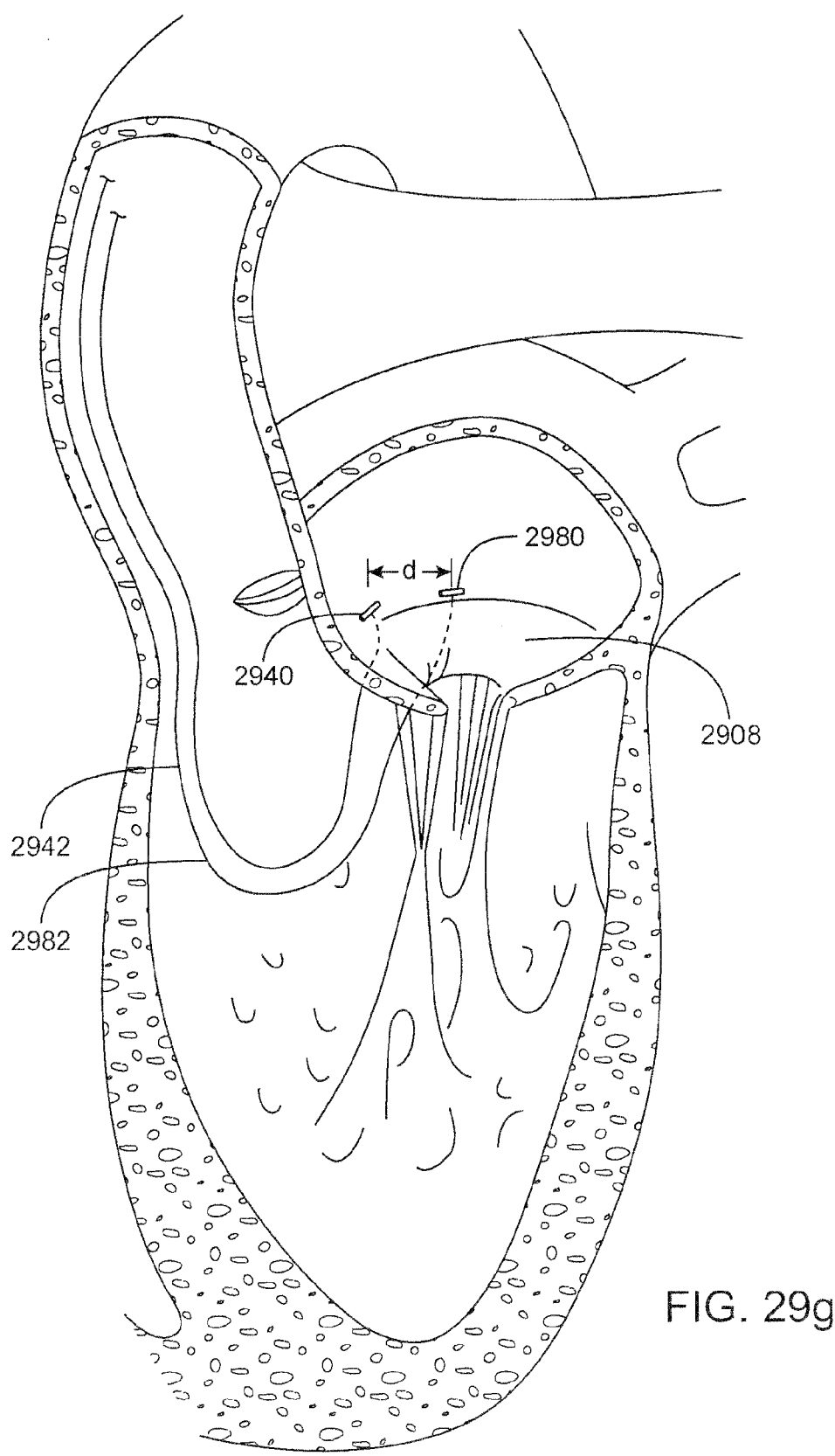
FIG. 29g is a cut-away front view of the left side of a heart in which two permanent anchors have been inserted in accordance with an embodiment of the present invention.

The use of an incrementor catheter 2950 allows two T-bars, e.g., T-bar 2940 and T-bar 2980 of FIG. 29*g*, to be anchored to mitral valve tissue 2908 such that T-bars 2940, 2980 may be spaced apart at approximately a distance 'd,' while tails 2942, 2982, respectively, may extend outside of a body of a patient. In other words, incrementor catheter 2950 generally enables the distance between adjacent T-bars to be more carefully controlled.

Figure 29H:
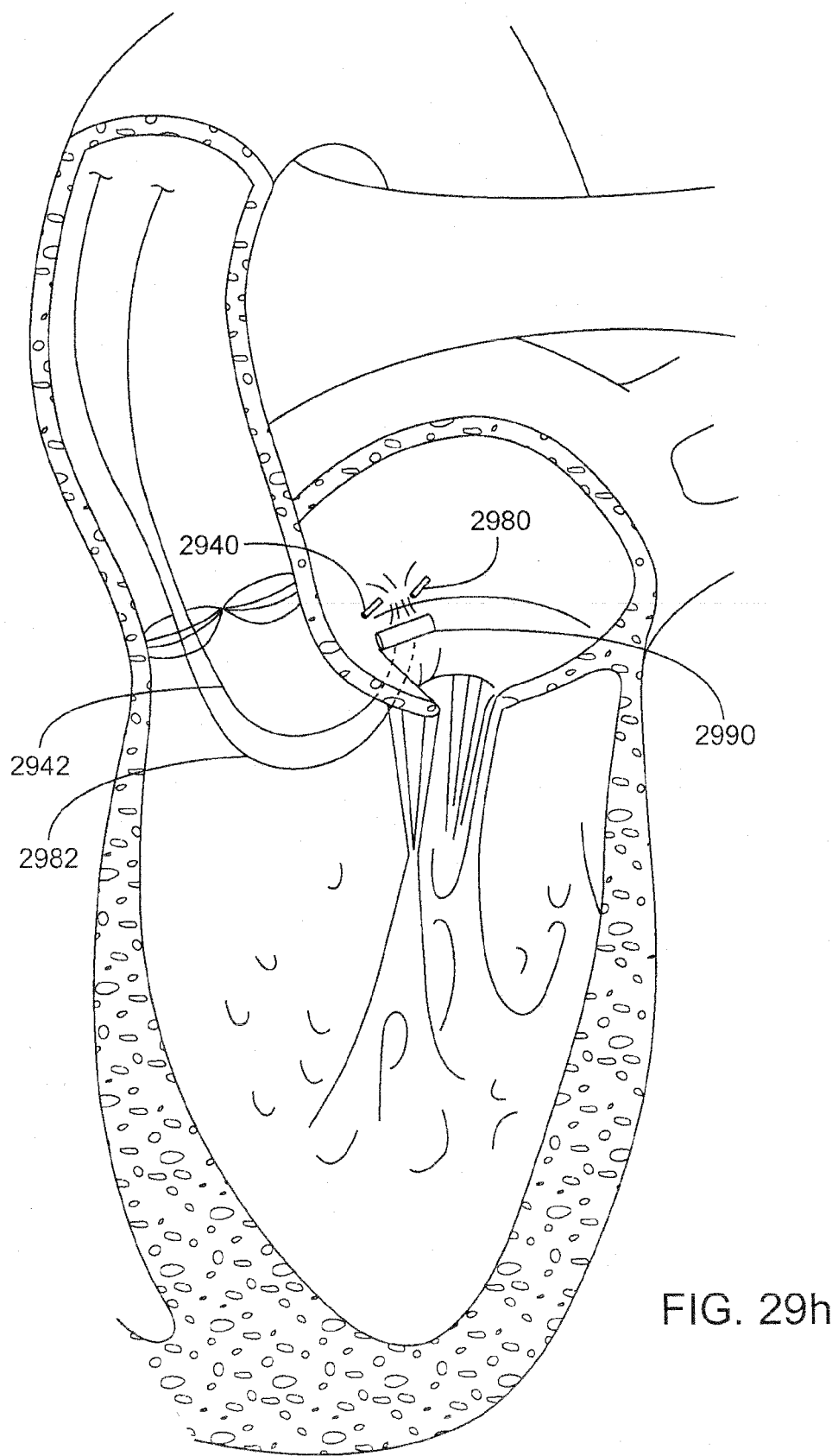
FIG. 29h is a cut-away front view of the left side of a heart in which two permanent anchors and a locking device or locker have been inserted in accordance with an embodiment of the present invention.

In order to create a plication using T-bars 2940, 2980, a locking bar 2990, as shown in FIG. 29*h*, may be provided over tails 2942, 2982 such that mitral valve tissue 2908 may effectively be pinched between T-bars 2940, 2980 and locking bar 2990. Once a plication is created, tails 2942, 2982 may be trimmed or otherwise cut.

Figure 30:
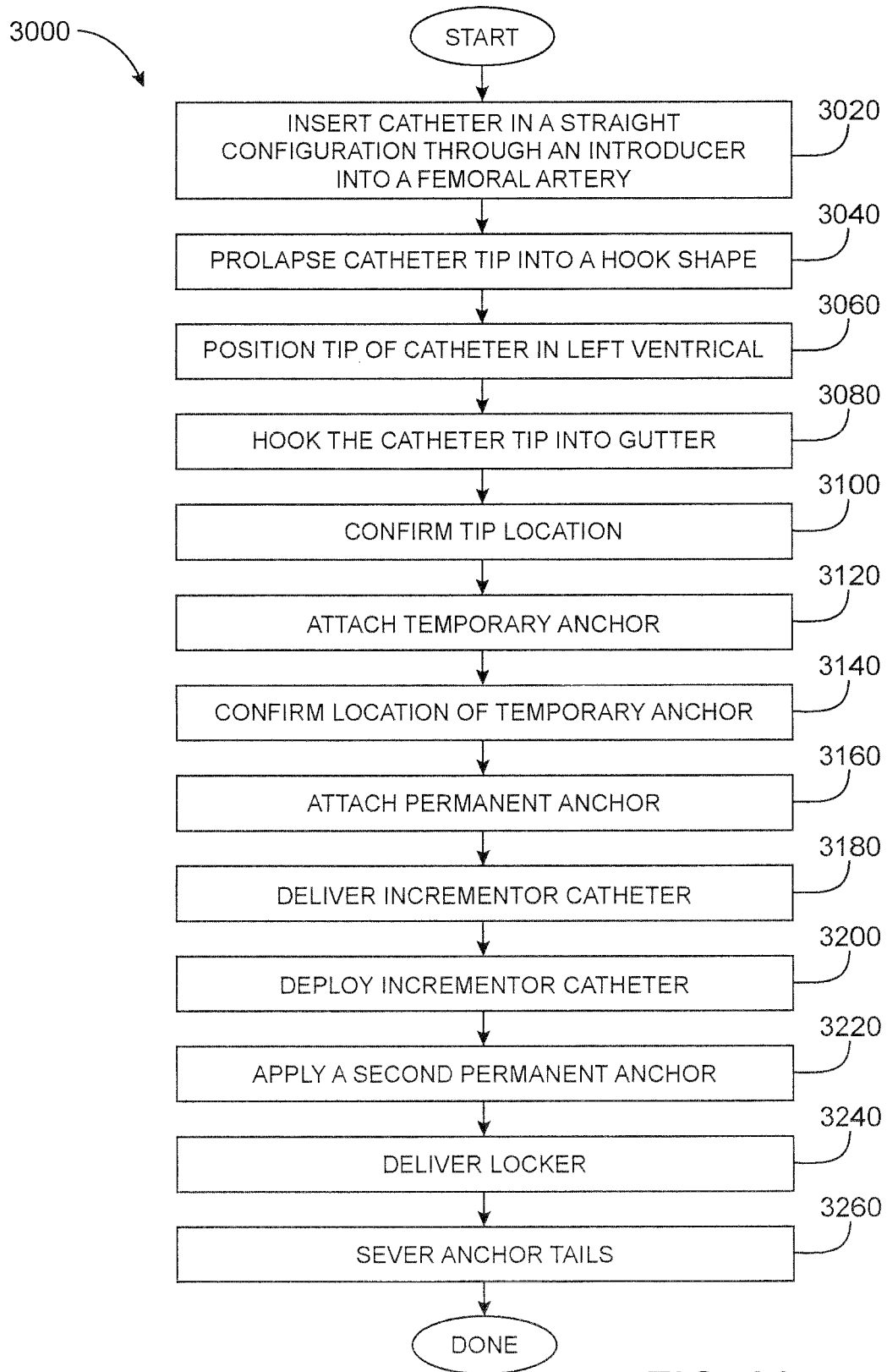
FIG. 30 is a process flow diagram which illustrates the steps associated with one method of creating a plication using an incrementor catheter in accordance with an embodiment of the present invention.

With reference to FIG. 30, the steps associated with one method of creating a plication using an access catheter which has a 180 degree retrograde active-curve tip, e.g., a hook catheter, an incrementor catheter, and a helical coil for creating a temporary anchor will be described in accordance with an embodiment of the present invention. A process 3000 begins at step 3020 in which a catheter, e.g., a hook catheter, is inserted in a substantially straight configuration through an introducer into a femoral artery of a patient. Once the catheter is inserted, the tip of the catheter is prolapsed into a hook shape in step 3040. A gap between an end of the hook portion and the main portion of the catheter may be reduced to a dimension that is small enough to prevent tangling of the tip in chords or leaflets of the heart. Prolapsing of the tip may generally occur within the aorta of a heart, at a femoral artery bifurcation, or within the left ventricle of the heart. It should be appreciated that when the tip of the catheter is deflectable, the tip of the catheter may be deflected or substantially actively changed into a hook shape within the aorta of the heart, or within the left ventricle of the heart.

In step 3060, the tip of the catheter may be positioned within the left ventricle. By way of example, the catheter tip may be positioned at a level that is just inferior to the level of the mitral valve annulus, and the catheter segment that includes the hook shape may be rotated such that it lies against either the anterior or posterior aspect of the aortic outflow tract, depending upon which aspect is to be treated. In one embodiment, the distal catheter segment is aligned such that when extended, the tip of the catheter may point towards one of the entrances to the gutter of the heart. The entrances to the gutter of the heart may include substantially any relatively clear entrance to the gutter with respect to the leaflets of the heart, as for example a medial P1 location, a mid P2 location, or a lateral P3 location.

After the tip of the catheter is positioned, the tip of the catheter may be hooked into the gutter in step 3080. Hooking the catheter tip into the gutter may include repeatedly extending the retrograde tip to increase the gap between the tip and the proximal segment of the catheter, retracting the entire catheter and sensing engagement of the tip with the gutter, and, if necessary, one again positioning the tip of the catheter in the left ventricle before rehooking the tip.

Once the catheter tip is hooked into the gutter, the location of the tip is confirmed in step 3100. Confirming the location of the tip may include, but is not limited to, as previously mentioned, sensing electrical signals of the heart, fluoroscopy with or without the injection of contrast, and ultrasound with or without the injection of microspheres. When the tip location is confirmed, a temporary anchor may be attached in step 3120. The temporary anchor may be a helical coil, e.g., helical coil 2432 of FIG. 24*a*, that is attached by applying a longitudinal pressure and torque. Typically, when the helical coil is attached, a lumen or a tail of the helical coil remains connected to the helical coil.

In the described embodiment, after the temporary anchor is attached, the location of the temporary anchor is confirmed in step 3140. Methods used to confirm the location of the temporary anchor may be the same as methods used to confirm the location of a catheter tip, and may also include injecting contrast or microspheres into tissue or through tissue to the atrial space above a mitral valve.

A permanent anchor is attached in step 3160 using the connection to the temporary anchor as a guide. The permanent anchor may be attached to the same location, and may provide a counter-traction force for tissue engagement. Like the temporary anchor, the permanent anchor generally includes a tail.

Once a permanent anchor is in place, an incrementor catheter is delivered into the heart in step 3180. In general, the incrementor catheter is delivered in a closed configuration to the location of the first anchor, e.g., the permanent anchor attached in step 3160, by tracking a first section of the incrementor catheter over the tail of the first anchor. After the incrementor catheter is delivered, the incrementor catheter may be deployed in step 3200 to create a nominal distance or gap between the first anchor location and the working lumen, e.g., a second section, of the incrementor catheter. Then, in step 3220, a second permanent anchor may be applied at the nominal distance from the first permanent anchor. It should be appreciated that temporary anchors may be used to facilitate the positioning of the second permanent anchor. Applying the second permanent anchor typically includes retracting the incrementor catheter once the second permanent anchor is anchored into a desired location.

After both the first permanent anchor and the second permanent anchor are applied, a locker is delivered into the heart in step 3240. Delivering the locker generally includes tracking the locker or locking device over the two tails of the first and the second permanent anchors. The locker may be fixed into position by applying tension to the locker to create a plication substantially between the two permanent anchors.

Once the locker has been tensioned, the tails of the anchors may be severed, and the process of creating a plication is completed. It should be appreciated that, in one embodiment, steps 3180 to 3260 may generally be repeated to create a daisy chain of interlocking plications.

Although only a few embodiments of the present invention have been described, it should be understood that the present invention may be embodied in many other specific forms without departing from the spirit or the scope of the present invention. By way of example, methods of introducing plication elements or suture structures into the left ventricle to correct for mitral valve leakage, or mitral valve insufficiency, may be applied to introducing plication elements or suture structures which correct for leakage in other valves. For instance, the above-described procedure may be adapted for use in repair a leaking valve associated with a right ventricle.

While creating local plications in fibrous tissue associated with the mitral valve of the heart has generally been described, the plications may also be created in other types of tissue which are near, around, in proximity to, or include the mitral valve. As will be appreciated by those skilled in the art, other tissues to which plications may be formed that are near, around, in proximity to, or include the mitral valve include tissues associated with the coronary sinus, tissues associated with the myocardium, or tissues associated with the wall of the left ventricle. In one embodiment, a plication may be substantially directly formed in the leaflets of the mitral valve.

It should be understood that although a guide wire has been described as including an anchoring tip to anchor the guide wire to a wall of the left ventricle, a guide wire may be anchored with respect to the left ventricle in substantially any suitable manner. By way of example, a guide wire may include an anchoring feature which is located away from the tip of the guide wire. In addition, a guide wire may more generally be any suitable guiding element which is configured to facilitate the positioning of an implant.

While access to the gutter of the left ventricle has been described as being associated with a minimally invasive catheter annuloplasty procedure in which local plications are formed, it should be understood that the gutter of the left ventricle may also be accessed, e.g., for an annuloplasty procedure, as a part of a surgical procedure in which local plications are formed. For instance, the aorta of a heart may be accessed through an open chest surgical procedure before a catheter is inserted into the aorta to reach the left ventricle. Alternatively, suture structures or plications elements may be introduced on a ventricular side of a mitral valve through a ventricular wall which is accessed during an open chest surgical procedure.

Pledgets have been described as being used in conjunction with, or as a part of, suture structures to facilitate the growth of scar tissue as a result of an annuloplasty procedure. It should be appreciated, however, that the use of pledgets is optional. In addition, although pledgets have generally not been described as being used with clip elements which create local plications, it should be understood that pledgets may also be implemented with respect to clip elements. By way of example, a clip element which includes tines may be configured such that the tines pierce through pledgets before engaging tissue without departing from the spirit or the scope of the present invention.

When a clip element has tines that are arranged to pierce through a pledget before engaging tissue, the pledget may be of a hollow, substantially cylindrical shape that enables the pledget be delivered to a left ventricle over a guide wire positioned in the gutter of the left ventricle. The clip element may then be delivered by a catheter through the pledget. A substantially cylindrically shaped, hollow pledget which is to be used with a suture structure may also be delivered over a guide wire, and the suture structure may then be delivered through the pledget. Delivering the suture structure through the pledget may enable a loop of thread that remains after the suture structure is locked into place to remain substantially within the pledget.

The configuration of clip elements may generally vary widely. Specifically, the shape of clip elements, the size of clip elements, and the materials from which the clip elements are formed may be widely varied. For instance, in addition to clip elements that are formed from shape memory material, preloaded, or self-locking using mechanical structures, clip elements may also be formed from thermally expandable materials. That is, a clip may be formed such that it is in an open or flat position when delivered into a left ventricle. Such a clip may have an outer or "bottom" element that has a relatively high coefficient of thermal expansion, and an inner or "top" element that deforms under the load generated by the outer element when heat is applied to cause the outer element to bend. Such a clip, once bent or deformed through the application of heat, may pierce tissue. When more heat is applied, the clip may bend more such that tissue is engaged between ends or sides of the clip to create a local plication. In such a system, the inner material may be arranged to maintain its deformed shape once heat is no longer applied, and the heat may be applied through a catheter.

Suture structures and plication elements have been described as being used to correct for mitral valve insufficiency. In general, suture structures and plication elements may also be used to essentially prevent the onset of mitral valve insufficiency. That is, local plications may be created to effectively stem the progression of mitral valve insufficiency be reinforcing the perimeter of the annulus around the mitral valve.

While suture structures that include T-bars, thread, and locking elements, and are delivered to a left ventricle using a catheter, may be used to form discrete plications in fibrous tissue around the mitral valve, it should be appreciated that sutures may also be sewn into the fibrous tissue. For example, a catheter which is inserted into the left ventricle through the aorta may be configured to sew sutures into the fibrous tissue using mechanisms carried by the catheter. Such sutures that are sewn into the fibrous tissue may be sewn in any conventional orientation, e.g., in an arc along the perimeter of the posterior leaflet of the mitral valve.

Suture structures that include T-bars have generally been described as including two T-bars which are located at ends of a thread, with a locking element and pledgets located therebetween, as shown, for example, in FIG. 10a. The configuration of suture structures, however, may vary widely. By way of example, a suture structure with two T-bars may include one T-bar at one end of the thread and a second T-bar which is located along the length of the thread such that pulling on a loose end of the thread pulls the two T-bars together. Alternatively, a suture structure may include more than two T-bars.

In general, the use of a single element type to create local plications during an annuloplasty procedure has been described. It should be understood that in one embodiment, different element types may be used in a single annuloplasty procedure. For instance, both clip elements and suture elements may be used to create plications during a single annuloplasty procedure. Alternatively, different types of clip elements or different types of suture elements may be used during a particular annuloplasty procedure.

The steps associated with performing a catheter-based annuloplasty may be widely varied. Steps may generally be added, removed, reordered, and altered without departing from the spirit or the scope of the present invention. Therefore, the present examples are to be considered as illustrative and not restrictive, and the invention is not to be limited to the details given herein, but may be modified within the scope of the appended claims.

What is claimed is:

1. An anchor delivery catheter for performing catheter-based annuloplasty by delivering anchors to heart tissue, the anchor delivery catheter comprising:
a distal catheter portion adapted to be received into a chamber of a heart, said distal catheter portion including a distal tip and at least one sidewall defining a lumen along the catheter;
an opening in said sidewall of said distal catheter portion and spaced proximally from said distal tip, said opening communicating with said lumen to facilitate the delivery of anchors through said lumen and said opening to heart tissue;
anchor delivery structure disposed in said lumen;
a plurality of anchors releasably supported on said anchor delivery structure and adapted to anchor to the heart tissue, wherein each anchor includes a rigid member at a distal end thereof and the rigid member is at least partially disposed along said anchor delivery structure, wherein the anchor delivery structure extends through each of the rigid members of the plurality of anchors which are located in series along the anchor delivery structure; and
at least one elongate tensile member having a free proximal end, the elongate tensile member having a distal end operatively coupled to the rigid member of the at least one anchor, the at least one elongate tensile member extending proximally from the rigid member;
said anchor delivery structure being movable relative to the distal catheter portion in the chamber of the heart from a first position wherein said anchor is disposed within said lumen, to a second position wherein said anchor is moved through said opening to engage the heart tissue, and to a third position wherein said anchor is separated from said anchor delivery structure and remains engaged with the heart tissue.

2. The anchor delivery catheter of claim 1, wherein said distal catheter portion is convertible between a first condition wherein said distal catheter portion has a shape that does not conform to the contour of the gutter of the mitral valve, and a second condition wherein the shape of said distal catheter portion conforms to the contour of the gutter of the mitral valve.

3. The anchor delivery catheter of claim 1, further comprising at least a second anchor disposed within said lumen and supported on said anchor delivery structure, the second anchor including a rigid member at a distal end thereof and a second elongate tensile member extending proximally therefrom.

4. The anchor delivery catheter of claim 3, wherein said anchor delivery structure is further moveable to move said second anchor through said opening to engage the heart tissue.

5. The anchor delivery catheter of claim 3, further comprising a locking element coupled to said tensile members for movement therealong relative to said anchors, wherein said locking element is adapted to remain coupled to said tensile members and separated from the anchor delivery catheter.

6. An anchor delivery catheter for performing catheter-based annuloplasty by delivering anchors to heart tissue, the anchor delivery catheter comprising:
a distal catheter portion adapted to be received into a chamber of a heart, said distal catheter portion including a distal tip and at least one sidewall defining a lumen along the catheter;
an opening in said sidewall of said distal catheter portion and spaced proximally from said distal tip, said opening communicating with said lumen to facilitate the delivery of anchors through said lumen and said opening to heart tissue;
anchor delivery structure disposed in said lumen;
at least first and second anchors releasably and serially supported on said anchor delivery structure and adapted to anchor to the heart tissue, wherein each anchor includes a rigid member at a distal end thereof and each rigid member is at least partially disposed along said anchor delivery structure, wherein the anchor delivery structure extends through each of the rigid members of the first and second anchors, the rigid members being supported in series along the anchor delivery structure; and
at least first and second elongate tensile members each having a free proximal end, and each elongate tensile member having a distal end operatively coupled to a respective rigid member of the at first and second anchors, the at least first and second elongate tensile members extending independently and alongside one another and proximally the respective rigid members;

said anchor delivery structure being movable relative to the distal catheter portion in the chamber of the heart from a first position wherein said first anchor is disposed within said lumen, to a second position wherein said first anchor is moved through said opening to engage the heart tissue, and to a third position wherein said first anchor is separated from said anchor delivery structure and remains engaged with the heart tissue while said elongate tensile members extend alongside one another proximally to a location that is accessible exteriorly of a patient.

7. The anchor delivery catheter of claim 6, wherein said distal catheter portion is convertible between a first condition wherein said distal catheter portion has a shape that does not conform to the contour of the gutter of the mitral valve, and a second condition wherein the shape of said distal catheter portion conforms to the contour of the gutter of the mitral valve.

8. The anchor delivery catheter of claim 6, wherein said anchor delivery structure is further moveable to move said second anchor through said opening to engage the heart tissue.

9. The anchor delivery catheter of claim 8, further comprising a locking element coupled to said tensile members for movement therealong relative to said anchors, wherein said locking element is adapted to remain coupled to said tensile members and separated from the anchor delivery catheter.

* * * * *